(12) United States Patent
Kaser et al.

(10) Patent No.: US 12,331,343 B2
(45) Date of Patent: Jun. 17, 2025

(54) FAMIN ASSAY METHODS

(71) Applicant: Cambridge Enterprise Limited, Cambridge (GB)

(72) Inventors: Arthur Kaser, Cambridge (GB); Mohammed Zaeem Cader, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 852 days.

(21) Appl. No.: 17/312,350

(22) PCT Filed: Dec. 9, 2019

(86) PCT No.: PCT/EP2019/084256
§ 371 (c)(1),
(2) Date: Jun. 9, 2021

(87) PCT Pub. No.: WO2020/120406
PCT Pub. Date: Jun. 18, 2020

(65) Prior Publication Data
US 2022/0017943 A1    Jan. 20, 2022

(30) Foreign Application Priority Data
Dec. 10, 2018 (GB) .................... 1820095

(51) Int. Cl.
*C12Q 1/48* (2006.01)
*C12Q 1/34* (2006.01)

(52) U.S. Cl.
CPC ............... *C12Q 1/48* (2013.01); *C12Q 1/34* (2013.01); *G01N 2333/91142* (2013.01); *G01N 2333/978* (2013.01)

(58) Field of Classification Search
None
See application file for complete search history.

(56) References Cited

U.S. PATENT DOCUMENTS

| 2005/0101571 A1 | 5/2005 | Jolivet |
| 2022/0017900 A1 | 1/2022 | Kaser et al. |

FOREIGN PATENT DOCUMENTS

| CA | 2005205 A1 | 6/1990 |
| CA | 3019628 A1 | 10/2017 |
| WO | 2020/120410 A1 | 6/2020 |

OTHER PUBLICATIONS

International Search Report and Written Opinion for PCT/EP2019/084256, entitled "FAMIN Assay Methods", issued on Feb. 28, 2020.
Cader, M. Zaeem et al., C13orf31 (FAMIN) is a central regulator of immunometabolic function, Nature Immunology, vol. 17, No. 9, Aug. 1, 2016 (Aug. 1, 2016), pp. 1046-1056.
Cader, M. Zaeem et al., FAMIN Is a Multifunctional Purine Enzyme Enabling the Purine Nucleotide Cycle, Cell, Elsevier, Amsterdam, NL, vol. 180, No. 2, Jan. 23, 2020 (Jan. 23, 2020), p. 278.
Moriwaki, Y. et al., Enzymes involved in purine metabolism—A review of histochemical localization and functional Implications, Histology and Histopathology: Cellular and Molecular Biology, Gutenberg, ES, vol. 14, No. 4, Oct. 1, 1999 (Oct. 1, 1999), pp. 1321-1340.
Wakil, Salma M. et al., Association of a Mutation in LACC1 With a Monogenic Form of Systemic Juvenile Idiopathic Arthritis: Monogenic Systemic Juvenile Idiopathic Arthritis, Arthritis & Rheumatology (Hoboken), vol. 67, No. 1, Dec. 27, 2014 (Dec. 27, 2014), pp. 288-295.
International Search Report and Written Opinion for PCT/EP2019/084265, entitled "Methods of Cancer Treatment", issued on Apr. 9, 2020.
Cader, M. Zaeem et al., C13orf31 (FAMIN) is a central regulator of immunometabolic function, Nature Immunology, vol. 17, No. 9, Sep. 1, 2016 (Aug. 1, 2016), pp. 1046-1056.
O'Neill, et al. "Immunometabolism governs dendritic cell and macrophage function" J. Exp. Med. 2016 vol. 213 No. 1 15-23.
Prosser, et al. "Metabolomic strategies for the identification of new enzyme functions and metabolic pathways" EMBO Reports (2014) 15, 657-669.
Zhao, et al. "Discovery of new enzymes and metabolic pathways using structure and genome context" Nature. Oct. 31, 2013;502(7473):698-702. doi: 10.1038/nature12576. Epub Sep. 22, 2013. PMID: 24056934; PMCID: PMC3966649.
Folch, et al. "A simple method for the isolation and purification of total lipides from animal tissues" J Biol Chem. May 1957;226(1):497-509. PMID: 13428781.
Gorshkov, et al. "Polyphenol oxidase from Pectobacterium atrosepticum: identification and cloning of gene and characteristics of the enzyme." Journal of basic microbiology 57.12 (2017): 998-1009.
Landgraf, et al. "Radical S-Adenosylmethionine Enzymes in Human Health and Disease" Annu. Rev. Biochem. 2016. 85:485-514.
Camici, et al. "Interplay between adenylate metabolizing enzymes and AMP-activated protein kinase." The FEBS Journal 285 (2018): 3337-3352.
Gizzi, et al. "A naturally occurring antiviral ribonucleotide encoded by the human genome" Nature. Jun. 2018;558 (7711):610-614.
Assadi, et al. "Functional Analyses of the Crohn's Disease Risk Gene LACC1" PLOS ONE 11(12): e0168276 (2016).

(Continued)

*Primary Examiner* — Robert J Yamasaki
*Assistant Examiner* — Charles Zoltan Constantine
(74) *Attorney, Agent, or Firm* — HAMILTON, BROOK, SMITH & REYNOLDS, P.C.

(57) ABSTRACT

This invention relates to the finding that FAMIN (fatty acid metabolism-immunity nexus; LACC1, C13orf31)) is a tri-functional purine salvage enzyme that displays a unique combination of adenosine deaminase, purine nucleoside phosphorylase and methylthioadenosine phosphorylase activities. Methods of measuring FAMIN activity and screening for FAMIN modulators are provided that comprise determining the adenosine deaminase activity, purine nucleoside phosphorylase activity and/or methylthioadenosine phosphorylase activity of an isolated FAMIN protein.

39 Claims, 52 Drawing Sheets
Specification includes a Sequence Listing.

(56) References Cited

OTHER PUBLICATIONS

Lindley, et al. "Demonstration of adenosine deaminase activity in human fibroblast lysosomes" Biochem J. Mar. 1, 1993;290 (Pt 2):457-62.
Boison "Adenosine Kinase: Exploitation for Therapeutic Gain" Pharmacol Rev. Apr. 16, 2013;65(3):906-43.
Camici, et al. "The Inside Story of Adenosine" Int. J. Mol. Sci. 2018; 19(3):784.
Beloqui, et al. "Novel Polyphenol Oxidase Mined from a Metagenome Expression Library of Bovine Rumen: Biochemical Properties, Structural Analysis, and Phylogenetic Relationships" Journal of Biological Chemistry, vol. 281, No. 32, 2006, 22933-22942.
Perna, et al. "Multiple Reaction Monitoring for quantitative laccase kinetics by LC-MS" Sci Rep 8, 8114 (2018).
Albers "Metabolic Characteristics and Importance of the Universal Methionine Salvage Pathway Recycling Methionine from 5'-Methylthioadenosine" IUBMB Life. Dec. 2009;61(12):1132-42.
Kryukov, et al. "MTAP deletion confers enhanced dependency on the arginine methyltransferase PRMT5 in human cancer cells" Science. Mar. 11, 2016;351(6278):1214-8.
Friedkin, et al. The Enzymes, P. D. Boyer, H. Lardy, K. Myrback, Eds. (Academic Press, New York, 1961), vol. 5, pp. 245.
Zimmerman, et al. "Adenine as Substrate for Purine Nucleoside Phosphorylase" Can. J. Biochem. 49, 1050-1054 (1971).
Maynes, et al. "Design of an adenosine phosphorylase by active-site modification of murine purine nucleoside phosphorylase" Biochem. J. 344 Pt 2, 585-592 (1999).
Murray "The Biological Significance of Purine Salvage" Annu. Rev. Biochem. 40, 811 (1971).
Ashihara, et al. "Purine salvage in plants" Phytochemistry 147, 89-124 (2018).
Bzowska, et al. "Purine nucleoside phosphorylases: properties, functions, and clinical aspects" Pharmacol. Ther. 88, 349-425 (2000).
Della Ragione, et al. "Purification and Characterization of Recombinant Human 59-Methylthioadenosine Phosphorylase: Definite Identification of Coding cDNA" Biochem. Biophys. Res. Commun. 223, 514-519 (1996).
Canas, et al. "Laccases and their natural mediators: Biotechnological tools for sustainable eco-friendly processes" Biotechnol. Adv. 28, 694-705 (2010).
Kim, et al. "Crystal Structure of Hypothetical Protein YfiH From Shigella flexneri at 2 Å Resolution" Proteins 63, 1097-1101 (2006).
Holm, et al. "An Evolutionary Treasure: Unification of a Broad Set of Amidohydrolases Related to Urease" Proteins 28, 72-82 (1997).
Wilson, et al. "Atomic Structure of Adenosine Deaminase Complexed with a Transition-State Analog: Understanding Catalysis and Immunodeficiency Mutations" Science 252, 1278-1284 (1991).
Jabri, et al. "The Crystal Structure of Urease from Klebsiella aerogenes" Science 268, 998-1004 (1995).
Bradford, et al. "Adenosine Deaminase (ADA)-Deficient Severe Combined Immune Deficiency (SCID): Molecular Pathogenesis and Clinical Manifestations" J. Clin. Immunol. 37, 626-637 (2017).
Giblett, et al. "Nucleoside-Phosphorylase Deficiency in a Child With Severely Defective T-Cell Immunity and Normal B-Cell Immunity" Lancet 1, 1010-1013 (1975).
Giblett, et al. "Adenosine-Deaminase Deficiency in Two Patients With Severely Impaired Cellular Immunity" Lancet 2, 1067-1069 (1972).
Mavrakis, et al. "Disordered methionine metabolism in MTAP/CDKN2A-deleted cancers leads to dependence on PRMT5" Science 351, 1208-1213 (2016).
Nobori, et al. "Genomic Cloning of Methylthioadenosine Phosphorylase: A Purine Metabolic Enzyme Deficient in Multiple Different Cancers" Proc. Natl. Acad. Sci. U.S.A. 93, 6203 (1996).
Chen, et al. "Gene Deletion Chemoselectivity: Codeletion of the Genes for p16INK4, Methylthioadenosine Phosphorylase, and the α- and β-Interferons in Human Pancreatic Cell Carcinoma Lines and Its Implications for Chemotherapy" Cancer Res. 56, 1083-1090 (1996).
Aartsma-Rus et al., 2009, "Guidelines for Antisense Oligonucleotide Design and Insight Into Splice-modulating Mechanisms", Molecular Therapy, vol. 17, No. 3, p. 548-553 (Year: 2009).
Cader et al., Sep. 2016, "C13orf31 (FAMIN) is a central regulator of immunometabolic function", Nature Immunology, vol. 17, No. 9, p. 1046-1060 (Year: 2016).
Dang et al., Sep. 29, 2018, "New insights into molecular mechanisms of rosiglitazone in monotherapy or combination therapy against cancers", Chemico-Biological Interactions, 296 (2018), p. 162-170 (Year: 2018).
De Souza, et al., 2006, "Transcriptional and phenotypic comparisons of Ppara knockout and siRNA knockdown mice", Nucleic Acids Research, vol. 34, No. 16, p. 4486-4494 (Year: 2006).
Lahiri et al., Jun. 8, 2017, "Human LACC1 increases innate receptor-induced responses and a LACC1 disease-risk variant modulates these outcomes", Nature Communications, 8:151614, DOI: 10.1038/ncomms15614 (Year: 2017).
Nakajima et al., 2015, "Adenosine Deaminase Inhibitor EHNA Exhibits a Potent Anticancer Effect Against Malignant Pleural Mesothelioma", Cellular Physiology and Biochemistry, 2015;35:51-60 (Year: 2015).
Non-Final Office Action for U.S. Appl. No. 17/312,362 mailed Dec. 31, 2024.
Reynolds et al., 2012, "A Phase III trial of fludarabine, cyclophosphamide, and rituximab vs. pentostatin, cyclophosphamide, and rituximab in B-cell chronic lymphocytic leukemia", Invest New Drugs, (2012) 30: 1232-1240 (Year: 2012).
Samudio et al., 2010, "Pharmacologic inhibition of fatty acid oxidation sensitizes human leukemia cells to apoptosis induction", J Clin Invest. 120(1): 142-156 (Year: 2010).
Skon-Hegg et al., Dec. 3, 2018, "LACC1 Regulates TNF and IL-17 in Mouse Models of Arthritis and Inflammation", The Journal of Immunology, 1;202(1): 181-193 (Year: 2018).

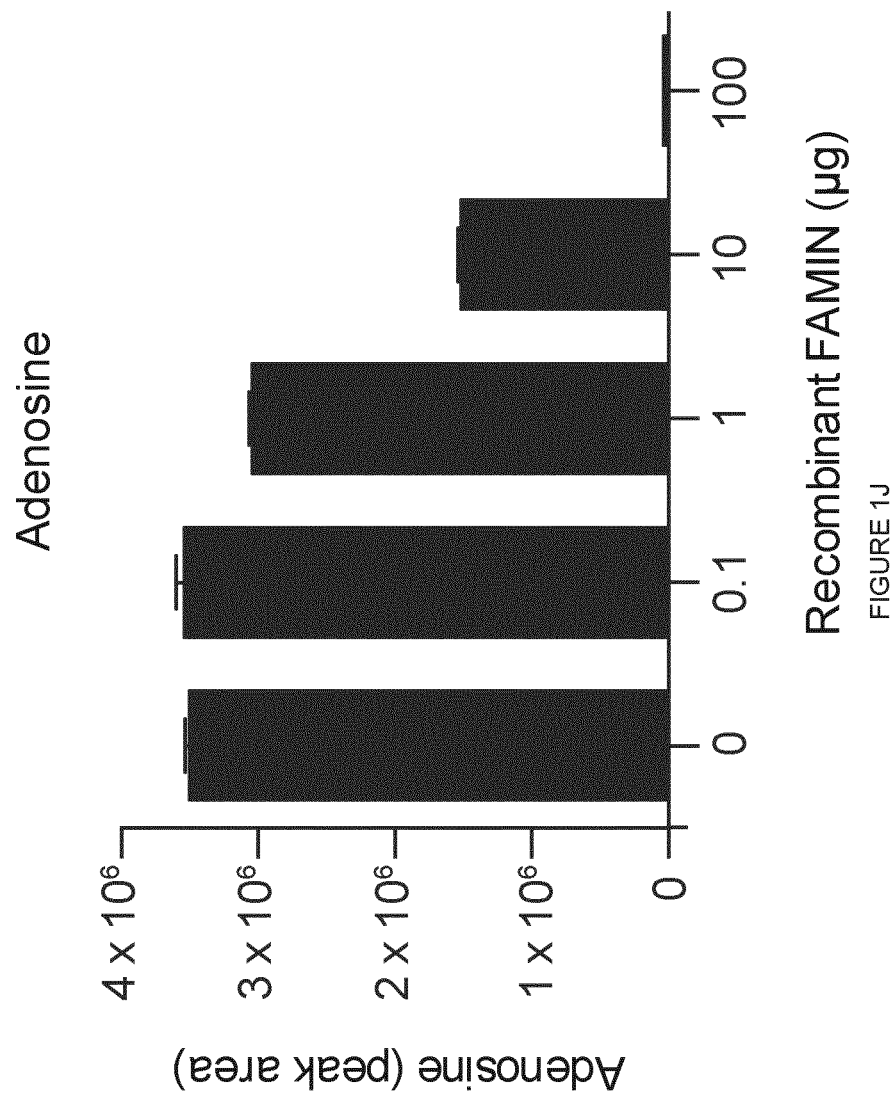

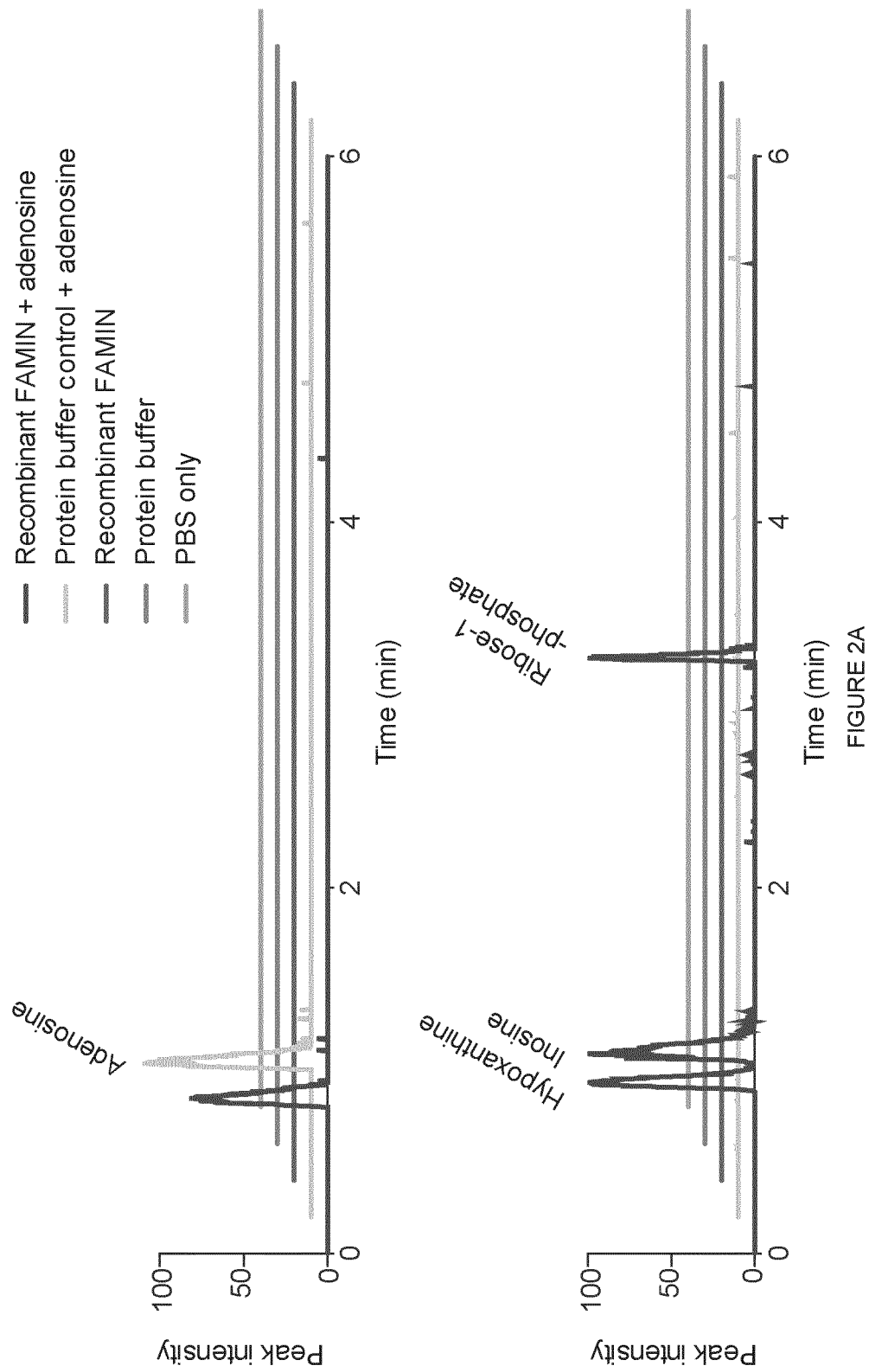

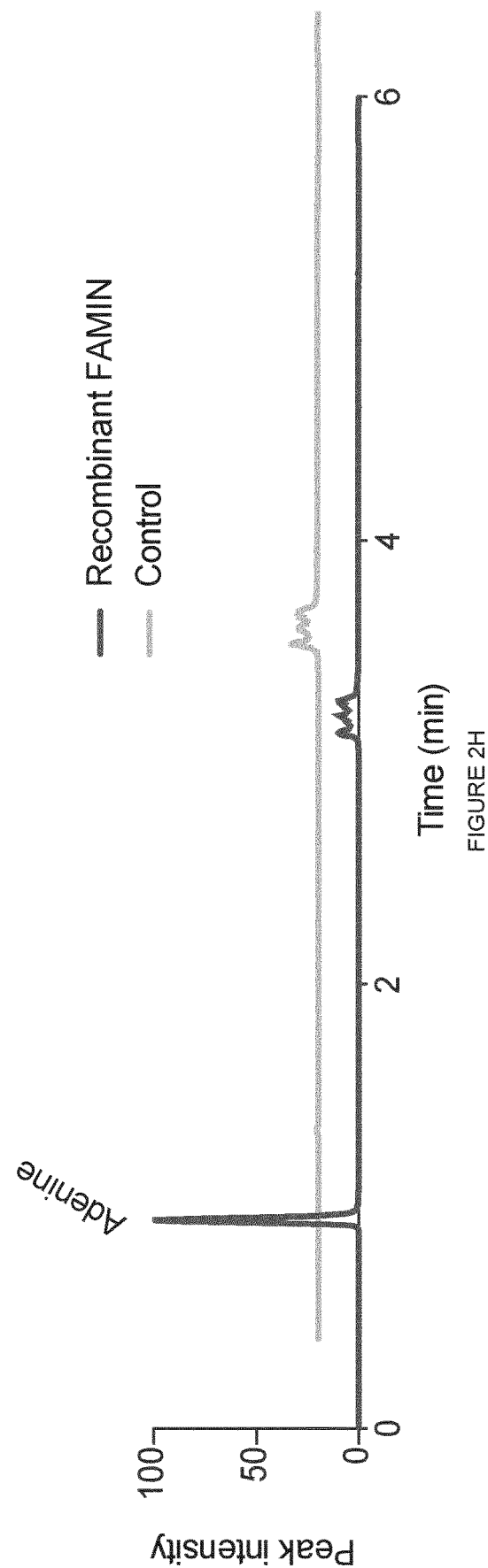

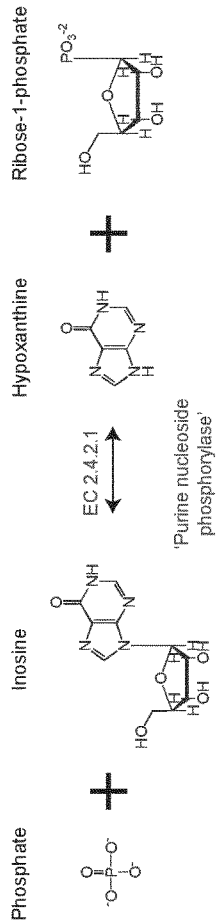
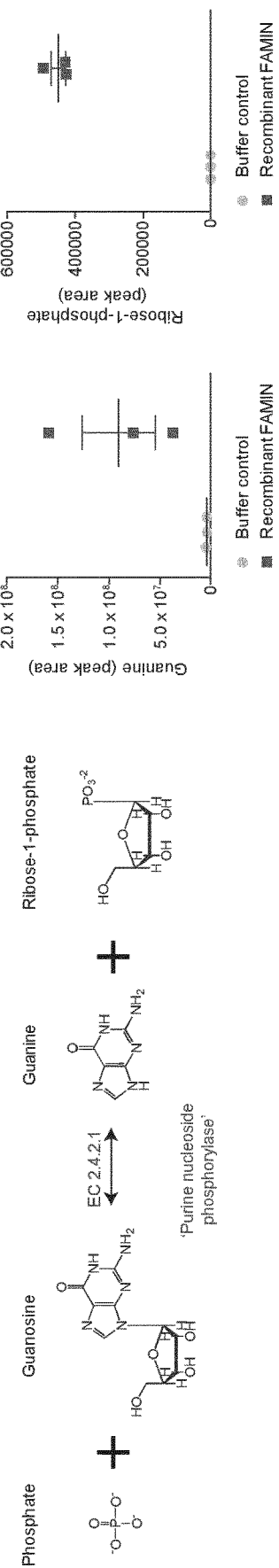
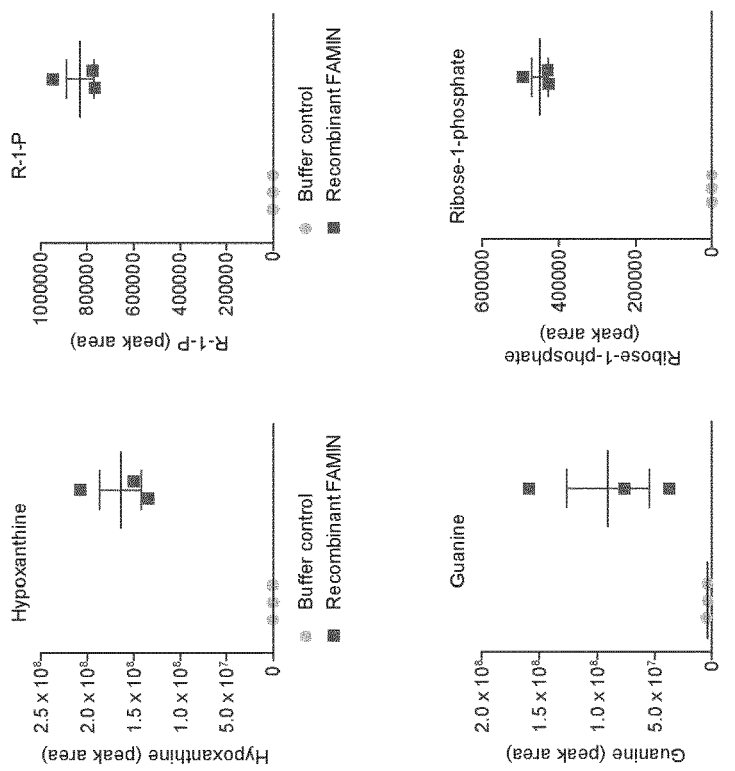
FIGURE 2P
FIGURE 2Q

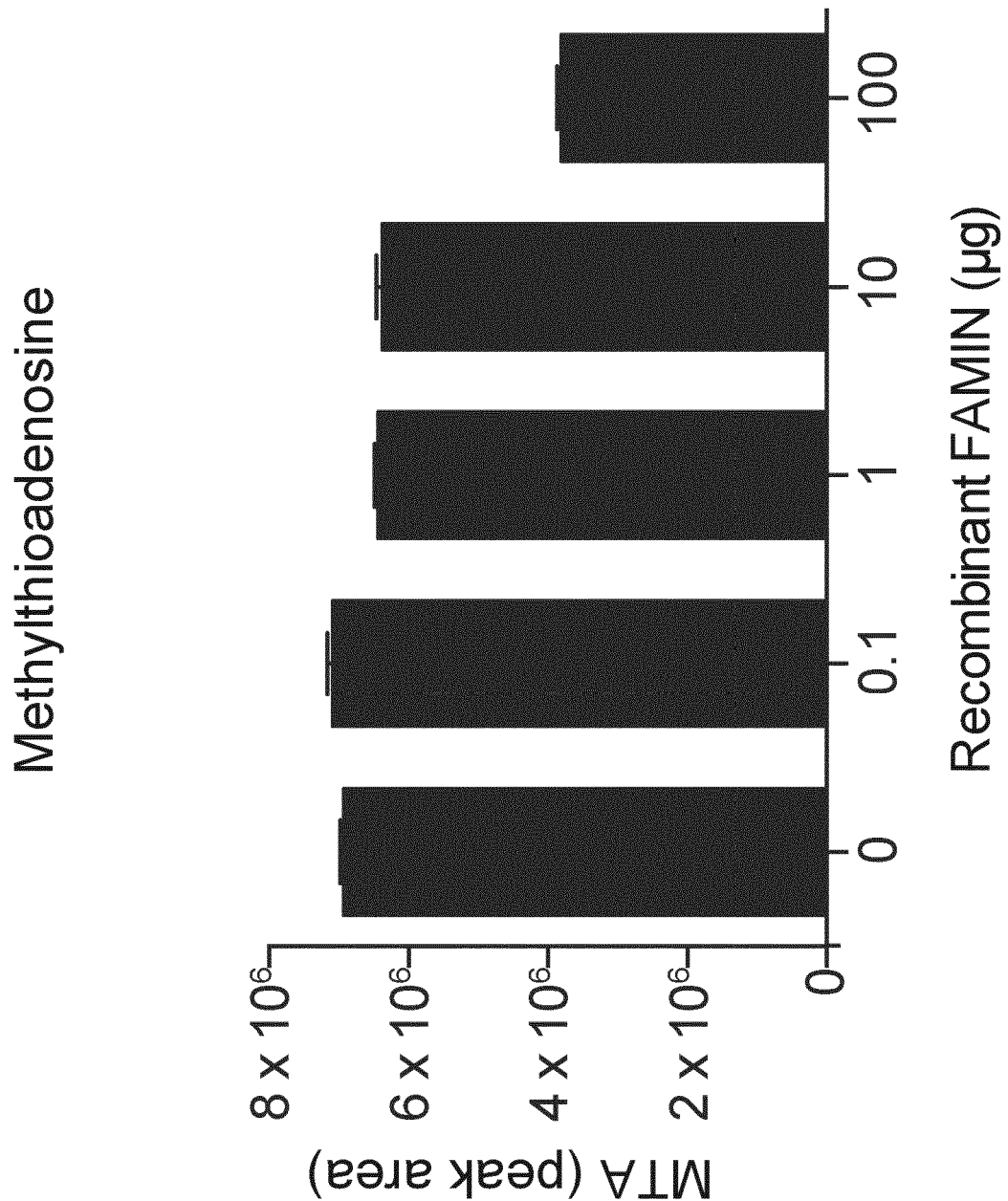

SEQUENCE LISTING

<160> NUMBER OF SEQ ID NOS: 2

<210> SEQ ID NO 1
<211> LENGTH: 430
<212> TYPE: PRT
<213> ORGANISM: Homo sapiens

<400> SEQUENCE: 1

Met Ala Glu Ala Val Leu Ile Asp Leu Phe Gly Leu Lys Leu Asn Ser
1               5                   10                  15

Gln Lys Asn Cys His Gln Thr Leu Leu Lys Thr Leu Asn Ala Val Gln
            20                  25                  30

-continued

Tyr His His Ala Ala Lys Ala Lys Phe Leu Cys Ile Met Cys Cys Ser
         35                  40                  45

Asn Ile Ser Tyr Glu Arg Asp Gly Glu Gln Asp Asn Cys Glu Ile Glu
50                  55                  60

Thr Ser Asn Gly Leu Ser Ala Leu Leu Glu Glu Phe Glu Ile Val Ser
65                  70                  75                  80

Cys Pro Ser Met Ala Ala Thr Leu Tyr Thr Ile Lys Gln Lys Ile Asp
                 85                  90                  95

Glu Lys Asn Leu Ser Ser Ile Lys Val Ile Val Pro Arg His Arg Lys
                100                 105                 110

Thr Leu Met Lys Ala Phe Ile Asp Gln Leu Phe Thr Asp Val Tyr Asn
            115                 120                 125

Phe Glu Phe Glu Asp Leu Gln Val Thr Phe Arg Gly Gly Leu Phe Lys
        130                 135                 140

Gln Ser Ile Glu Ile Asn Val Ile Thr Ala Gln Glu Leu Arg Gly Ile
145                 150                 155                 160

Gln Asn Glu Ile Glu Thr Phe Leu Arg Ser Leu Pro Ala Leu Arg Gly
                165                 170                 175

Lys Leu Thr Ile Ile Thr Ser Ser Leu Ile Pro Asp Ile Phe Ile His
            180                 185                 190

Gly Phe Thr Thr Arg Thr Gly Gly Ile Ser Tyr Ile Pro Thr Leu Ser
        195                 200                 205

Ser Phe Asn Leu Phe Ser Ser Ser Lys Arg Arg Asp Pro Lys Val Val
210                 215                 220

Val Gln Glu Asn Leu Arg Arg Leu Ala Asn Ala Ala Gly Phe Asn Val
225                 230                 235                 240

Glu Lys Phe Tyr Arg Ile Lys Thr His His Ser Asn Asp Ile Trp Ile
                245                 250                 255

Met Gly Arg Lys Glu Pro Asp Ser Tyr Asp Gly Ile Thr Thr Asn Gln
            260                 265                 270

Arg Gly Val Thr Ile Ala Ala Leu Gly Ala Asp Cys Ile Pro Ile Val
        275                 280                 285

Phe Ala Asp Pro Val Lys Lys Ala Cys Gly Val Ala His Ala Gly Trp
290                 295                 300

Lys Gly Thr Leu Leu Gly Val Ala Met Ala Thr Val Asn Ala Met Ile
305                 310                 315                 320

Ala Glu Tyr Gly Cys Ser Leu Glu Asp Ile Val Val Leu Gly Pro
                325                 330                 335

Ser Val Gly Pro Cys Cys Phe Thr Leu Pro Arg Glu Ser Ala Glu Ala
            340                 345                 350

Phe His Asn Leu His Pro Ala Cys Val Gln Leu Phe Asp Ser Pro Asn
        355                 360                 365

Pro Cys Ile Asp Ile Arg Lys Ala Thr Arg Ile Leu Leu Glu Gln Gly
370                 375                 380

Gly Ile Leu Pro Gln Asn Ile Gln Asp Gln Asn Gln Asp Leu Asn Leu
385                 390                 395                 400

Cys Thr Ser Cys His Pro Asp Lys Phe Phe Ser His Val Arg Asp Gly
                405                 410                 415

Leu Asn Phe Gly Thr Gln Ile Gly Phe Ile Ser Ile Lys Glu
            420                 425                 430

<210> SEQ ID NO 2
<211> LENGTH: 4288
<212> TYPE: DNA

<213> ORGANISM: Homo sapiens

<400> SEQUENCE: 2

| | | | | | |
|---|---|---|---|---|---|
| agacctgcag | ctcctgccgc | cctgcgcccg | ctcccagggc | ccgtcgttcc | gccgccctat | 60 |
| ccctcctcaa | ggggcccta | gctgcctcct | cgcgacccct | tccggactcg | gcctgcccac | 120 |
| tcctgcccgc | taacccgcct | ggctcccggg | cgagagccct | cgcgcggctc | tggttcctgt | 180 |
| tcctctaacg | ccgccgggc | tgcgggatgc | cgactccgcg | gaccgcccag | acccggaact | 240 |
| gctgaggcag | cagcgggctc | gcggcgcttg | gctcatcccg | ggattcccca | gctctcgcgc | 300 |
| tgggcccgcc | gcgttcgcac | caagcacgcc | aggcggccct | ggcctacctc | cctcccgcct | 360 |
| cccggcagct | ggcacgaggg | aacctggccg | tcaggtttcc | cctgggatcc | tgggacggta | 420 |
| tcaggcgggg | aatctgtgcg | gccgcggcga | ggtgatttat | ttggcataaa | agtattcttt | 480 |
| caaggatggc | agaagctgtt | ttgattgatc | ttttggttt | gaaattgaac | tctcaaaaaa | 540 |
| actgccatca | gacattactg | aagactttga | atgctgtcca | ataccaccat | gctgccaagg | 600 |
| ccaagtttct | ctgtataatg | tgttgcagta | acatcagcta | tgaaagggat | ggagaacaag | 660 |
| ataattgtga | atagaaaca | agcaatggat | tatcagctct | cttggaagaa | tttgagattg | 720 |
| ttagctgtcc | cagcatggct | gccactttgt | ataccattaa | acagaaaatt | gatgaaaaaa | 780 |
| atctgagcag | cattaaggta | attgtaccca | ggcacaggaa | gacattaatg | aaagcttta | 840 |
| ttgatcaact | cttcactgat | gtttacaatt | ttgaatttga | agatttgcaa | gtgacttta | 900 |
| ggggagggct | ttttaaacag | tccattgaaa | taaacgtaat | cacagctcaa | gaactaagag | 960 |
| gaattcagaa | tgaaatagaa | acattttga | gaagtctgcc | agcactgaga | ggaaaattaa | 1020 |
| ctattatcac | ttcttctttg | atcccagata | ttttcataca | tggatttact | acaagaacag | 1080 |
| gtgggatatc | ttatatacca | actcttagct | cattcaatct | cttcagtagt | tccaaacgga | 1140 |
| gagatcccaa | ggtagtggtt | caagaaaatc | tgcgtaggtt | ggcgaatgct | gcaggattta | 1200 |
| atgtggagaa | attttaccga | ataaagactc | atcattccaa | tgacatctgg | attatgggaa | 1260 |
| gaaaggagcc | tgactcttat | gatggaataa | ccacaaatca | gagaggagtc | acaatagcag | 1320 |
| ctcttggtgc | agactgtata | ccgatagttt | ttgcagatcc | agtcaaaaaa | gcatgtgggg | 1380 |
| ttgctcacgc | tggttggaaa | ggtactttgt | tgggtgttgc | tatggctaca | gtgaatgcta | 1440 |
| tgatagcaga | atatgctgc | agtttggaag | acattgttgt | tgtacttgga | ccttcagtag | 1500 |
| gaccttgctg | ttttactctt | ccaagggaat | cagcagaggc | atttcataat | cttcatcctg | 1560 |
| catgtgtaca | actatttgat | tcaccaaatc | cctgtatcga | catccgtaaa | gccacaagga | 1620 |
| ttcttctaga | acagggagga | attcttccac | agaatattca | ggaccagaac | caagatctca | 1680 |
| acctctgtac | atcttgccat | cctgacaagt | ttttctccca | tgtccgagat | ggccttaatt | 1740 |
| ttggtacaca | gattggcttc | atatcaatta | aagaatgaga | tacttgactg | gattttgta | 1800 |
| taactgcttc | ctgcctcctt | ccaaactgac | tgcaagagag | aaatttagct | gttttgattta | 1860 |
| cttaaaacca | aatggattac | aatggataat | tcatcttttg | ggtatatttt | tactattatt | 1920 |
| caaagccaaa | tgattttcat | ttaattgtaa | taataactga | caaaaatcag | tatgttgtag | 1980 |
| ctaatatgtt | ttatgcatga | gaattattct | taaagtttgt | tctccctgtt | tattacacag | 2040 |
| atcaggaata | gatttgttca | gttcagtatt | tattggatac | cctctattgg | tcaggcattg | 2100 |
| tgttaagcat | atgtgaatca | aaatgaacac | aacttttcc | tttgagtctg | atacagtgaa | 2160 |
| ggagataaac | acttctacaa | cttaaattta | attttaatag | cagtgaagaa | gaacataagg | 2220 |
| aatagaggtt | aattttaccc | agaagcagga | tagagaaaat | attacagaga | aaatcacata | 2280 |

```
tcacatgggc tcgaaagatg tagaggtttt tgacaaatga agaacaacca taacaggtag    2340
agggaacacc atgaaccagg gcatgaaact gaaagtgcat aacatattct agagagagaa    2400
gggtgtgggc atgagttagg gctggaaaaa caggttggaa acagataagt aagggtctca    2460
aatgcaatgt caaagagctt gcagtttatt ttccaggcaa tgagtaggca gccaaaaaaa    2520
aaaaagtaag gatgttttt tttttttcc catggcatca tatttaagag gatggattta     2580
aattgtgtga gaccaaagca tagagactag ataagaggcg atcaaaatat ttcaaaagaa    2640
aataatgaag atccaatgaa ggaagtggaa attaaaatag gaagagagt agatggatta    2700 gagagacatt taagagatgg aatcaataga tcctgttact agataatgga agtaagaggt    2760
gaggaagagt ggaaaagtca ttaatgactc taagatttct gcttggctgc ttaccaagat    2820
tggcaacaaa gggagggaga aggtttgaa aaagagagaa ggataatgag tttgacttta    2880
catagaatga agggcatcca gatagaaatc tttggttaat aattagaaat atagacctag    2940
aaattaggag gaaacctgag acagagacaa atatttcaaa gcttacaata cagagatgat    3000
acctgattct attggagcag gtttgatcat ctaggcagaa attaggatga gaaaaaagga    3060
gatccaataa tacaacctta tagtcacaga agtaagaaaa aagggtagt tgttttgaag     3120 aagccaggat aggtgtggaa agtactcaaa agaaatctt cagggataaa ataaagtgat    3180
aatttaaaag aaatcaatgg attaaacata ttgaaactgt tctataggca gtggtcattg    3240
agtcagcttt cagtgcatta ggaagaagat gcataggtgt caactcttt ctgacagcat    3300 ttactagaga agagaaaaag ctggggacta catcttcaag gaagggactt ttttggatg    3360 agcagttttg agtgtgtttg tcagttaaag agaggaatta ggttagtttt catttgggaa    3420
aaattgtata tatattaat gtaagttatc acattgcatc ttaaaatat tcttatttaa    3480 tacatatatt tcctacatgt atatgtggta gcatgatagc aaataacatt tgtttggtat    3540
ttccaaagga ctttcatgta cattgcctca ttttacctt acagctactc tgaaatacac    3600
aggcattatc cctttattc agctgagaaa actgagcttc attgaggtgg aggtcaaaaa    3660
tcacaaaatt tgtgatgaat taagatttga acatatgttt tgtgactcca gttttccttt    3720
cagattttaa aattaattaa agggatcttc attatacttt tattgttaac tttttgttaa    3780
cataatttat tcatacattc agtgaaaatt ttgttgaggt actgggacag gttaaaaaat    3840
acagttgtag ccctcaggat atttaatatc cagtgaaaag tgacagtcag taaaccaaca    3900
atctcaatac tttgatatat gttgtgaggt tgtgataacc gattcttgtt tagtttaatt    3960
ctatatctcc cttagaccag tgttaaattt aaataaaaca cctcattttt tccaattcag    4020
ggaaggcact aaacataaag cataggatag aaatgttgaa ctcatccaaa atattatttt    4080
gtttaatgaa aatgatgaag attaaggaat acttccatgt attgagtaag gttgataatt    4140
ttctaattct tcactgtgca ttatttgtt tgaagttggt aaatttggag tatcctgcag    4200
acacattttg ctttatgtac tacaacattc tacaaccaaa taaaattat tttgattatc    4260 tgaaaaaaaa aaaaaaaaaa aaaaaaaa                                       4288
```

FAMIN ASSAY METHODS

This application is the U.S. National Stage of International Application No. PCT/EP2019/084256, filed Dec. 9, 2019, which designates the U.S., published in English, and claims priority under 35 U.S.C. § 119 or 365 (c) to GB Application No. 1820095.6, filed Dec. 10, 2018. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 55591003002_CORRECTEDSEQUENCE-LISTING.txt; created Jun. 25, 2021, 9 KB in size.

FIELD

The present invention relates to assays for determining FAMIN protein activity and methods of screening for compounds that modulate FAMIN protein activity.

BACKGROUND

The gene encoding fatty acid metabolism-immunity nexus (FAMIN; LACC1, C13orf31) is strongly linked to human disease. Highly penetrant mutations cause juvenile idiopathic arthritis (JIA), a spiking fever with rash and arthritis known as Still's disease, or early-onset inflammatory bowel disease. A common coding polymorphism, I254V, carried by ~⅓ of the world's population increases risk for Crohn's disease (CD), an inflammatory bowel disease, and susceptibility to leprosy, a chronic infection with *Mycobacterium leprae*.

FAMIN, a 430 amino acid protein, has no domains with any reported biochemical function. FAMIN-deficient macrophages, however, are immunologically and metabolically compromised, irrespective of whether they rely on aerobic glycolysis or oxidative phosphorylation (1, 2).

Identifying the biochemical function of orphan proteins, such as FAMIN, is a formidable challenge (3, 4).

SUMMARY

The present inventors have unexpectedly found that FAMIN (fatty acid metabolism-immunity nexus) is a trifunctional purine salvage enzyme that displays a unique combination of adenosine deaminase, purine nucleoside phosphorylase and methylthioadenosine phosphorylase activities. In addition, the purine nucleoside phosphorylase activity of FAMIN was surprisingly found to include a unique adenosine phosphorylase activity not present in other mammalian purine nucleoside phosphorylases, and such activity has been considered absent from eukaryotic cells. Assay methods and methods of screening for FAMIN modulators have been developed based on these findings.

A first aspect of the invention provides a method of measuring the activity of a FAMIN protein comprising:
providing an isolated FAMIN protein; and
determining the adenosine deaminase activity, purine nucleoside phosphorylase activity and/or methylthioadenosine phosphorylase activity of the isolated FAMIN protein.

A second aspect of the invention provides a method of screening for a compound that modulates the activity of a FAMIN protein comprising:
determining the adenosine deaminase activity, purine nucleoside phosphorylase activity and/or methylthioadenosine phosphorylase activity of an isolated FAMIN protein in the presence and absence of a test compound.

A difference in the adenosine deaminase activity, purine nucleoside phosphorylase activity and/or methylthioadenosine phosphorylase activity of the FAMIN protein in the presence relative to the absence of test compound is indicative that the test compound modulates the activity of the FAMIN protein. A decrease in the adenosine deaminase activity, purine nucleoside phosphorylase activity and/or methylthioadenosine phosphorylase activity of the FAMIN protein in the presence relative to the absence of test compound may be indicative that the test compound is a FAMIN inhibitor. An increase in the adenosine deaminase activity, purine nucleoside phosphorylase activity and/or methylthioadenosine phosphorylase activity of the FAMIN protein in the presence relative to the absence of test compound may be indicative that the test compound is a FAMIN potentiator.

A method of the first or second aspects may comprise determining the adenosine deaminase activity of the FAMIN protein. The adenosine deaminase activity of the FAMIN protein may be determined by measuring the conversion of an adenosine molecule into an inosine molecule in the presence of the FAMIN protein.

A method of the first or second aspects may comprise determining the purine nucleoside phosphorylase activity of the FAMIN protein. The purine nucleoside phosphorylase activity of the FAMIN protein may be determined by measuring the conversion of a purine nucleoside into a nucleobase and a ribose-1-phosphate molecule in the presence of the FAMIN protein; or the conversion of a nucleobase and a ribose-1-phosphate molecule into a purine nucleoside in the presence of the FAMIN protein.

The purine nucleoside phosphorylase activity of the FAMIN protein may include adenosine phosphorylase activity. In some preferred embodiments, a method of the first or second aspects may comprise determining the adenosine phosphorylase activity of the FAMIN protein. The adenosine phosphorylase activity of the FAMIN protein may be determined by measuring the conversion of adenosine into adenine and ribose-1-phosphate molecule in the presence of the FAMIN protein; or the conversion of adenine and a ribose-1-phosphate molecule into adenosine in the presence of the FAMIN protein.

A method of the first or second aspects may comprise determining the methylthioadenosine phosphorylase activity of the FAMIN protein. The methylthioadenosine phosphorylase activity of the FAMIN protein may be determined by measuring the conversion of methylthioadenosine into adenine and a S-methyl-5'-thioribose-1-phosphate molecule in the presence of the FAMIN protein; or the conversion of adenine and a S-methyl-5'-thioribose-1-phosphate molecule into methylthioadenosine in the presence of the FAMIN protein.

Other aspects and embodiments of the invention are described in more detail below.

BRIEF DESCRIPTION OF THE FIGURES

FIG. 1 shows that FAMIN is a purine nucleoside metabolising enzyme. FIG. 1J shows abundance of adenosine within the library after incubation with 0.1, 1.0, 10.0 or 100.0 µg of recombinant FAMIN or protein buffer control (1 h, 37° C., PBS; n=3, mean±S.E.M.). *P<0.05 and **P<0.01 (unpaired, two-tailed Student's t-test). Data are representative of at least 3 independent experiments.

FIG. 2 shows that FAMIN has adenosine deaminase, purine nucleoside phosphorylase and S-methyl-5'-thioadenosine phosphorylase activities. FIG. 2A shows representative extracted chromatograms for adenosine (upper chromatogram) and inosine, hypoxanthine, ribose-1-phosphate (lower chromatogram) following incubation of 10 µg recombinant FAMIN or appropriate control with 100 µM adenosine for 1 h at 37° C. in 100 µl phosphate-buffered saline (PBS). Peak intensity of each extracted chromatogram per given m/z value normalised to maximum level of 100. Controls as indicated include reaction buffer (PBS), protein elution buffer as described in methods, recombinant FAMIN without substrate or protein buffer with adenosine substrate. FIG. 2H shows representative extracted chromatograms using a modified CSH-C18 method to allow separation and measurement of adenine following incubation of 10 µg recombinant FAMIN or appropriate control with 10 µM adenosine. FIGS. 2P and 2Q show on the left FAMIN catalysed enzymatic reactions. On the right they show levels of guanine or hypoxanthine and ribose-1-phosphate in reactions containing 100 μM guanosine or inosine and recombinant FAMIN or buffer control in 100 μl after 1 h at 37° C. (n=3, mean±S.E.M.). FIG. 2U shows MTA levels following incubation of 0.1, 1.0, 10.0 or 100.0 μg of recombinant FAMIN with the complete metabolomic library (aqueous phase of methanol:chloroform extract of HepG2 cells) in 100 μl PBS (n=3, mean±S.E.M.).

FIG. 4 shows that FAMIN affects levels of purine nucleobases, nucleosides, nucleotides and cofactors in cells.

FIG. 5 shows modulation of FAMIN enzymatic function with small molecules.

DETAILED DESCRIPTION

Figure 1A:
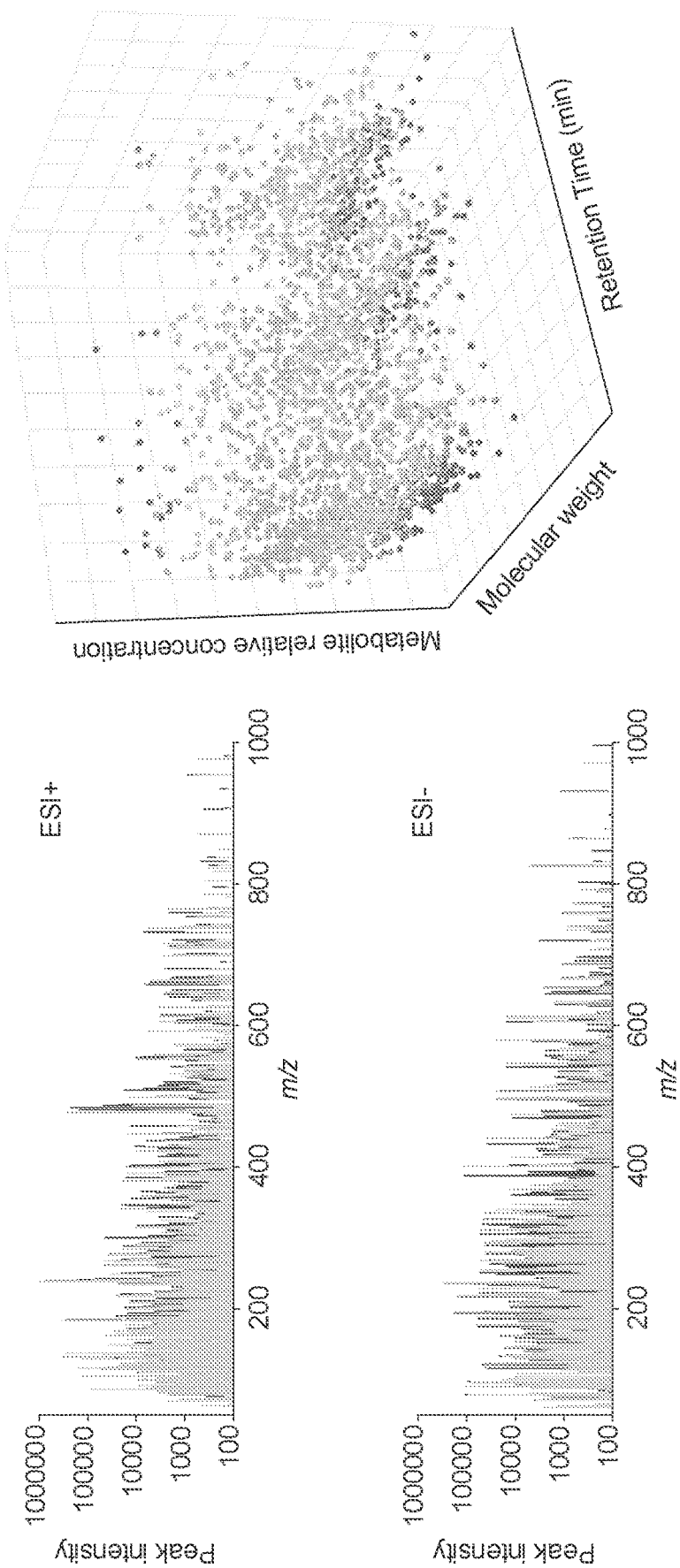
FIG. 1A shows a metabolomic library consisting of the aqueous phase of a methanol:choloroform (Folch) extraction of HepG2 cells 48 h after transfection with FAMIN siRNA. High resolution mass spectrometry in positive and negative electrospray ionisation (ESI) modes coupled to either BEH-amide (HILIC) or C18-pfp chromatography resolved ~25,000 individual features. The left panels show representative total mass spectra, and the right panel shows them separated by molecular weight (m/z), chromatography retention time and relative levels.

This invention relates to the finding that FAMIN (fatty acid metabolism-immunity nexus) has a trifunctional adenosine deaminase, purine nucleoside phosphorylase and methylthioadenosine phosphorylase activity. In addition, the purine nucleoside phosphorylase activity of FAMIN is found to include an adenosine phosphorylase activity that is unique in mammals. Assay methods to determine the activity of the FAMIN protein may comprise measuring one or more of these activities. Methods of screening for modulators of FAMIN protein may comprise measuring one or more of these activities in the presence and absence of test compound.

A FAMIN (fatty acid metabolism-immunity nexus) protein as described herein may be a eukaryotic FAMIN protein, preferably a mammalian FAMIN, such as human FAMIN.

Human FAMIN (also known as LACC1 or C13orf3; Gene ID: 144811) may have the amino acid sequence of NP_001121775.1 (SEQ ID NO: 1) or a variant thereof and may be encoded by the nucleotide sequence of NM_001128303.2 (SEQ ID NO: 2), NM_001350638.1, NM_001350639.1, NM_001350640.1, NM_001350641.1 or NM_001350642.1, or a variant thereof. In some embodiments, a FAMIN protein may comprise amino acids 176-430 (FAMIN$^{\Delta 176}$) of human FAMIN.

In some embodiments, a FAMIN protein may comprise an Ile residue at a position corresponding to position 254 of the amino acid sequence of NP_001121775.1 (SEQ ID NO: 1). In other embodiments, a FAMIN protein may comprise a Val residue at a position corresponding to position 254 of the amino acid sequence of NP_001121775.1 (SEQ ID NO: 1).

A FAMIN protein as described herein may be a prokaryotic FAMIN protein, preferably a bacterial FAMIN. Bacterial FAMIN proteins may include YlmD (Uniprot P84138) from *Geobacillus stearothermophilus* and YfiH (Uniprot P33644) from *Escherichia coli* strain K12.

A FAMIN protein as described herein may comprise or consist of a DUF152 domain (Pfam02578, Cluster of Orthologous Group [COG] 1496). The DUF152 domain of a FAMIN protein may be identified using standard sequence analysis techniques. For example, the DUF152 domain is located in the C terminal portion (amino acids 176-430) of human FAMIN. The DUF152 domain may be responsible for the enzymatic activity of the FAMIN protein and the sequence of the DUF152 domain may be conserved between different FAMIN proteins.

A variant of a FAMIN protein or nucleotide sequence may share at least 50% sequence identity with the wild-type FAMIN amino acid or nucleotide sequence, for example the sequence of human FAMIN or FAMIN$^{\Delta 176}$, at least 55%, at least 60%, at least 65%, at least 70%, at least about 80%, at least 90%, at least 95%, at least 98% or at least 99% sequence identity. Particular amino acid sequence variants may differ from a wild-type FAMIN protein sequence by insertion, addition, substitution or deletion of 1 amino acid, 2, 3, 4, 5, 6, 7, 8, 9, or 10 or more than 10 amino acids.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), the Smith-Waterman algorithm (Smith and Waterman (1981) J. Mol Biol. 147: 195-197), the TBLASTN program, of Altschul et al. (1990) supra, or HMMER (S. R. Eddy. Current Opinion in Structural Biology, 6:361-365, 1996) generally employing default parameters. In particular, the psi-Blast algorithm may be used (Nucl. Acids Res. (1997) 25 3389-3402).

Sequence comparisons are preferably made over the full-length of the relevant sequence described herein.

In some embodiments, the FAMIN protein may be an isolated FAMIN protein, for example a recombinant FAMIN protein.

An isolated FAMIN protein may be free or substantially free of contaminants or material with which it is naturally associated, such as other components of the cells or organelles with which it is found in its natural environment, or the environment in which it is prepared (e.g. cell culture), when such preparation is by recombinant DNA technology practised in vitro or in vivo.

FAMIN protein as described herein may be provided using synthetic or recombinant techniques which are standard in the art. Alternatively, endogenous FAMIN protein may be purified from cells.

A recombinant FAMIN protein may be expressed in insoluble inclusion bodies in a prokaryotic expression system such as *E. coli* and *Lactococcus lactis*. Following expression, the inclusion bodies may be isolated and solubilised with a denaturant to generate the FAMIN protein re-folded into soluble form. Alternatively, a recombinant FAMIN protein may be expressed in a eukaryotic expression system. Suitable eukaryotic host cells include mammalian cells such as CHO and CHO-derived cell lines (Lec cells), HeLa, COS, HEK293, HEK293T, and HEK-EBNA cells, amphibian cells such as *Xenopus* oocytes, insect cells, such as *Trichoplusia ni*, Sf9 and Sf21 and yeast cells, such as *Pichia pastoris*. In some preferred embodiments, recombinant FAMIN protein may be expressed in a mammalian cell line, such as HEK293T.

Recombinant techniques for the expression of proteins are standard in the art. The FAMIN protein may be coupled to a signal leader peptide to direct secretion of the fusion polypeptide from a eukaryotic cell into the culture medium. A range of suitable signal leader peptides are known in the art. The signal leader peptide may be a FAMIN signal sequence or may be heterologous to the FAMIN protein i.e. it may be a non-FAMIN signal sequence. For example, an α-factor secretion signal or BiP signal sequence may be employed. Preferably, the signal peptide is removed by post-translational processing after expression of the FAMIN protein.

The expressed FAMIN protein may be isolated and/or purified, after production. This may be achieved using any convenient method known in the art. Techniques for the purification of recombinant polypeptides are well known in the art and include, for example HPLC, FPLC, size exclusion chromatography or affinity chromatography. In some embodiments, the expressed FAMIN protein may be partially purified before use in an assay method described herein.

In some embodiments, the FAMIN protein may be produced as a fusion protein further comprising an affinity tag, which may, for example, be useful for purification. An affinity tag is a heterologous peptide sequence which forms one member of a specific binding pair. Polypeptides containing the tag may be purified by the binding of the other member of the specific binding pair to the polypeptide, for example in an affinity column. For example, the tag sequence may form an epitope which is bound by an antibody molecule. Suitable affinity tags are well known in the art and are reviewed in Terpe (2003) Appl. Microbiol. Biotechnol. 60 523-533. The affinity tag sequence may be separated from the FAMIN protein after purification, for example, using a site-specific protease.

In some preferred embodiments, recombinant human FAMIN protein with an affinity tag may be expressed in mammalian cells, such as HEK293T cells, and then purified by affinity chromatography followed by tag cleavage and size exclusion chromatography.

In other embodiments, the FAMIN protein may be comprised within a cell extract. Adenosine phosphorylase activity, which is unique to FAMIN in mammalian cells, may be determined in the cell extract. Other purine nucleoside phosphorylase activities, as well as adenosine deaminase and methylthioadenosine phosphorylase activity may be determined in the cell extract relative to a control cell extract and/or in the presence of selective inhibition of other cellular enzymes with the determined activity, such as adenosine deaminase (ADA), methylthioadenosine phosphorylase (MTAP), and purine nucleoside phosphorylase (PNP).

A control cell extract may be obtained from a cell in which FAMIN is inactivated. FAMIN may be inactivated in a control cell by any convenient means, such as RNA silencing using RNAi transfection or gene knock-out. In other embodiments, a control cell extract may be obtained from a cell which expresses a FAMIN-I254V mutant. The adenosine phosphorylase activity of the FAMIN-I254V mutant is selectively inactivated and a control cell extract comprising the FAMIN-I254V mutant may be useful in screening for compounds that have relative selectivity for adenosine phosphorylase activity.

One, two or all three of the adenosine deaminase activity, purine nucleoside phosphorylase activity and/or methylthioadenosine phosphorylase activity of the isolated FAMIN protein may be determined. In some embodiments, these activities may be determined individually, for example to screen for selective inhibitors of an individual activity.

The adenosine deaminase activity of FAMIN converts adenosine nucleosides into inosine nucleosides (EC3.5.4.4). Adenosine deamination activity may be determined by;
  contacting the FAMIN protein with an adenosine nucleoside in a reaction solution; and
  determining the amount of adenosine nucleoside, inosine nucleoside or $NH_3$ in the reaction solution, following said contacting.

Depletion of adenosine nucleoside or generation of $NH_3$ or inosine nucleoside in the reaction solution is indicative of the adenosine deamination activity of the FAMIN protein. The amount of decrease in the concentration of adenosine nucleoside or increase in the concentration of inosine nucleoside in the reaction solution or the amount of $NH_3$ generated may be indicative of the amount of adenosine deamination activity in the reaction solution. Depletion of adenosine nucleoside or the generation of $NH_3$ or the inosine nucleoside in the reaction solution may be determined in the presence relative to the absence of the isolated FAMIN protein.

An adenosine nucleoside may include adenosine or an analogue or derivative thereof. An inosine nucleoside may include inosine or an analogue or derivative thereof.

In some embodiments, the adenosine nucleoside is adenosine (PubChem CID 60961) and the inosine nucleoside is inosine (CID 6021). In other embodiments, the adenosine nucleoside is deoxyadenosine and the inosine nucleoside is deoxyinosine. For example, the adenosine nucleoside may be 2'-deoxyadenosine (CID 13730) and the inosine nucleoside may be 2'-deoxyinosine (CID 65058) or the adenosine nucleoside may be 5'-deoxyadenosine (CID 439182) and the inosine nucleoside may be 5'-deoxyinosine (CID 14693755).

The purine nucleoside phosphorylase activity of FAMIN converts purine nucleosides into purine nucleobases and ribose-1-phosphate molecules in the presence of phosphate (e.g. orthophosphate $PO_4^{3-}$). For example, inosine nucleosides may be converted into hypoxanthine and α-D-ribose-1-phosphate (EC2.4.2.1) and guanosine nucleosides may be converted into guanine and α-D-ribose-1-phosphate (EC2.4.2.15) by the FAMIN protein. In addition, adenosine nucleosides may be converted by a FAMIN protein into adenine and α-D-ribose-1-phosphate (EC2.4.2.1 KEGG R01561; adenosine: phosphate α-D-ribosyltransferase; also known as adenosine phosphorylase) by the FAMIN protein. The reaction is reversible and the purine nucleoside phosphorylase activity of FAMIN may also convert a purine nucleobase and ribose-1-phosphate molecule into a purine nucleoside and phosphate.

The purine nucleoside phosphorylase activity of the FAMIN protein may be determined by measuring the conversion of purine nucleoside and phosphate into a nucleobase and a ribose-1-phosphate molecule; or a nucleobase and a ribose-1-phosphate molecule into a purine nucleoside and phosphate in the presence of the FAMIN protein.

In some embodiments, purine nucleoside phosphorylase activity may be determined by;
  contacting the FAMIN protein with a purine nucleoside in a reaction solution; and
  determining the amount of purine nucleoside; or purine nucleobase and/or ribose-1-phosphate molecule in the reaction solution following said contacting.

The FAMIN protein may be contacted with the purine nucleoside in the presence of inorganic phosphate. For example, the reaction solution may comprise phosphate buffered saline. In some embodiments, the amount of phosphate in the reaction solution following said contacting may be determined.

Depletion of purine nucleoside and/or phosphate or generation of the purine nucleobase and/or ribose-1-phosphate molecule in the reaction solution is indicative of the purine nucleoside phosphorylase activity of the FAMIN protein. The amount or rate of decrease in the concentration of purine nucleoside or increase in the concentration of purine nucleobase and/or ribose-1-phosphate molecule in the reaction solution is indicative of the amount of purine nucleoside phosphorylase activity in the reaction solution. Depletion of purine nucleoside or generation of the purine nucleobase and/or ribose-1-phosphate molecule in the reaction solution may be determined in the presence relative to the absence of the isolated FAMIN protein.

In some embodiments, purine nucleoside phosphorylase activity may be determined by;
  contacting the FAMIN protein with purine nucleobase and a ribose-1-phosphate molecule in a reaction solution; and
  determining the amount of purine nucleoside and/or phosphate; or purine nucleobase and/or ribose-1-phosphate molecule in the reaction solution following said contacting.

Depletion of purine nucleobase and/or ribose-1-phosphate molecule or generation of the purine nucleoside in the reaction solution by the FAMIN protein is indicative of purine nucleoside phosphorylase activity. The amount or rate of decrease in the concentration of purine nucleobase and/or ribose-1-phosphate molecule or increase in the concentration of purine nucleoside in the reaction solution may be indicative of the amount of purine nucleoside phosphorylase activity in the reaction solution. Depletion of purine nucleobase and/or ribose-1-phosphate molecule or generation of the purine nucleoside in the reaction solution may be determined in the presence relative to the absence of the isolated FAMIN protein.

A purine nucleoside may include guanosine, adenosine and inosine molecule, or analogues or derivatives thereof.

An inosine nucleoside may include inosine, deoxy-inosine, or analogues or derivatives thereof.

In some embodiments, the FAMIN protein may be contacted with multiple different purine nucleosides or purine nucleobases, either simultaneously or in series, and the depletion of the multiple purine nucleosides or purine nucleobases and/or the generation of multiple reaction products may be determined.

In some embodiments, the purine nucleoside is an inosine molecule. For example, the purine nucleoside may be inosine (CID 6021), the purine nucleobase may be hypoxanthine (CID 790) and the ribose-1-phosphate molecule may be α-D-ribose-1-phosphate (CID 439236). Alternatively, the purine nucleoside may be deoxy-inosine; the purine nucleobase may be hypoxanthine and the ribose-1-phosphate molecule may be 2'deoxy-α-D-ribose-1-phosphate (CID 439287).

In other embodiments, the purine nucleoside is guanosine (CID 6802), the purine nucleobase is guanine and the ribose-1-phosphate molecule is α-D-ribose-1-phosphate. In other embodiments, the purine nucleoside is adenosine (CID 60961), the purine nucleobase is adenine and the ribose-1-phosphate molecule is α-D-ribose-1-phosphate.

The purine nucleoside phosphorylase activity of FAMIN may convert adenosine into adenine and a ribose-1-phosphate molecule (i.e. adenosine phosphorylase activity). A FAMIN protein may therefore convert adenosine into inosine through its adenosine deaminase activity or adenine through its adenosine phosphorylase activity. Inosine may be further converted into hypoxanthine by the FAMIN protein, as described above.

The adenosine phosphorylase activity may be determined by;
contacting the FAMIN protein with adenosine in a reaction solution; and
determining the amount of adenosine or the amount of adenine and/or ribose-1-phosphate molecule in the reaction solution following said contacting.

The FAMIN protein may be contacted with the adenosine in the presence of inorganic phosphate. For example, the reaction solution may comprise phosphate buffered saline. In some embodiments, the amount or rate of phosphate in the reaction solution following said contacting may be determined. Depletion of adenosine and/or phosphate or generation of adenine and/or ribose-1-phosphate in the reaction solution by the FAMIN protein is indicative of adenosine phosphorylase activity. For example, a decrease in the concentration of adenosine or an increase in the concentration of adenine and/or ribose-1-phosphate in the reaction solution may be indicative of activity.

In some embodiments, depletion of adenosine and/or phosphate or generation of adenine and/or ribose-1-phosphate in the reaction solution may be determined in the presence relative to the absence of the isolated FAMIN protein. In other embodiments, depletion of adenine and/or ribose-1-phosphate molecule or generation of adenosine and/or phosphate in the reaction solution may be determined in the presence of wild type FAMIN protein relative to the FAMIN-I254V mutant, which has selectively impaired adenosine phosphorylase activity.

In some embodiments, adenosine phosphorylase activity may be determined by;
contacting the FAMIN protein with adenine and a ribose-1-phosphate molecule in a reaction solution; and
determining the amount of adenosine and/or phosphate; or adenine and/or ribose-1-phosphate molecule in the reaction solution following said contacting.

Depletion of adenine and/or ribose-1-phosphate molecule or generation of adenosine and/or phosphate in the reaction solution by the FAMIN protein is indicative of adenosine phosphorylase activity. The amount or rate of decrease in the concentration of adenine and/or ribose-1-phosphate molecule or increase in the concentration of adenosine and/or phosphate in the reaction solution may be indicative of the amount of adenosine phosphorylase activity in the reaction solution.

In some embodiments, depletion of adenine and/or ribose-1-phosphate molecule or generation of the adenosine and/or phosphate in the reaction solution may be determined in the presence relative to the absence of the isolated FAMIN protein. In other embodiments, depletion of adenine and/or ribose-1-phosphate molecule or generation of adenosine and/or phosphate in the reaction solution may be determined in the presence of wild type FAMIN protein relative to the FAMIN-I254V mutant, which has selectively impaired adenosine phosphorylase activity.

Methylthioadenosine phosphorylase activity converts methylthioadenosine nucleosides into adenine nucleobases and S-methyl-5'-thioribose-1-phosphate (i.e. methylthioribose-1-phosphate) molecules. A methylthioadenosine nucleoside may include S-methyl-5'-thioadenosine (i.e. 5-methylthioadenosine) and analogues or derivatives thereof. An adenine nucleobase may include adenine and analogues or derivatives thereof. A methylthioribose-1-phosphate molecule may include S-methyl-5-thio-α-D-ribose-1-phosphate and analogues or derivatives thereof. For example, 5-methylthioadenosine (CID 149) may be converted into adenine (CID 190) and S-methyl-5-thio-α-D-ribose-1-phosphate (CID 45266677) (EC2.4.2.28). The reaction is reversible and methylthioadenosine phosphorylase activity may also convert adenine nucleobases and methylthioribose-1-phosphate molecules into methylthioadenosine nucleosides.

In some embodiments, methylthioadenosine phosphorylase activity may be determined by;
contacting the FAMIN protein with a methylthioadenosine nucleoside in a reaction solution; and
determining the amount of methylthioadenosine nucleoside; or adenine nucleobase and/or methylthioribose-1-phosphate molecule in the reaction solution following said contacting.

The FAMIN protein may be contacted with the methylthioadenosine nucleoside in the presence of inorganic phosphate. For example, the reaction solution may comprise phosphate buffered saline. In some embodiments, the amount of phosphate in the reaction solution following said contacting may be determined.

Depletion of methylthioadenosine nucleoside or generation of the adenine nucleobase and/or methylthioribose-1-phosphate molecule in the reaction solution by the FAMIN protein is indicative of methylthioadenosine phosphorylase activity. For example, the amount of decrease in the concentration of methylthioadenosine nucleoside or increase in the concentration of adenine nucleobase and/or methylthioribose-1-phosphate molecule in the reaction solution is indicative of the amount of methylthioadenosine phosphorylase activity in the reaction solution. Depletion of methylthioadenosine nucleoside or generation of the adenine nucleobase and/or methylthioribose-1-phosphate molecule in the reaction solution may be determined in the presence relative to the absence of the isolated FAMIN protein.

The adenosine deaminase and purine nucleoside phosphorylase activities of FAMIN in combination may convert adenosine nucleosides into hypoxanthine and a ribose-1-phosphate molecule.

Adenosine deaminase and purine nucleoside phosphorylase activity may be determined by;
contacting the FAMIN protein with adenosine nucleoside in a reaction solution; and
determining the amount of adenosine nucleoside or hypoxanthine and/or ribose-1-phosphate molecule in the reaction solution following said contacting.

The FAMIN protein may be contacted with the adenosine nucleoside in the presence of inorganic phosphate (e.g. orthophosphate). For example, the reaction solution may comprise phosphate buffered saline. In some embodiments, the amount of phosphate in the reaction solution following said contacting may be determined Depletion of adenosine nucleoside or generation of hypoxanthine and/or ribose-1-phosphate in the reaction solution by the FAMIN protein is indicative of combined adenosine deamination and purine nucleoside phosphorylase activity. For example, a decrease in the concentration of adenosine nucleoside or an increase in the concentration of hypoxanthine and/or ribose-1-phosphate in the reaction solution is indicative of the combined activity. Depletion of adenosine nucleoside or generation of hypoxanthine and/or ribose-1-phosphate in the reaction solution may be determined in the presence relative to the absence of the isolated FAMIN protein.

In some embodiments, the adenosine nucleoside is adenosine and the ribose-1-phosphate is α-D-ribose-1-phosphate. In other embodiments, the adenosine nucleoside is deoxyadenosine and the ribose-1-phosphate is deoxy-α-D-ribose-1-phosphate. For example, the adenosine nucleoside may be 2'-deoxyadenosine and the ribose-1-phosphate may be 2'-deoxy-α-D-ribose-1-phosphate or the 5'-deoxyadenosine and the ribose-1-phosphate may be 5'-deoxy-α-D-ribose-1-phosphate.

In some embodiments, the adenosine deaminase activity, purine nucleoside phosphorylase activity and/or methylthioadenosine phosphorylase activity of an isolated FAMIN protein may be determined in the presence and absence of test compound. A decrease in activity in the presence relative to the absence of test compound is indicative that the test compound is a FAMIN inhibitor. This may be useful in screening for compounds that inhibit FAMIN as described below.

In some embodiments, the reactants in the reactions described herein may be isolated molecules. Suitable reactant molecules may be synthesised using conventional techniques or obtained from commercial suppliers (e.g. Sigma-Aldrich Corp, St. Louis, MO, USA). In other embodiments, the reactants in the reactions described herein may be within a cell extract, for example an aqueous phase extract of cell metabolites (as shown for example in FIGS. 1A-1F). Suitable cell extracts may be devoid of protein and may include for example aqueous extracts obtained by Folch extraction (Folch et al., J Biol Chem 1957, 226, 497). An aqueous extract of reactants may be freeze-dried and re-suspended in phosphate-buffered saline.

The reactions may be performed in a reaction solution comprising inorganic phosphate ($P_i$). For example a phosphate containing buffer, such as PBS, may be used. The reaction solution may be devoid of co-factors or reactants other than inorganic phosphate.

The reactions may be performed at any convenient temperature, for example 32° C. to 42° C., such as 37° C.

The reactions may be performed at any convenient pH, for example pH 7-8, such as pH 7.4.

The depletion of a substrate or the generation of a product in the adenosine deaminase, purine nucleoside phosphorylase and/or methylthioadenosine phosphorylase reactions described herein may be determined by any convenient technique. Suitable techniques include, for example, absorbance, chromatography-coupled mass spectrometry (e.g. LC-MS/MS) or NMR. In some preferred embodiments, the reactants or the generation of products in the reaction solution may be measured by LC-MS/MS.

In some embodiments, depletion of a substrate or the generation of a product in a FAMIN-mediated adenosine deaminase, purine nucleoside phosphorylase and/or methylthioadenosine phosphorylase reaction described herein may be determined by measuring absorbance. The substrates and products described above may display different absorbance spectra and changes in absorbance at one or more selected wavelengths in the reaction solution may be indicative of the depletion of a substrate or the generation of a product.

In some embodiments, the depletion of a substrate or generation of product in a FAMIN-mediated reaction described herein may be determined using a substituted analogue of the substrate or product which displays characteristic spectrophotometric properties, such that the concentration of the analogue in the reaction solution can be directly measured.

In some embodiments, a substrate may be labelled with a detectable label. Conversion of the substrate into products by the FAMIN protein as described herein may release the detectable label, which may then be measured by any convenient means.

In some embodiments, the depletion of substrate or the generation of product may be determined using a detection reaction which generates a detectable compound in the presence of the reactant or product. For example, the depletion or generation of xanthine may be determined using xanthine oxidase that generates $H_2O_2$, which can be detected by detection reagents, such as luminescence or fluorescence reagents. The detection reaction may be coupled with the FAMIN mediated reaction. For example, both FAMIN and xanthine oxidase may be present in the reaction solution. Alternatively, the detection reaction may be performed after the FAMIN mediated reaction.

Alternatively, the depletion or generation of inorganic phosphate may be determined using purine nucleoside phosphorylase (PNP). Suitable assay methods and kits are well known in the art and commercially available (for example EnzChek® Phosphate Assay Kit, ThermoFisher Scientific). For example, inorganic phosphate in the reaction solution may be determined by the conversion of the 2-amino-6-mercapto-7-methylpurine riboside (MESG) into ribose 1-phosphate and 2-amino-6-mercapto-7-methylpurine product, which can be detected through a spectrophotometric shift in maximum absorbance from 330 nm (substrate) to 360 nm (product).

Methods of measuring FAMIN activity as described herein may be useful in screening for compounds that modulate, e.g. promote or inhibit, FAMIN activity.

In some embodiments, screening may be performed using an isolated FAMIN protein. For example, a method of screening for a compound that modulates the activity of a FAMIN protein may comprise;
determining the adenosine deaminase activity, purine nucleoside phosphorylase activity and/or methylthioadenosine phosphorylase activity of an isolated FAMIN protein in the presence and absence of a test compound.

A difference in the adenosine deaminase activity, purine nucleoside phosphorylase activity and/or methylthioadenosine phosphorylase activity of the FAMIN protein that is measured in the presence of test compound relative to the absence of test compound may be indicative that the test compound modulates the activity of FAMIN protein.

A decrease in the adenosine deaminase activity, purine nucleoside phosphorylase activity and/or methylthioadenosine phosphorylase activity of the FAMIN protein in the presence relative to the absence of test compound is indicative that the test compound is a FAMIN inhibitor or antagonist.

An increase in the adenosine deaminase activity, purine nucleoside phosphorylase activity and/or methylthioadenosine phosphorylase activity of the FAMIN protein in the presence relative to the absence of test compound is indicative that the test compound is a FAMIN potentiator or agonist.

The adenosine deaminase activity, purine nucleoside phosphorylase activity and/or methylthioadenosine phosphorylase activity of an isolated FAMIN protein may be determined as described above.

An increase or decrease in one or more of (i) the conversion of an adenosine molecule into an inosine molecule, (ii) the conversion of a purine nucleoside into a nucleobase and a ribose-1-phosphate molecule in the presence of the FAMIN protein, (iii) the conversion of a nucleobase and a ribose-1-phosphate molecule into a purine nucleoside (iv) the conversion of adenosine into adenine and a ribose-1-phosphate molecule in the presence of the FAMIN protein, (v) the conversion of adenine and a ribose-1-phosphate molecule into adenosine (vi) the conversion of methylthioadenosine into adenine and a S-methyl-5'-thioribose-1-phosphate molecule, or (vii) the conversion of adenine and a S-methyl-5'-thioribose-1-phosphate molecule into methylthioadenosine; by the FAMIN protein in the presence relative to the absence of the test compound is indicative that the test compound is a FAMIN potentiator or inhibitor, respectively.

The precise format of any of the screening or assay methods of the present invention may be varied by those of skill in the art using routine skill and knowledge. The skilled person is well aware of the need to employ appropriate control experiments. For example, in some embodiments, the amount of the above compounds may also be determined in a control in which FAMIN is inactivated.

A test compound may be an isolated molecule or may be comprised in a sample, mixture or extract, for example, a biological sample. Compounds which may be screened using the methods described herein may be natural or synthetic chemical compounds used in drug screening programmes. Extracts of plants, microbes or other organisms, which contain several characterised or uncharacterised components may also be used.

Combinatorial library technology provides an efficient way of testing a potentially vast number of different compounds for ability to modulate FAMIN activity. Such libraries and their use are known in the art, for all manner of natural products, small molecules and peptides, among others. The use of peptide libraries may be preferred in certain circumstances The amount of test compound which may be added to an assay of the invention will normally be determined by trial and error depending upon the type of compound used. Typically, from about 0.001 nM to 1 mM or more concentrations of putative inhibitor compound may be used, for example from 0.01 nM to 100 µM, e.g. 0.1 to 50 µM, such as about 10 µM. Even a compound which has a weak effect may be a useful lead compound for further investigation and development.

Suitable test compounds for screening include compounds that inhibit similar activities to the adenosine deaminase, purine nucleoside phosphorylase and methylthioadenosine phosphorylase activities of FAMIN. Suitable test compounds include ADA inhibitors, such as 3'-deoxy-N-(1-oxododecyl) adenosine, pentostatin (PubchemID 439693, CAS ID 53910-25-1) and EHNA (erythro-9-(2-hydroxy-3-nonyl)adenine (PubchemID 3206, CAS ID 59262-86-1) (see for example Chauhan and Kumar (2015) Med Chem Res 24:2259); PNP inhibitors, such as 8-aminoguanosine (PubchemID 96849; CAS ID 180288-69-1) (see for example Bzowska et al (2000) Pharmacol Therap 88:349); MTAP inhibitors, such as MT-ImmA and MT-DADMe-ImmA (MT-DIA) (see for example Firestone et al (2017) ACS Chem Biol 12:464); and purine nucleosides.

Suitable test compounds also include analogues, derivatives, variants and mimetics of any of the compounds listed above, for example compounds produced using rational drug design to provide test candidate compounds with particular molecular shape, size and charge characteristics suitable for modulating FAMIN activity.

A test compound identified as modulating FAMIN activity may be investigated further. For example, the selectivity of a compound for FAMIN may be determined by screening against other isolated ADA, PNP or MTAP enzymes. Suitable methods for determining the effect of a compound on the activity of recombinant enzymes are well known in the art.

A test compound identified as modulating FAMIN activity may be isolated and/or purified or alternatively, it may be synthesised using conventional techniques of recombinant expression or chemical synthesis. Furthermore, it may be manufactured and/or used in preparation, i.e. manufacture or formulation, of a composition such as a medicament, pharmaceutical composition or drug. Methods described herein may thus comprise formulating the test compound in a pharmaceutical composition with a pharmaceutically acceptable excipient, vehicle or carrier for therapeutic application.

Following identification of a compound which modulates FAMIN activity as described herein, a method may further comprise modifying the compound to optimise its pharmaceutical properties. Suitable methods of optimisation, for example by structural modelling, are well known in the art.

Further optimisation or modification can then be carried out to arrive at one or more final compounds for in vivo or clinical testing.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Experimental

Materials and Methods

Cell Lines

HepG2 (ATCC HB-8065) and HEK293T (ATCC CRL-3216) cell lines were maintained in complete DMEM with 10% FBS. Sanger sequencing of the FAMIN gene identified the HepG2 cell line as heterozygous at SNP rs3764147, encoding FAMIN (p.254I/p.254V). Silencing experiments were carried out using reverse transfection with Lipofectamine RNAiMAX reagent and 25 nM of small interfering RNA (siRNA) according to the manufacturer's guidelines. HepG2 cells were silenced using siRNA (SMART pool technology; Dharmacon) against human FAMIN (LACC1; M-015653-00). Silencing efficiency was verified using qPCR and gene expression confirmed to be reduced by at least 80% at 48 hours following transfection. Non-targeting siRNA (Dharmacon) was used as negative control.

Extraction of Aqueous and Lipid Metabolites

Cells were harvested as indicated using either direct extraction with 4:1 methanol:water or Trypsin-EDTA (0.25%). For direct methanol extraction, cells were washed with PBS followed by addition of pre-chilled 500 μl 4:1 methanol:water. Cells were scraped and the resulting methanol mixture transferred to 2 mL-flat-bottomed screw cap tubes. Samples were then vortexed, sonicated and lastly centrifuged at 21,000 g for 10 minutes to pellet any debris. The supernatant was transferred to new 2 mL tubes for drying as described below. All solvents used were HPLC grade or higher and obtained from Honeywell (Fisher Scientific). Cell pellets harvested using trypsinization were washed with PBS and then subjected to extraction using the methanol:chloroform method described by Folch (5). Briefly, a stainless steel ball (Qiagen) was added to each washed cell pellet on dry ice along with 1 mL of ice cold 2:1 chloroform:methanol inside a 2 mL-flat-bottomed screw cap tube (Starlab). The samples were homogenised using a Tissue Lyser (Qiagen) for 10 min at 25 Hz to ensure optimum extraction and ascertaining to freeze the tissue lyser plates prior to homogenisation in order to keep samples cold during extraction. 400 μl of ice cold water was added and the samples thoroughly vortexed and sonicated for 5 minutes before centrifugation at 21,000 g for 5 min. After centrifugation the aqueous (top layer) and organic (bottom layer) fractions were separated and aliquoted into separate screw-cap tubes both kept on dry ice. A further 1 mL of 2:1 chloroform:methanol was added to the original tube containing the protein pellet and the extraction repeated as described above. The resulting layers were combined, dried (as described below) and stored at −20° C. prior to further preparation and analysis.

LC-MS Sample Preparation

Aqueous extracts of cells or protein reaction mixtures were lyophilised using a centrifugal evaporator (Labconco) and reconstituted in 100 μl (for cell extracts) and 200 μl (for protein reaction mixtures) of 70:30 acetonitrile: 0.1 M aqueous ammonium carbonate water containing 2 μM [$^{13}C_{10}$, $^{15}N_5$] adenosine monophosphate, adenosine triphosphate [$^{13}C_{10}$, $^{15}N_5$], succinic acid $^{13}C_{10}$ and glutamic acid [$^{13}C_5$, $^{15}N_5$] (all from Sigma Aldrich except the glutamic acid from Cambridge Isotope Laboratories) as internal standards, although it should be noted that for experiments using labelled substrates internal standards were omitted to avoid contamination of metabolites. The resulting solution was vortexed then sonicated for 15 min followed by centrifugation at 21,000 g to pellet any remaining undissolved material. After centrifugation the supernatant was transferred with an automatic pipette into a 300 μl vial with insert (Fisher Scientific) and capped ready for analysis.

LC-MS Analysis of Aqueous Metabolites

For untargeted analysis, a Velos Pro Elite orbitrap mass spectrometer coupled to a U3000 chromatography system or a Q Exactive Plus orbitrap coupled to a Vanquish Horizon ultra-high performance liquid chromatography system was used. For targeted analysis, samples were analysed using a Quantiva triple stage quadrupole mass spectrometer coupled to a Vanquish Horizon (all analytical instrument combinations supplied by Thermo Fisher Scientific).

Samples were then analysed using a bridged ethylene hybrid (BEH) amide hydrophilic interaction liquid chromatography (HILIC) approach for the highly polar aqueous metabolites. For this analysis the strong mobile phase (A) was 100 mM ammonium carbonate, the weak mobile phase was acetonitrile (B) with 9:1 water:acetonitrile being used for the needle wash. The LC column used was the BEH amide column (150×2.1 mm, 1.7 μm, Waters). The following linear gradient was used: 20% A in acetonitrile for 1.5 min followed by an increase to 60% A over 2.5 min with a further 1 min at 60% A after which the column was re-equilibrated for 1.9 min. After each chromatographic run the column was washed with 30 column volumes of 6:4 water:acetonitrile followed by a further 10 column volumes of 95:5 acetonitrile:water for storage. The total run time was 7 min, the flow rate was 0.6 mL/min and the injection volume was 5 μL. In order to resolve pentose phosphates for identification of ribose-1-phosphate a shallower gradient was employed: 30% A in acetonitrile for 2.0 minutes followed by an increase to 50% A over 3.0 minutes with re-equilibration for 1.9 minutes. After HILIC analysis samples were dried and reconstituted in the same volume of 10 mM ammonium acetate prior to orthogonal mixed mode analysis using an ACE Excel C18-PFP column (150×2.1 mm, 2.0 μm, Hichrom). Mobile phase A consisted of water with 0.1% formic acid and mobile phase B was acetonitrile with 0.1% formic acid. For gradient elution mobile phase B was held at 0% for 1.6 min. followed by a linear gradient to 30% B over 4.0 minutes, a further increase to 90% over 1 min and a hold at 90% B for 1 min with re-equilibration for 1.5 minutes giving a total run time of 6.5 minutes. The flow rate was 0.5 mL/min and the injection volume was 2 μL. The needle wash used was 4:1 water:acetonitrile with 0.1% formic acid. Both chromatography modes were used for both targeted and untargeted analysis.

For enzyme kinetic assays a further chromatographic approach was used to allow for analysis of all substrates and products using a single assay. A Waters BEH C8 column was used (100×2.1 mm, 1.7 μm) with a weak mobile phase (A) of aqueous 10 mM ammonium acetate with 0.1% ammonia and a strong mobile phase (B) of acetonitrile. For gradient elution mobile phase B was held at 0% for 1.6 min, followed by a linear gradient to 30% B over 4.0 minutes, a further increase to 90% over 1 min, and a hold at 90% B for 1 min, with re-equilibration for 1.5 minutes giving a total run time of 6.5 minutes. The flow rate was 0.5 mL/min and the injection volume was 2 μL. The needle wash used was 4:1 water:acetonitrile.

Untargeted analysis on the Elite used a high resolution FTMS full scan of 60-1500 m/z with a resolution of 60,000 ppm where due to positive mode negative mode equilibration times each mode was run independently. Source parameters used for the orbitrap were a vaporizer temperature of 400° C. and ion transfer tube temperature of 300° C., an ion spray voltage of 3.5 kV (2.5 kV for negative ion mode) and a sheath gas, auxiliary gas and sweep gas of 55, 15 and 3 arbitrary units respectively with an S-lens RF (radio frequency) of 60%. For untargeted analysis using the Q Exactive Plus a full scan of 60-900 m/z was used at a resolution of 70,000 ppm where positive and negative ion mode assays were run separately in order to maximise data points across a peak at the chosen resolution. The source parameters were the same as those used for the Elite. For analysis of CoA species using the Q Exactive orbitrap unique mass spectrometry methodology was employed where the full scan mass range was reduced to 800-1000 m/z, the capillary temperature was increased to 350° C. and the S-lens RF to 100%.

Targeted analysis on the Quantiva utilised selected reaction monitoring (SRM) employing fast polarity switching with mass transitions and compound dependent parameters (collision energy voltage and RF lens voltage) determined on infusion of 1 μM standards at a flow rate of 10 μl/min in 4:1 acetonitrile:water with 0.1% acetic acid. Source parameters used were a vaporizer temperature of 440° C. and ion transfer tube temperature of 362° C., an ion spray voltage of 3.5 kV (2.5 kV for negative ion mode) and a sheath gas, auxiliary gas and sweep gas of 54, 17 and 2 arbitrary units respectively.

LC-MS Data Processing

Data were acquired, processed and integrated using Xcalibur (Version 3.0, Thermo Fisher Scientific) and Compound Discoverer (Version 2.1, Thermo Fisher Scientific). For untargeted analysis, metabolites of interest were identified using high resolution m/z values as specified in the METLIN database (Scripps Research Institute) corresponding to their $[M+H]^+$ or $[M-H]^-$ ion adducts in positive or negative ionisation modes, respectively. Compound retention time and fragmentation pattern were validated against known external standards. Peak areas corresponding to metabolite levels were manually quantified and normalised to internal standard or total ion content (as appropriate) and presented as relative areas. All sample data were processed using Compound Discoverer (Version 2.1, Thermo Fisher Scientific) to accurately calculate total ion content for normalisation.

For multivariate analysis, data were processed using Compound Discoverer (Version 2.1, Thermo Fisher Scientific) to determine putative compounds with differential abundance between sample groups. For each differential MS feature, chromatogram peaks were manually verified using Xcalibur (Version 3.0, Thermo Fisher Scientific). Accurate m/z values were compared against the METLIN database (Scripps Research Institute) including $[M+H]^+$, $[M+Na]^+$, $[M+NH_4]^+$ for positive mode and $[M-H]^-$, $[M+Cl]^-$ for negative mode ion adducts with a mass tolerance of 2 ppm. A combination of MS/MS fragmentation profile, molecular formulae calculation based on isotope pattern and expected chromatographic chemical behaviour was then used to attribute metabolite identity. In case of ambiguity, and for all proposed FAMIN products and substrates, external standards were used to confirm metabolite identification. Data from positive and negative ionisation modes were combined and duplicate metabolite identities removed. Data was normalised to total ion content and fold change graphically depicted as volcano plots. Metabolite levels between groups were compared using a two-tailed, unpaired Student's t-test.

Reagents

The following reagents were used: M-CSF (Peprotech, 300-25), LPS (from *E. coli* K12, InvivoGen, tlrl-peklps), recombinant mouse IFN-α (BIO-RAD, PMP29Z), murine IFN-γ (Peprotech, 315-05), adenosine (Sigma Aldrich, A9251), inosine (Sigma Aldrich, 14125), hypoxanthine (Sigma Aldrich, H9377), methylthioadenosine (Sigma Aldrich, D5011), S-adenosylmethionine (Sigma Aldrich, A7007), S-adenosylhomocysteine (Sigma Aldrich, A9384), cytidine (Sigma Aldrich, C122106), uridine (Sigma Aldrich, U3750), xanthosine (Sigma Aldrich, X0750), 2'deoxyadenosine (Sigma Aldrich, D7400), 5'deoxyadenosine (Sigma Aldrich, D1771), cholesterol oxidase (Sigma Aldrich, C8649), $^{13}C_{10}$, $^{15}N_5$-adenosine (Cambridge Isotope Laboratories), $^{15}N_5$-adenine (Cambridge Isotope Laboratories) for isotopic tracing experiments; all standards for validation of mass spectrometry compound identification were purchased through Sigma Aldrich.

Plasmids

A pESG-IBA105 vector (IBA Life Sciences 5-4505-001) was used for the mammalian expression of FAMIN$^{254I}$, allowing expression of recombinant protein containing a twin Strep-tag at the N-terminus under CMV enhancer and promoter elements. The DNA sequence of human FAMIN was amplified with Phusion DNA polymerase (NEB M0530) from an IMAGE clone (MHS1010-7508636) using a forward primer containing a leader sequence with Esp3I targeting site followed by TEV cleavage sequence, and reverse primer containing an Esp3I targeting site. The purified PCR product was digested with Esp3I (NEB R0734) and verified on 1% agarose gel. The gel-purified amplicon was then cloned into Esp3I-digested pESG-IBA105 with T4 DNA ligase (NEB M0202). The ligated plasmid was verified by Sanger sequencing, with a final construct consisting of, from the 5' to 3' ends, a Kozak sequence just upstream of the start codon of twin Strep-tag, followed by a short linker and a TEV cleavage motif sequence and human FAMIN sequence. A similar protocol was adapted for the YfiH and YlmD constructs, using pPSG-IBA105 plasmid vector (IBA Life Sciences 5-4305-001) that allows expression of recombinant protein containing twin Strep-tag at the N-terminus under constitutive T7 promoter. The DNA sequences of yfiH and ylmD were custom-synthesised by Origene and codon-optimised for prokaryotic expression, with Esp3I target sites flanking the sequence and TEV cleavage motif immediately upstream of the gene. The Esp3I-digested yfiH and ylmD sequences were then cloned into Esp3I-digested pPSG-IBA105 with T4 DNA ligase (NEB). Site-directed mutagenesis was subsequently performed using Q5 Site-Directed Mutagenesis Kit (NEB E0554), following the manufacturer's instruction, to generate FAMIN$^{254V}$ for both prokaryotic and mammalian expression. All constructs generated were verified by Sanger sequencing.

Protein Expression and Purification

HEK293T cells were transfected with PEI-DNA complex containing plasmids for mammalian expression of Strep-tagged FAMIN. After 48-72 hours, transfected cells were harvested and resuspended in detergent-free pre-chilled suspension buffer (100 mM NaCl, 20 mM HEPES, 5 mM TCEP and 10% glycerol pH 8.0) supplemented with Complete Mini EDTA-free protease inhibitor cocktail (Sigma 11836170001). Following sonication and clearance by centrifugation at 30,000 rpm, the lysates were then loaded onto a Streptactin XT Superflow column (IBA Life Sciences 2-4012-001) pre-equilibrated with 2 column volumes of lysis buffer. The column was then washed with 10 column volumes of wash buffers and the Strep-tagged protein was eluted from the column with 6 column volumes of 50 mM biotin. The purified recombinant protein was then incubated with N-terminally 6×His-tagged TEV protease (Sigma TEV protease) at a ratio of 10:1 as determined by A280 quantification using Nano Drop spectrophotometer. The mixture was incubated overnight at 4° C. The TEV protease was then removed by passing the mixture through a 1 ml Ni-NTA Superflow column (IBA Life Sciences 2-3206-025), after pre-equilibrating the column with the protein buffer. TEV protease binds to the column and the recombinant protein, in the flow-through, was collected. The flow-through constituting tag-free recombinant protein was collected. This was then concentrated with a 10 kDa column filter (Amicon) and further purified by size exclusion using an AKTA Superdex 200 increase (10/300) column (GE Life Sciences), followed by copious washing. Eluted fractions corresponding to positive peaks on the chromatogram were confirmed on Coomassie SDS-PAGE.

For prokaryotic expression, T7 Express lysY/Iq High Competent *E. coli* (NEB C3013) were transformed with plasmids containing the DNA sequence of recombinant protein. Fresh colonies (less than 2 weeks after plating) were inoculated into an LB broth supplemented with 0.5% glucose and grown at 30° C. in a shaking incubator. Upon reaching OD600 of 0.4-0.7, protein expression was induced with 0.3 mM of IPTG. After 4-6 hours, bacterial culture was centrifuged at 14000 rpm for 15 minutes. The cell pellet was re-suspended in 5 ml of pre-chilled hypotonic lysis buffer (20 mM NaCl, 20 mM HEPES, 10% glycerol, pH 8.0) supplemented with protease inhibitors. Following sonication, the lysates were cleared by centrifugation at 30,000 rpm for 15 minutes and treated with 5 µg/ml of DNase I (Sigma) and 10 ug/ml of RNAse A (Sigma) for 15 minutes on ice. Subsequent protein purification steps were similar to those employed above in the mammalian expression system.

Enzyme Assays

Putative enzymatic function of recombinant human strep-tagged FAMIN was investigated against aqueous HepG2 metabolite extracts (dried, Folch extracted from $5\times10^6$ cells) or nucleoside substrates at indicated concentrations and detected using HPLC-MS as described above. Unless otherwise indicated in the figure legends, HEK293T cell-expressed protein was used for all assays. The reaction mixture (final volume 100 µL) consisted of 10 µg of recombinant protein and 10 µM nucleoside substrate in Dulbecco's PBS (Thermo Fisher), pH 7.4 unless otherwise indicated. The samples were incubated at 37° C. for 1 h and then quenched with ×5 volume of ice-cold methanol. Samples were centrifuged at 21,000 g for 5 min transferred to fresh tubes and then dried down prior to analysis as described above.

Mice 6- to 10-week-old mice were used for all experiments and were age and gender matched for individual experiments. $Famin^{+/+}$, $Famin^{-/-}$, $Famin^{p.254I}$, $Famin^{p.254V}$ and $Famin^{p.284R}$ mice have previously been described (1). Mice were bred and maintained under specific pathogen-free conditions at the Central Biomedical Services facility, University of Cambridge. All procedures performed had local ethics and UK Home Office approval.

Murine Bone Marrow-Derived Macrophage Isolation

Bone marrow derived macrophages (BMDMs) were prepared by flushing mouse femurs and tibias with PBS. Cells were filtered through a 70 µm cell strainer and re-suspended in complete RPMI-1640 medium (containing 100 U/mL of penicillin-streptomycin, 1 mM HEPES buffer and 10% FBS). To generate BMDMs, cells were cultured for 6 days in complete medium containing 100 ng/mL of M-CSF with media exchanged after 3 days. Macrophages were harvested, seeded and polarized for 24 h toward M1φ with IFN-γ (50 ng/mL) plus LPS (20 ng/mL). As indicated, recombinant IFNα was added to undifferentiated BMDMs at 500 IU/mL for 16 h prior to direct methanol extraction.

Statistical Analysis

Statistical analyses were performed using Graphpad Prism 6.0 or, as described in LC-MS analysis methods, Compound Discoverer (Thermo Scientific). Unless otherwise stated, statistical significance was calculated as appropriate using unpaired, two-tailed Student's t-test as described in the figure legends. Data are represented as mean and standard error of the mean (S.E.M.). A P value of <0.05 was considered significant.

Results

We hypothesised that FAMIN is an enzyme and devised an unbiased screen for activity against an extensive library of metabolites without a priori assumptions on putative function. We optimised a strategy for large-scale production of highly purified, recombinant human FAMIN from transiently transfected HEK293T cells, using Strep-tag affinity purification, TEV protease-mediated tag cleavage and size-exclusion chromatography. The resultant FAMIN protein exhibited stable properties in solution consistent with correct folding and lack of aggregation. To generate a suitable metabolomic library of substrates and potential cofactors, we tested a variety of cell lines for FAMIN functionality. The human hepatocellular carcinoma cell line HepG2 entered growth arrest after transfection with FAMIN siRNA, which became evident after 72 h. HepG2 cells also exhibited reduced glycolysis and oxidative phosphorylation 48 h after FAMIN siRNA transfection, resembling observations in macrophages (1). This indicated that FAMIN is active and performs a non-redundant role in HepG2 cells, which could thus be reasonably expected to contain all cofactors and substrates necessary for FAMIN function.

Figure 1B:
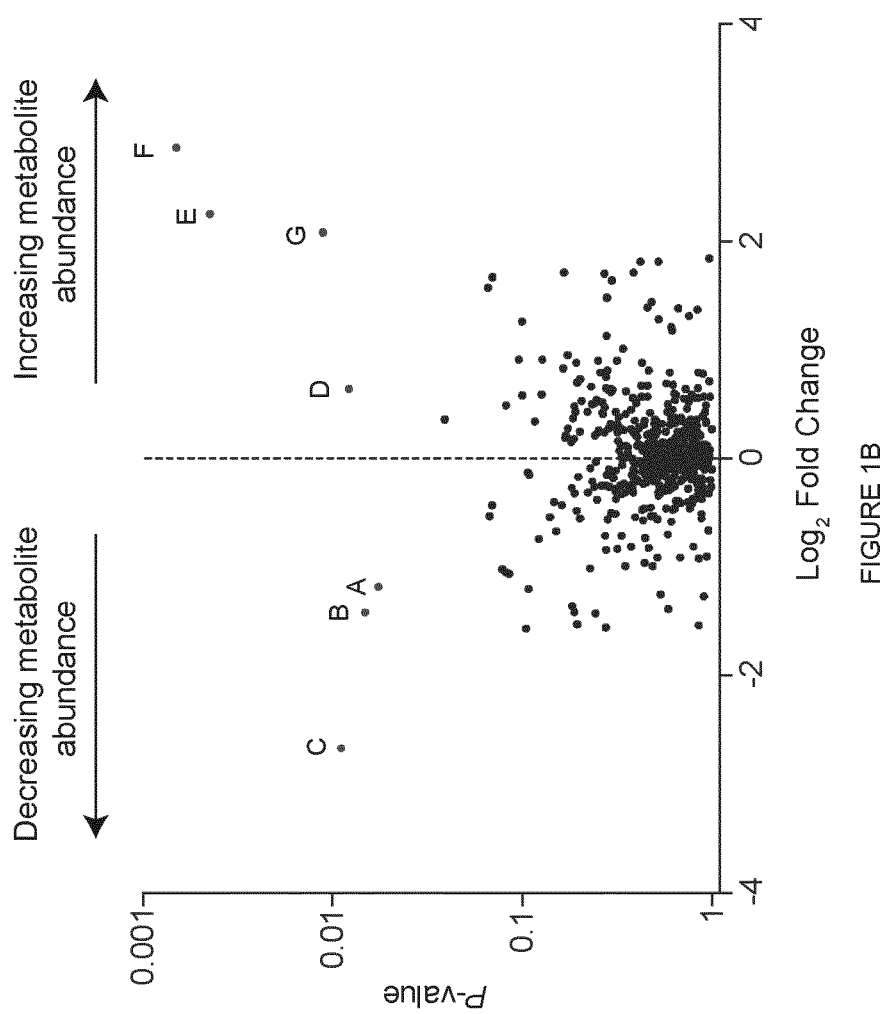
FIG. 1B shows the change in relative metabolite levels in the library after incubation with either 10 µg recombinant FAMIN or protein buffer control, in 100 µl phosphate-buffered saline (PBS) for 1 h at 37° C. Volcano plot with unadjusted P value and $\log_2$ fold change, grey dots labelled with letters indicate compounds whose abundance significantly decreased (candidate substrates; 'A'-'C') or increased (candidate products; 'D'-'F') in the presence of FAMIN (n=3 independent reactions).
Figure 1C:
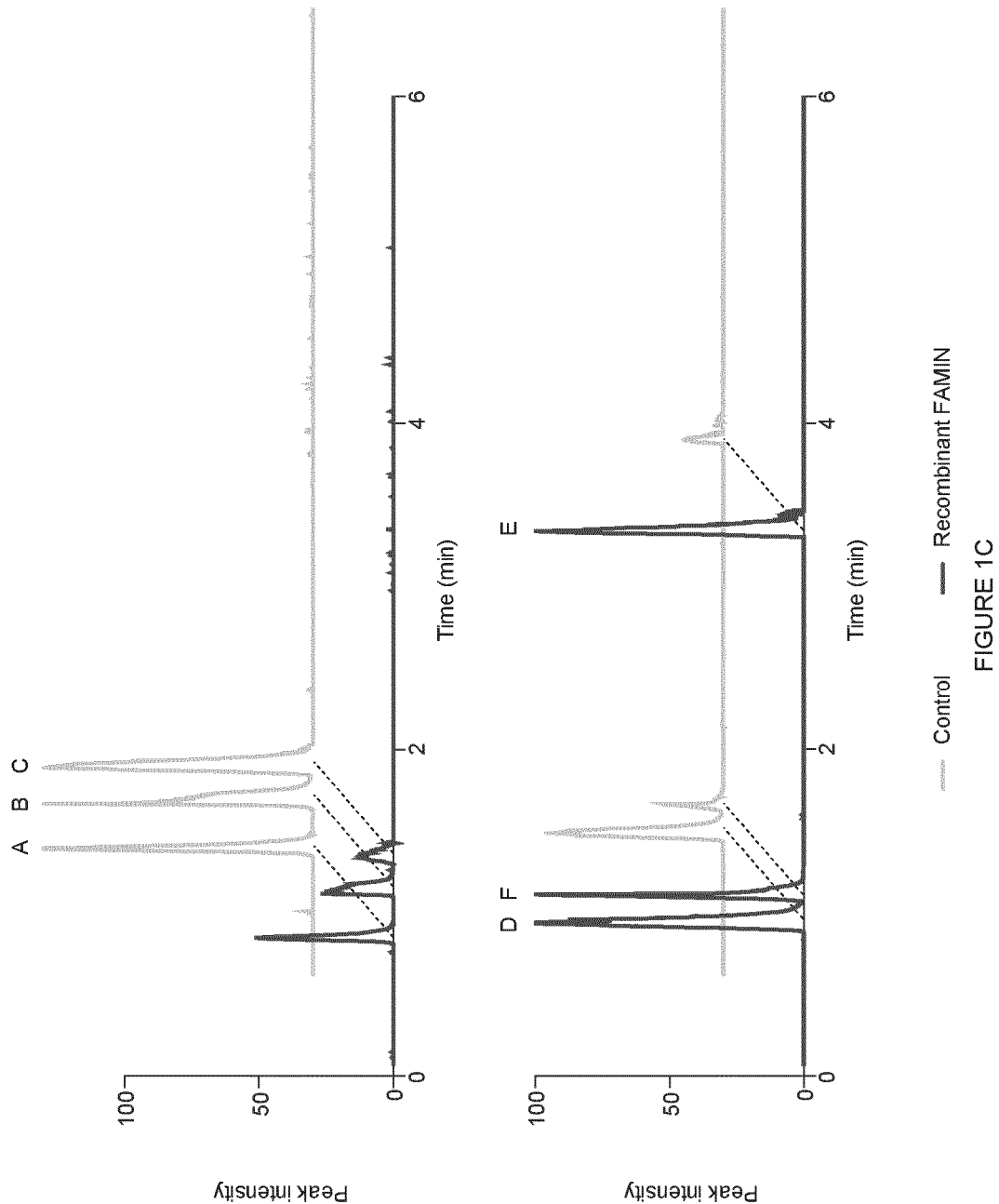
FIG. 1C shows representative extracted chromatograms for candidate substrates (upper) and products (lower) from FIG. 1B. Peak intensity of each extracted chromatogram of given m/z value was normalised to maximum level of 100.
Figure 1D:
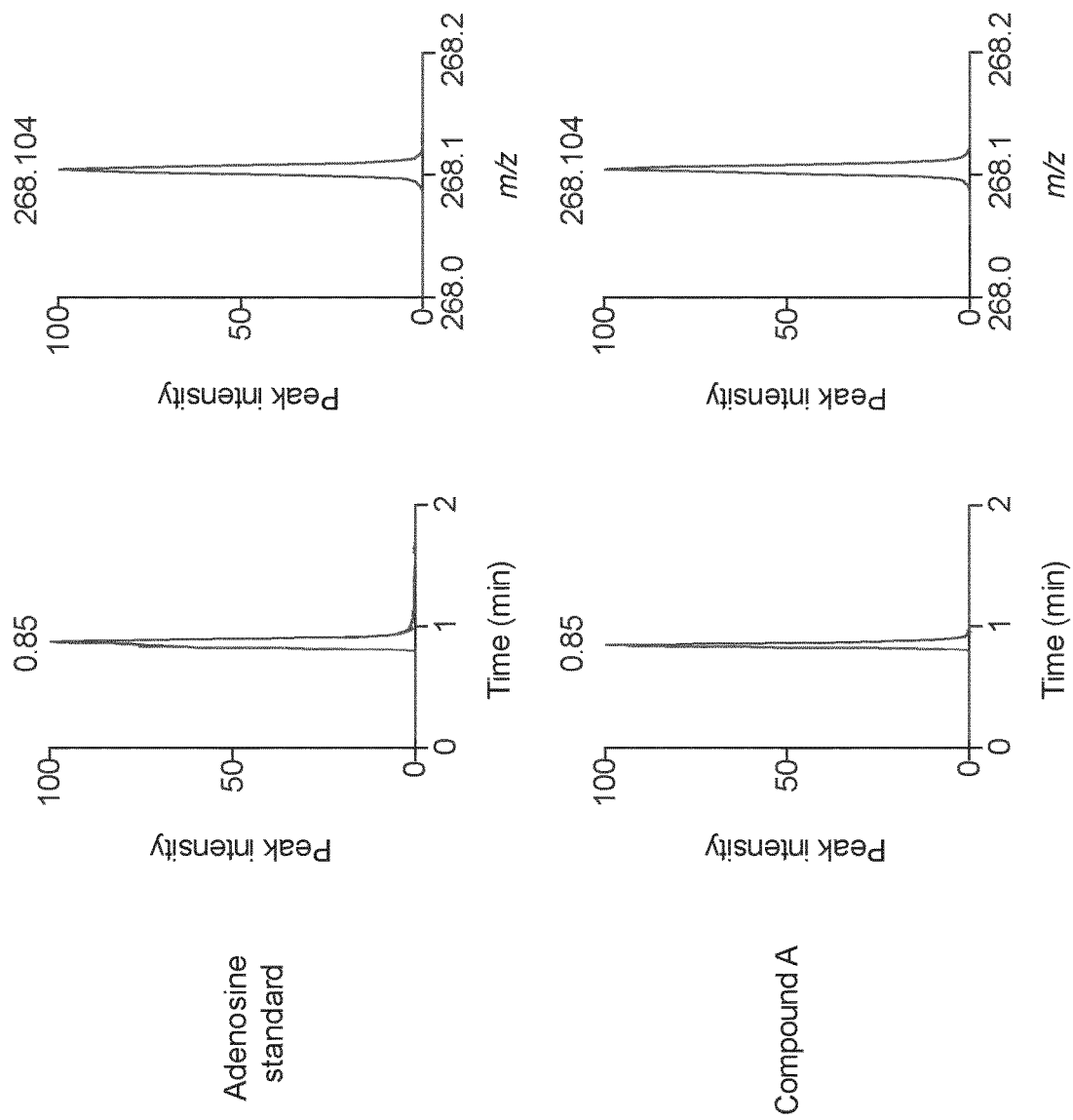
FIG. 1D shows representative mass spectra and extracted chromatograms for compound 'A' and corresponding standard for adenosine.
Figure 1E:
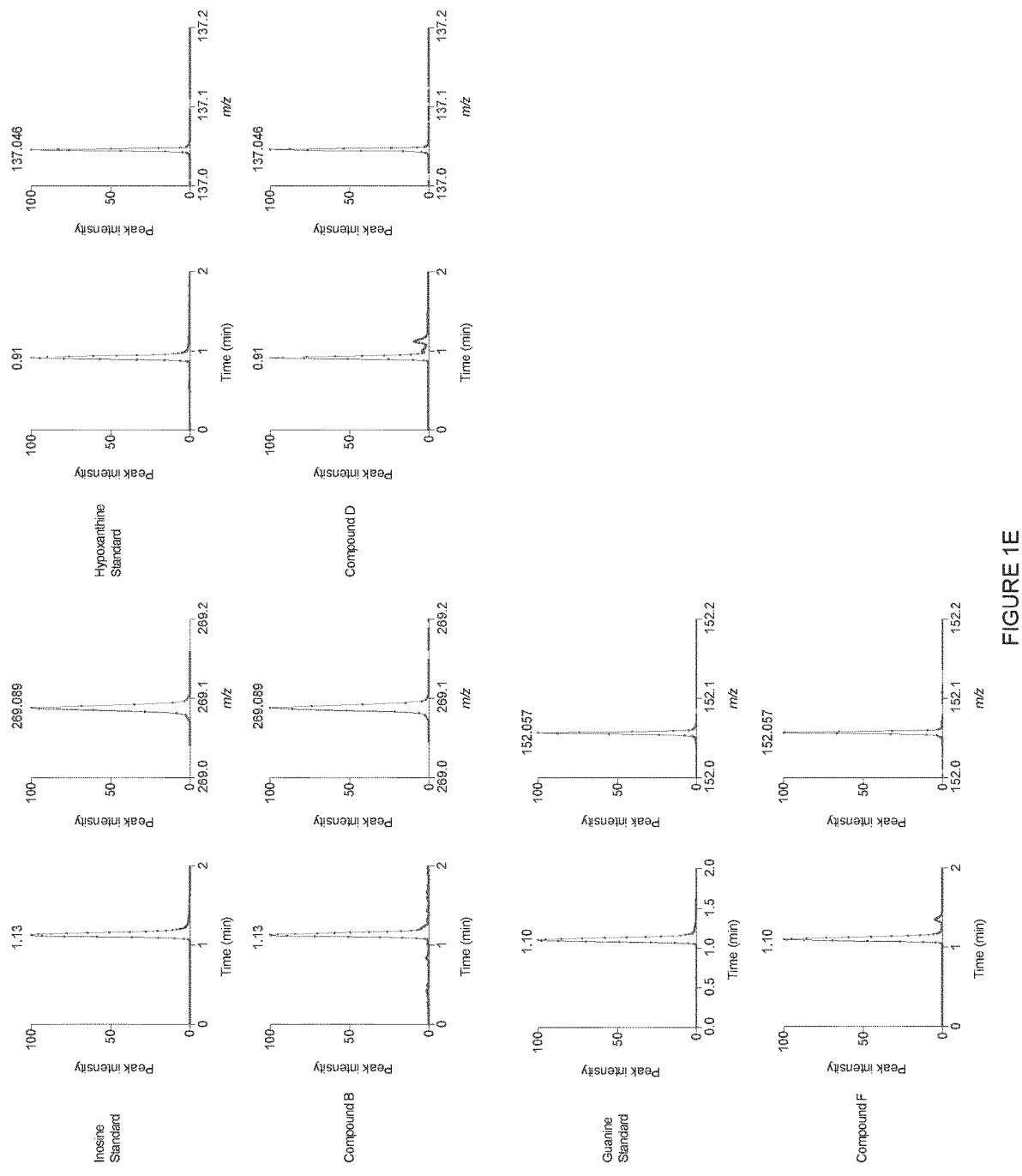
FIG. 1E shows representative mass spectra and extracted chromatograms for putative FAMIN-catalysed metabolites B, D and F, and corresponding standards for inosine, hypoxanthine and guanine.

We adopted bespoke, quantitative, high-sensitivity and high-resolution orthogonal liquid chromatography mass spectrometry (LC-MS) methodology to capture and accurately resolve a wide range of chemically highly diverse metabolites in aqueous extracts of FAMIN-silenced HepG2 cells. We identified over 25,000 unique LC-MS features in freeze-dried extracts across the different chromatography modalities and ionisation modes (FIG. 1A) and hypothesized that one or more of these might correspond to FAMIN substrates. We incubated 10 µg recombinant human FAMIN, or an equivalent volume of protein buffer control, with the metabolite library resuspended in a final reaction volume of 100 µl phosphate-buffered saline (PBS) pH 7.4 for 1 h at 37° C. After quenching the reaction, samples were re-extracted and only 3 and 4 compounds within the library were significantly decreased and increased, respectively, in the FAMIN-compared to the mock reaction (FIG. 1B, 1C).

Figure 1F:
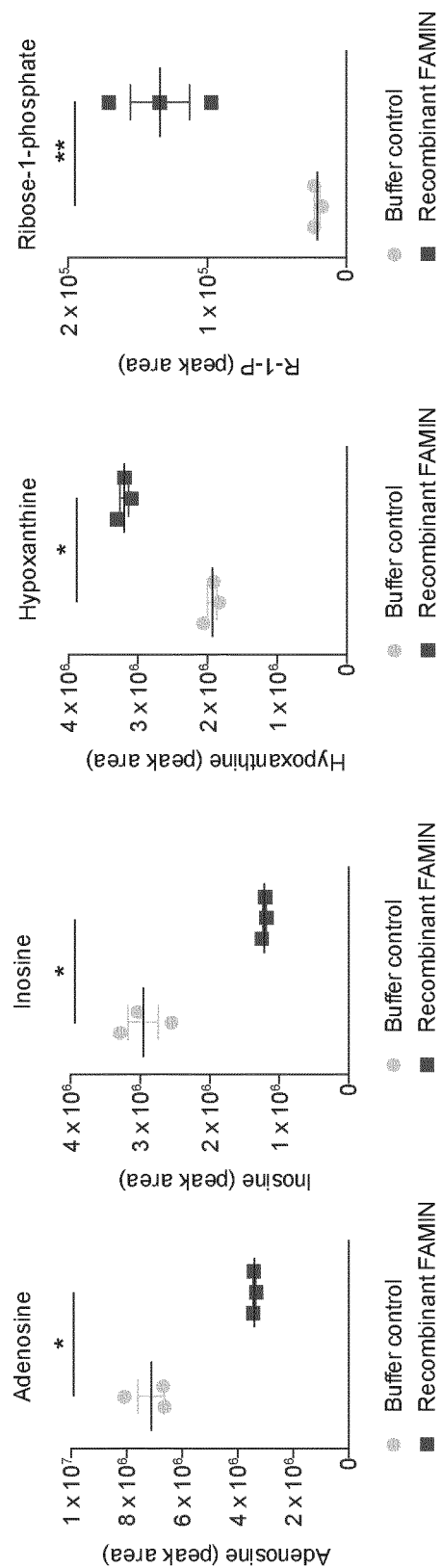
FIG. 1F shows abundance (area under chromatographic peak, normalised for total ion content) of adenosine, inosine, hypoxanthine and ribose-1-phosphate within the metabolomic library incubated with 10 µg recombinant FAMIN or protein buffer control (1 h, 37° C., PBS; n=3, mean±S.E.M.).
Figure 1G:
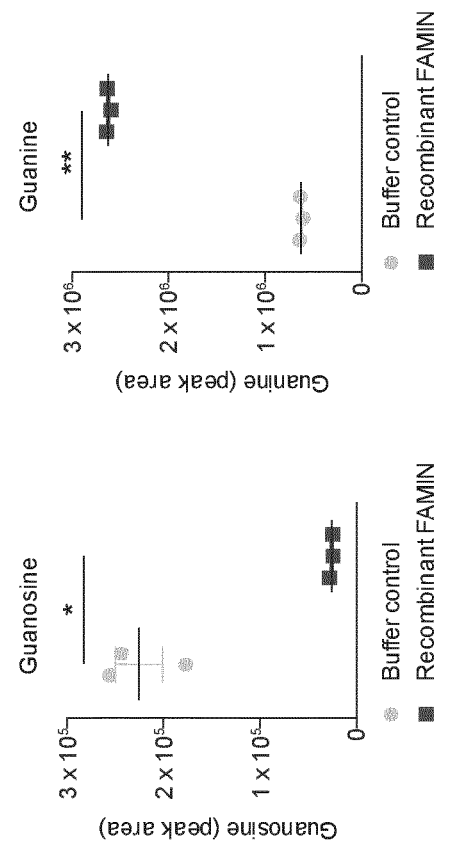
FIG. 1G shows guanosine and guanine levels following incubation of HepG2 cell aqueous extract with 10 µg recombinant FAMIN in 100 µl PBS. (n=3, mean±S.E.M.). *P<0.05 and **P<0.01 (unpaired, two-tailed Student's t-test).
Figure 1H:
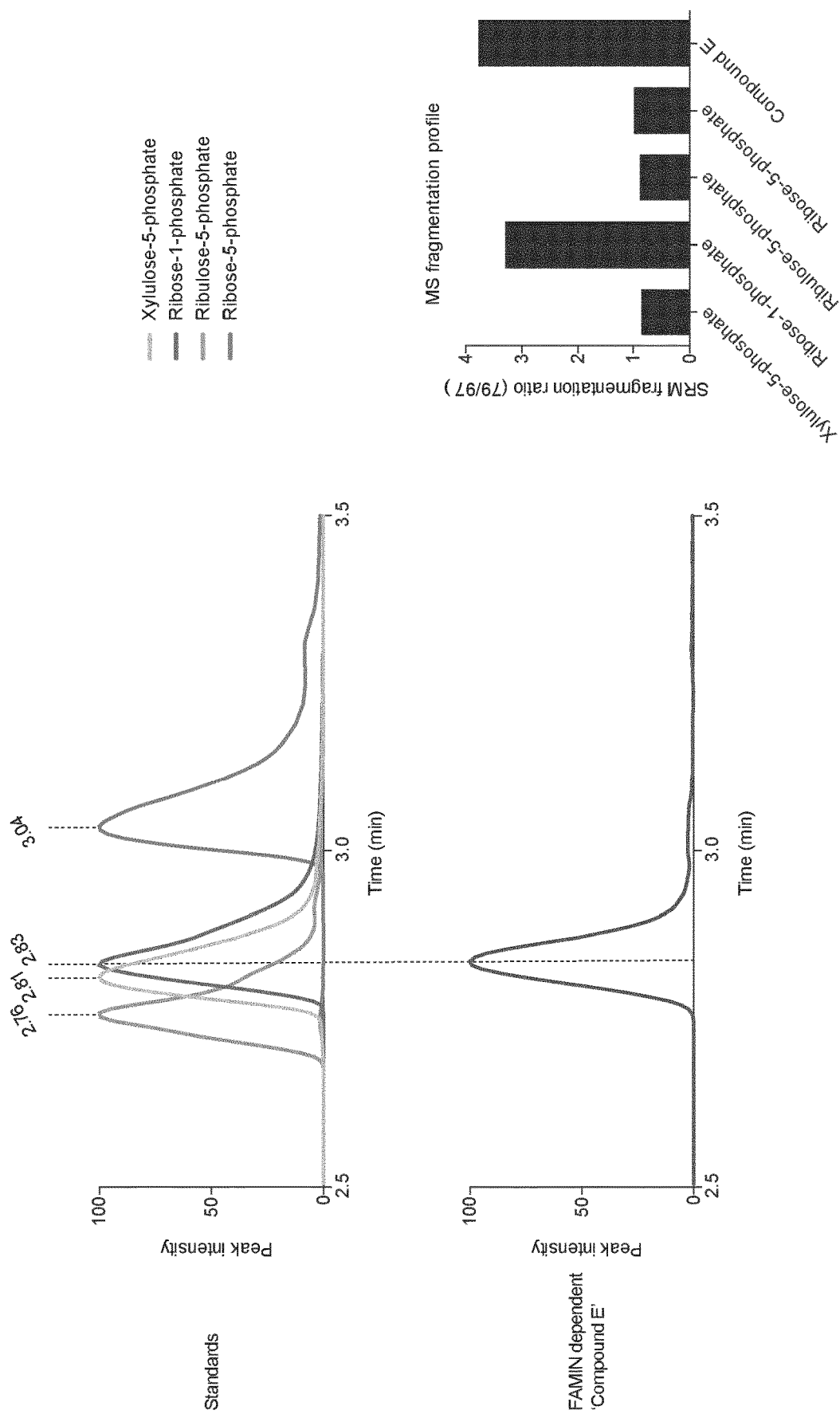
FIG. 1H shows on the left side representative extracted chromatograms for FAMIN-catalysed compound 'E' and corresponding standards for ribose-1-phosphate, ribose-5-phosphate, ribulose-5-phosphate and xylulose-5-phosphate. All measurements performed using a BEH amide HILIC column and TSQ Quantiva triple quadrupole. The right panel shows the ratio of selected reaction monitoring (SRM) daughter ions with nominal m/z values of 79 and 97.
Figure 1I:
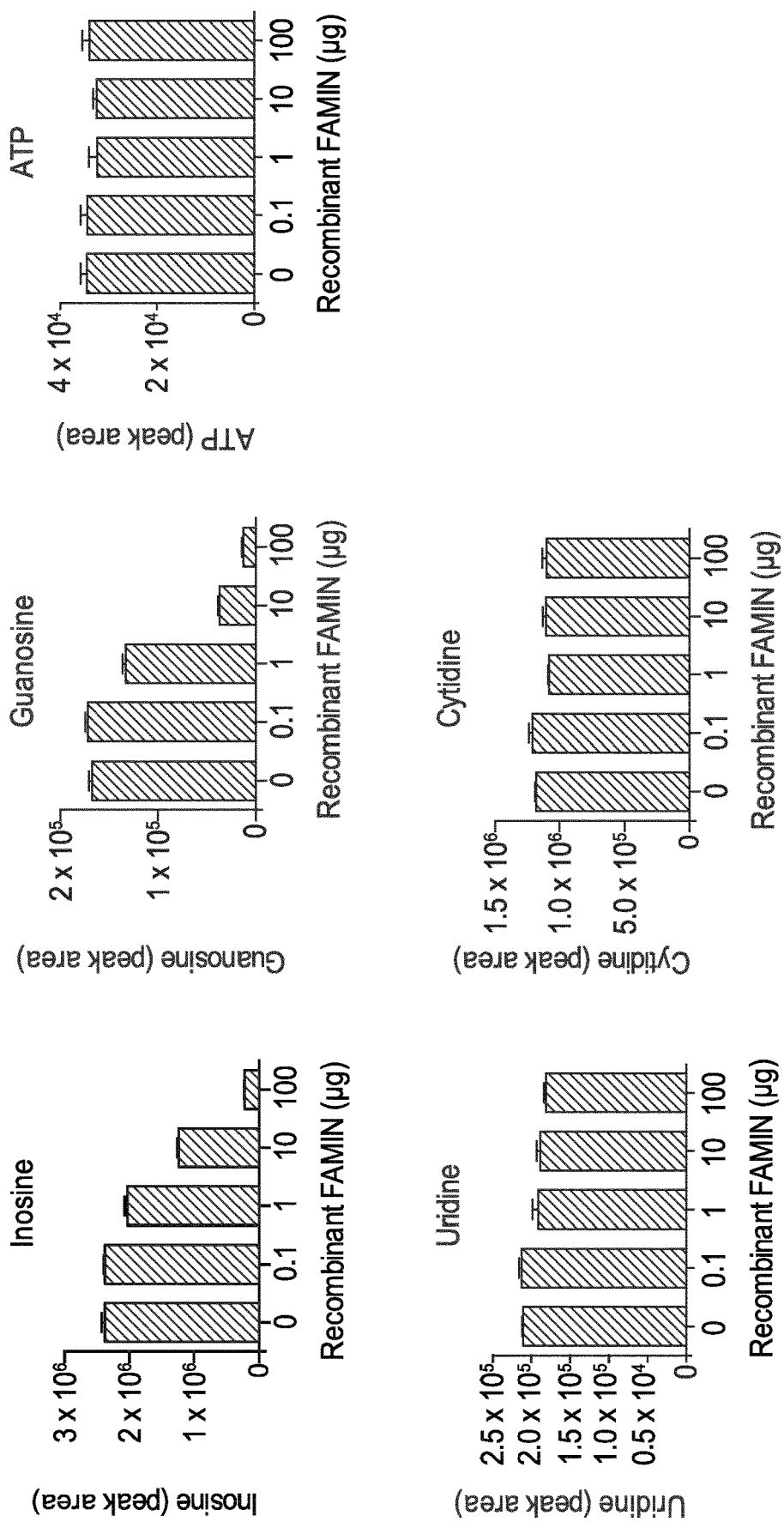
FIG. 1I shows inosine, guanosine, cytidine, uridine and ATP levels following incubation of 0.1, 1.0, 10.0 or 100.0 µg of recombinant FAMIN with the complete metabolomic library (aqueous phase of methanol:chloroform extract of HepG2 cells) in 100 µl PBS (n=3, mean±S.E.M.).

We next sought to elucidate the identities of these candidate substrates and products. We searched against the METLIN database, the m/z values {A: 268.104, B: 269.089, C: 284.099 in positive ESI} of the 3 LC-MS features within the screened library whose levels were reduced in the presence of recombinant FAMIN (FIG. 1B, 1C). Intriguingly, all three of these putative substrates, A-C, exactly matched purine nucleosides, and could not be matched to any other compound. Molecular formula determination, using accurate mass and supported by isotopic mass distribution, also indicated compounds A-C were purine nucleosides. However, m/z and molecular formulae alone could not discriminate their identity. Compound A, with formula $C_{10}H_{13}N_5O_4$, might correspond to either adenosine or deoxyguanosine. Comparing chromatography characteristics of the candidate metabolites A-C against nucleoside standards we demonstrated that the retention times exactly matched adenosine, guanosine and inosine (FIG. 1D, 1E), suggesting that FAMIN was an enzyme catabolising the major cellular purine nucleosides (FIG. 1F, G). Consistent with this, the m/z values of the LC-MS features, D-F (FIG. 1B, 1C), whose levels increased upon reaction with recombinant FAMIN {137.046, 152.057 in positive ESI and 229.012 in negative ESI} matched the purine nucleobases hypoxanthine, guanine and a pentose-phosphate, respectively (FIG. 1F, 1G). The other LC-MS feature, G, with m/z value of {153.041 in positive ESI} that was also increased in the screen corresponded to the purine nucleobase xanthine, though its absolute levels were extremely low. Modified chromatography allowed faithful separation of isomeric pentose-phosphate compounds and identified compound E as ribose-1-phosphate (FIG. 1H). FAMIN did not affect any other nucleosides or nucleotides, e.g. ATP nor pyrimidine metabolites such as cytidine or uridine that were also present in our metabolomics library (FIG. 1I). Furthermore, adenosine, inosine, and guanosine consumption increased with the amount of recombinant FAMIN present in the reaction (FIG. 1I, 1J). Altogether, this suggested that FAMIN may be an enzyme that acts upon purine nucleosides to generate purine nucleobases and ribose-1-phosphate.

Figure 2B:
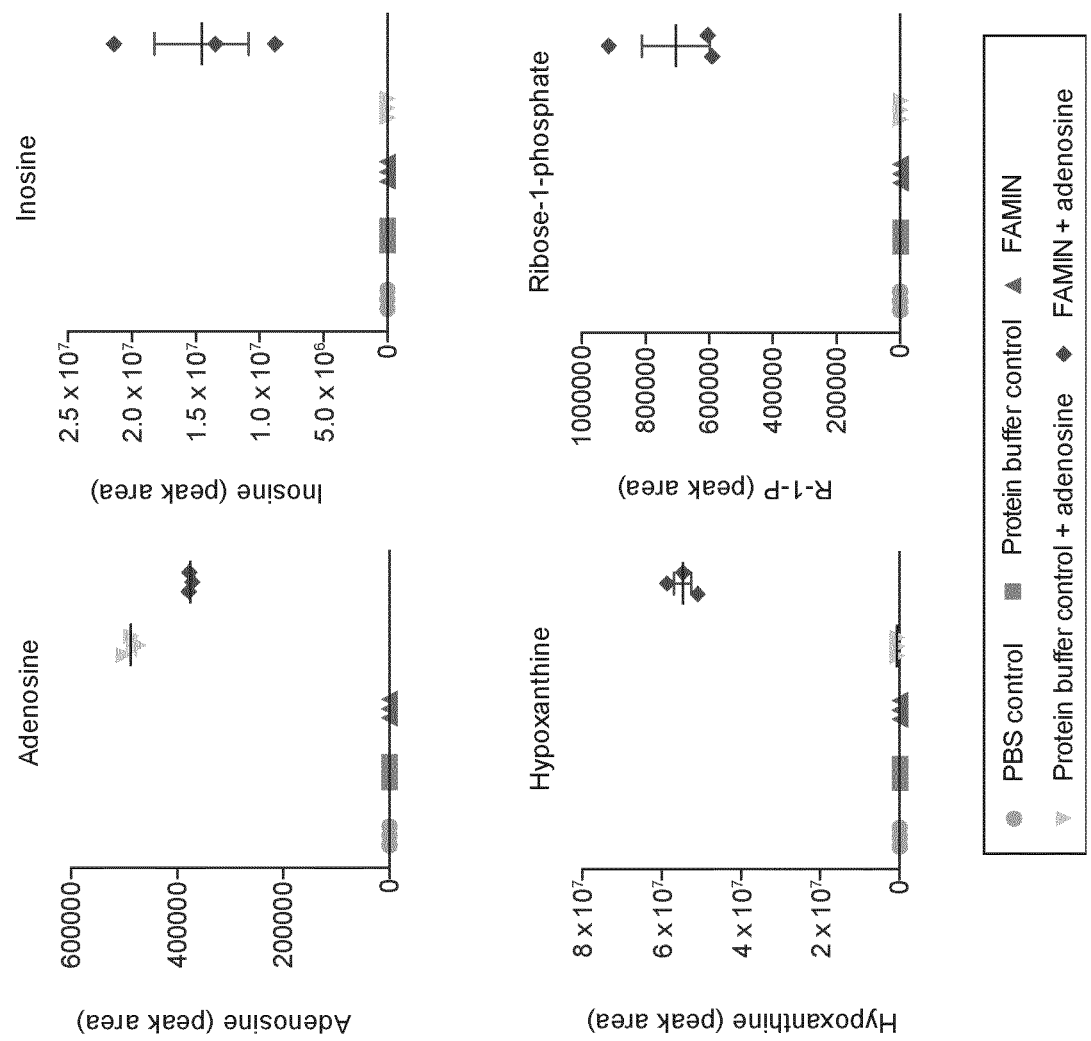
FIG. 2B shows adenosine, inosine, hypoxanthine and ribose-1-phosphate levels following incubation of 10 µg recombinant FAMIN or appropriate control with 100 µM adenosine as per FIG. 2A (n=3 each, mean±S.E.M.).
Figure 2C:
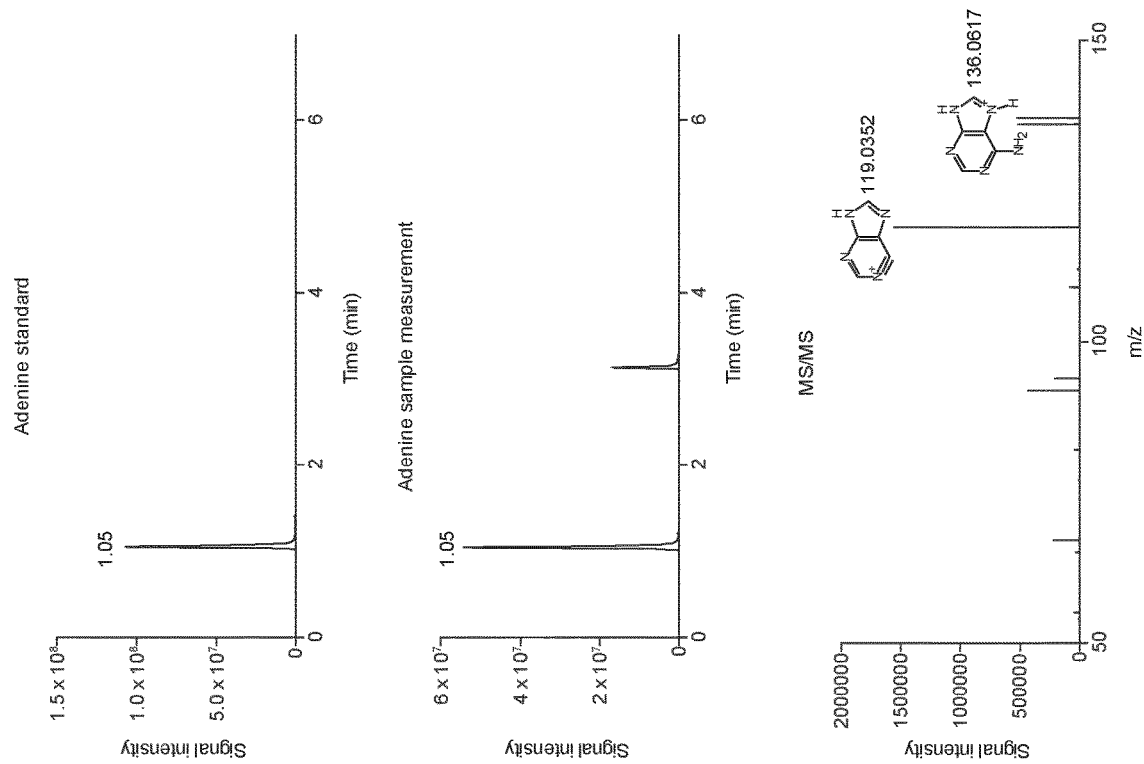
FIGS. 2C, 2D, 2E, and 2F show representative chromatograms and mass spectra for (2C) adenine, (2D) hypoxanthine, (2E) inosine and (2F) ribose-1-phosphate. Upper panels: (2C-E) extracted positive ion chromatogram showing injection of (2C) 1 µM standard of adenine; (2D) 5 µM standard of hypoxanthine; (2E) 5 µM standard of inosine on a BEH C8 column; (2F) extracted negative ion chromatogram showing injection of a 5 µg/mL standard of ribose-1-phosphate on a BEH amide HILIC column. All measurements performed using the Q Exactive Orbitrap and extracted at m/z values of (2C) adenine $[M+H]^+$: 136.0617, (2D) hypoxanthine $[M+H]^+$: 137.0457, (2E) inosine $[M+H]^+$: 269.0877 and (2F) ribose-1-phosphate $[M-H]^-$: 229.0119 at a tolerance of 2 ppm. Middle panels: Corresponding extracted chromatograms of a representative sample (10 µg recombinant FAMIN$^{254I}$ incubated with 10 µM adenosine for 1 h in 100 µl phosphate-buffered saline). Peaks at indicated retention times perfectly match those of adenine, hypoxanthine, inosine and ribose-1-phosphate standards. Lower panels: high resolution Fourier transform mass spectrometry (FTMS) mass spectrum of the representative FAMIN$^{254I}$ incubated sample during the peaks putatively identified as (2C) adenine, (2D) hypoxanthine, (2E) inosine, or (2F) ribose-1-phosphate. Nominal m/z values of (2C) 136, (2D) 137, (2E) 269 and (2F) 229, respectively, were selectively targeted and fragmented using a higher-energy collision dissociation (HCD) collision voltage of 25 eV to give the fragments shown.
Figure 2D:
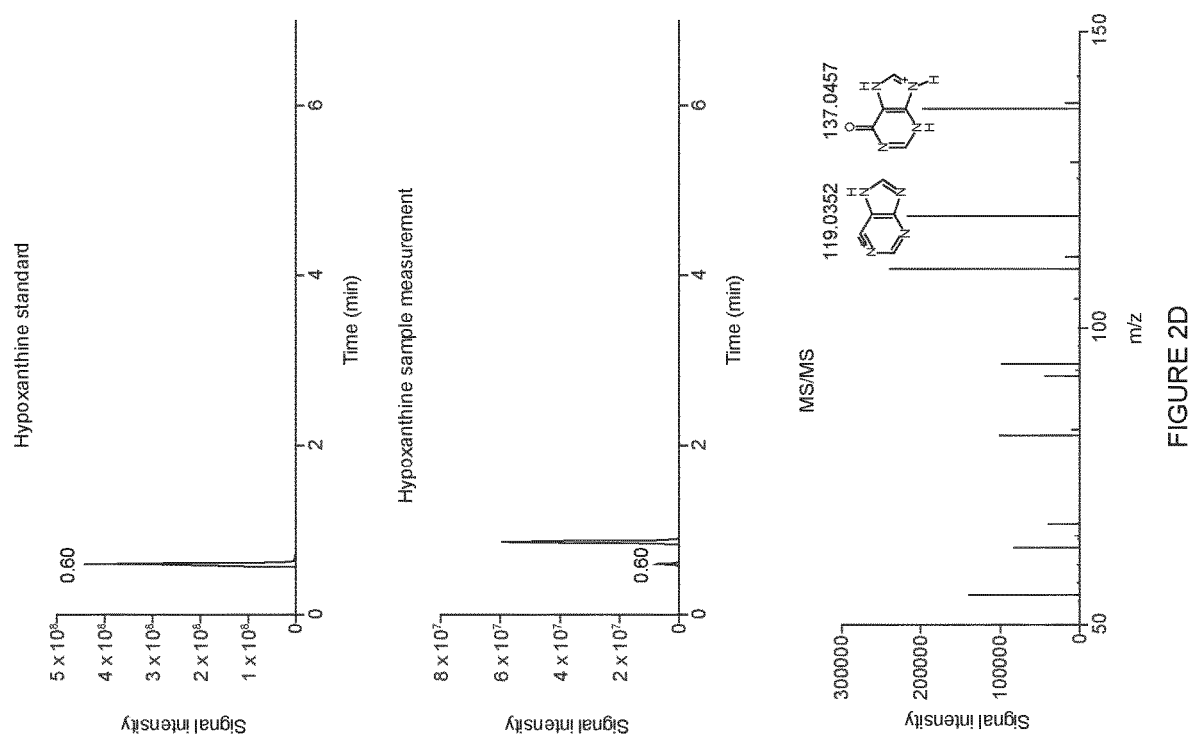
Figure 2E:
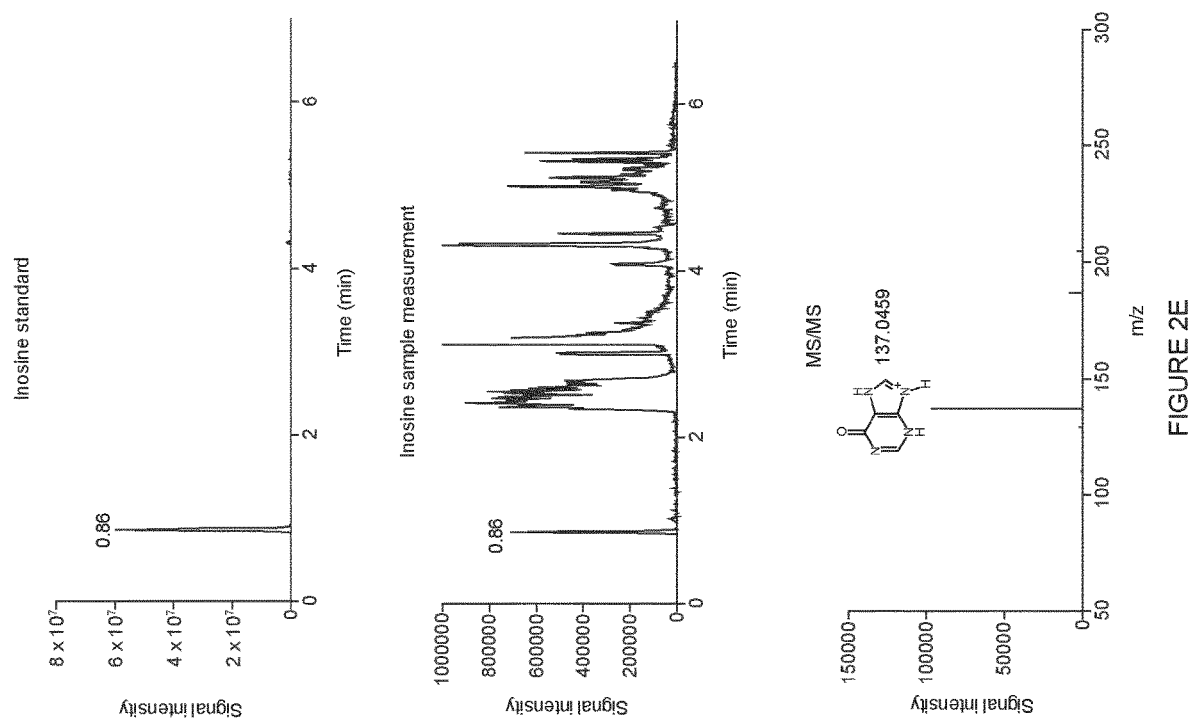
Figure 2F:
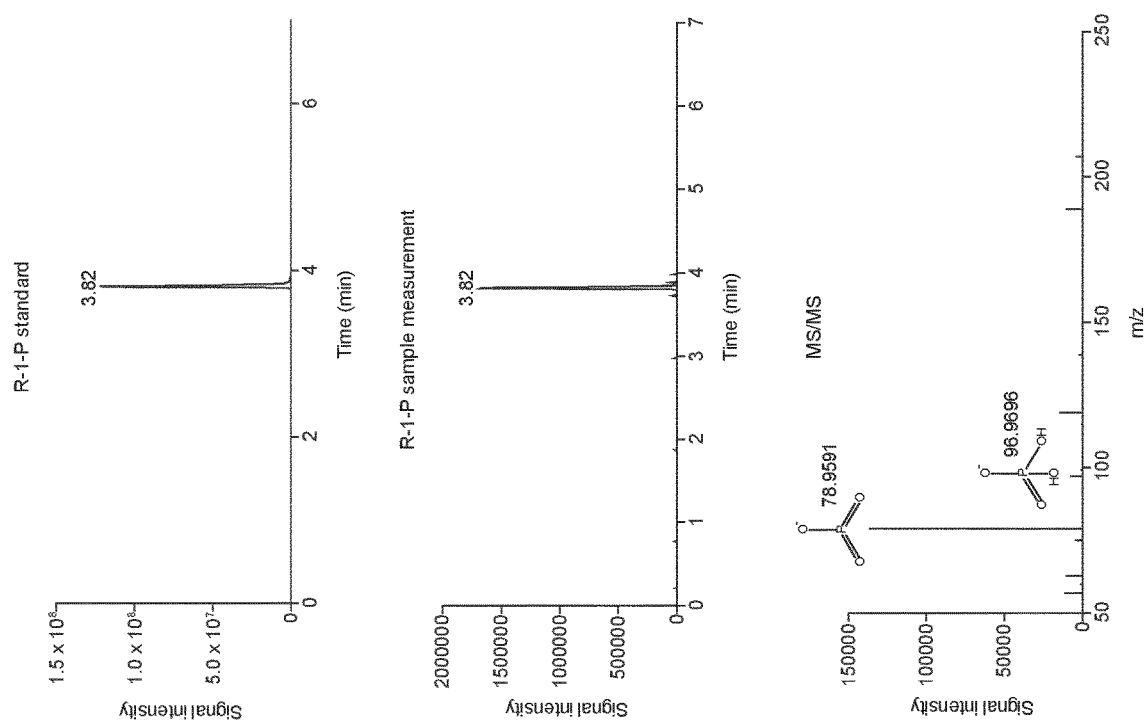
Figure 2G:
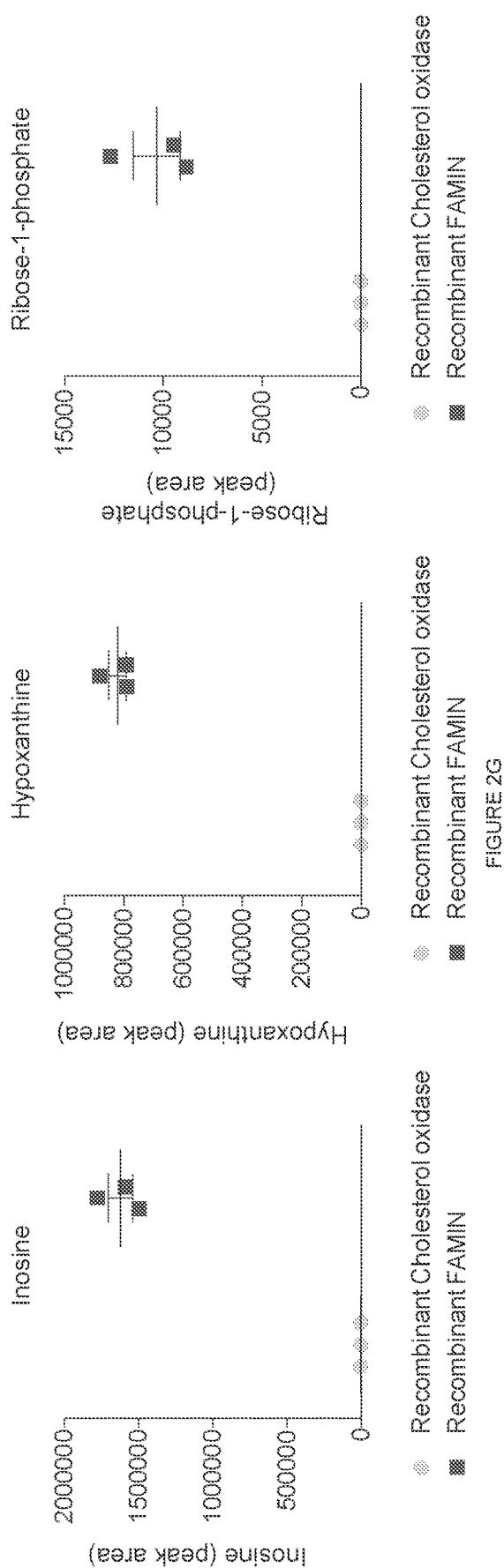
FIG. 2G shows inosine, hypoxanthine and ribose-1-phosphate levels following incubation of 10 µg recombinant FAMIN or equimolar cholesterol oxidase with 10 µM adenosine for 1 h in 100 µl PBS (n=3 each, mean±S.E.M.).
Figure 2I:
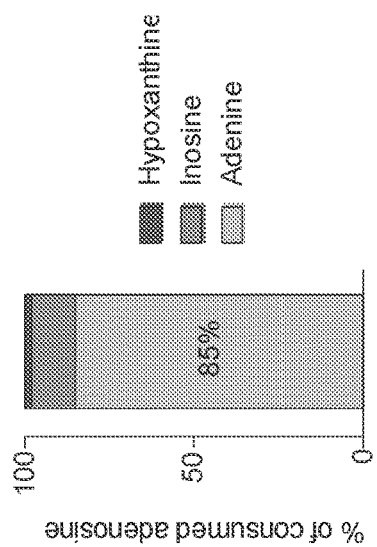
FIG. 2I shows fractional conversion of adenosine into adenine versus inosine versus hypoxanthine following incubation of 10 µg recombinant FAMIN with 10 µM adenosine for 1 h in 100 µl PBS. Calculated from absolute levels of hypoxanthine and inosine quantified using $^{13}C_2$, $^{15}N_1$-hypoxanthine and $^{15}N_4$-inosine internal standards, and adenine levels estimated using adenine external standard.
Figure 2J:
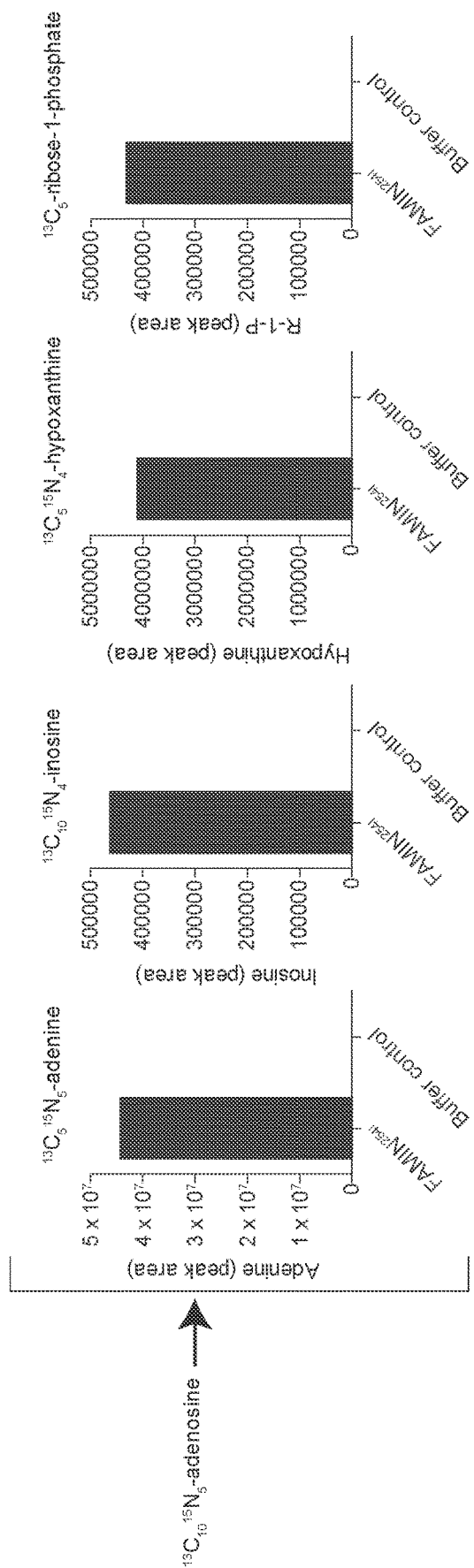
FIG. 2J shows detection of $[^{13}C_5^{15}N_5]$ adenine, $[^{13}C_{10}^{15}N_4]$ inosine, $[13c_5 15 N_4]$ hypoxanthine and $[^{13}C_5]$ ribose-1-phosphate levels following incubation of 10 µg recombinant FAMIN$^{254I}$ with 10 µM $[^{13}C_{10}^{15}N_5]$ adenosine for 1 h in 100 µl PBS (n=3 each, mean±S.E.M.).
Figure 2K:
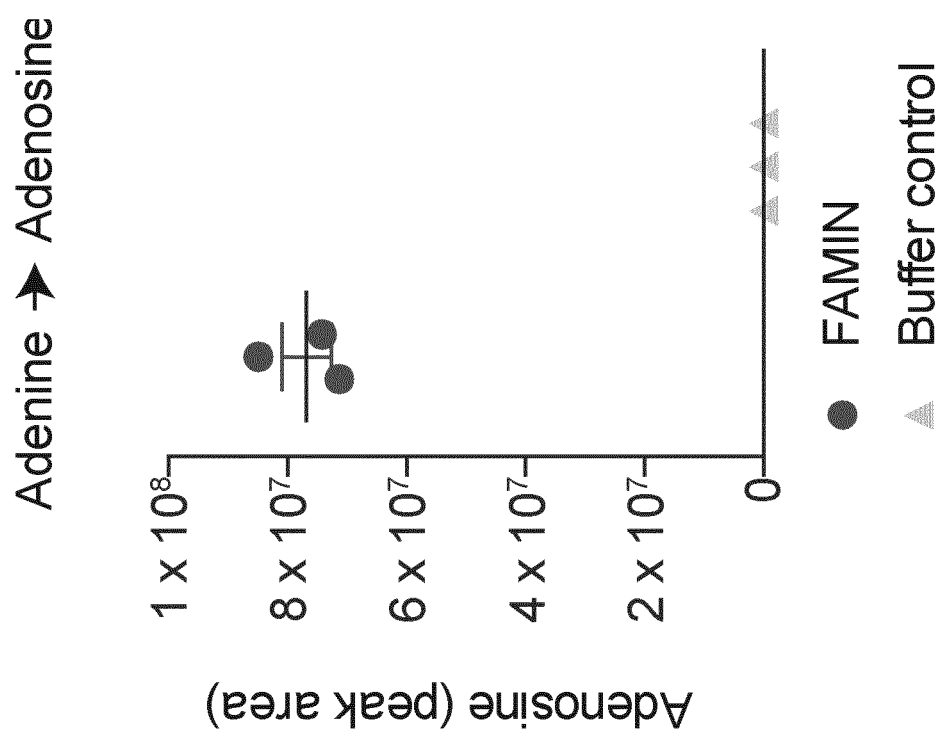
FIG. 2K shows adenosine levels in reactions of 50 µM adenine and 50 µM ribose-1-phosphate in 100 µl PBS in the presence of 10 µg FAMIN or control (1 h, 37° C.).
Figure 2L:
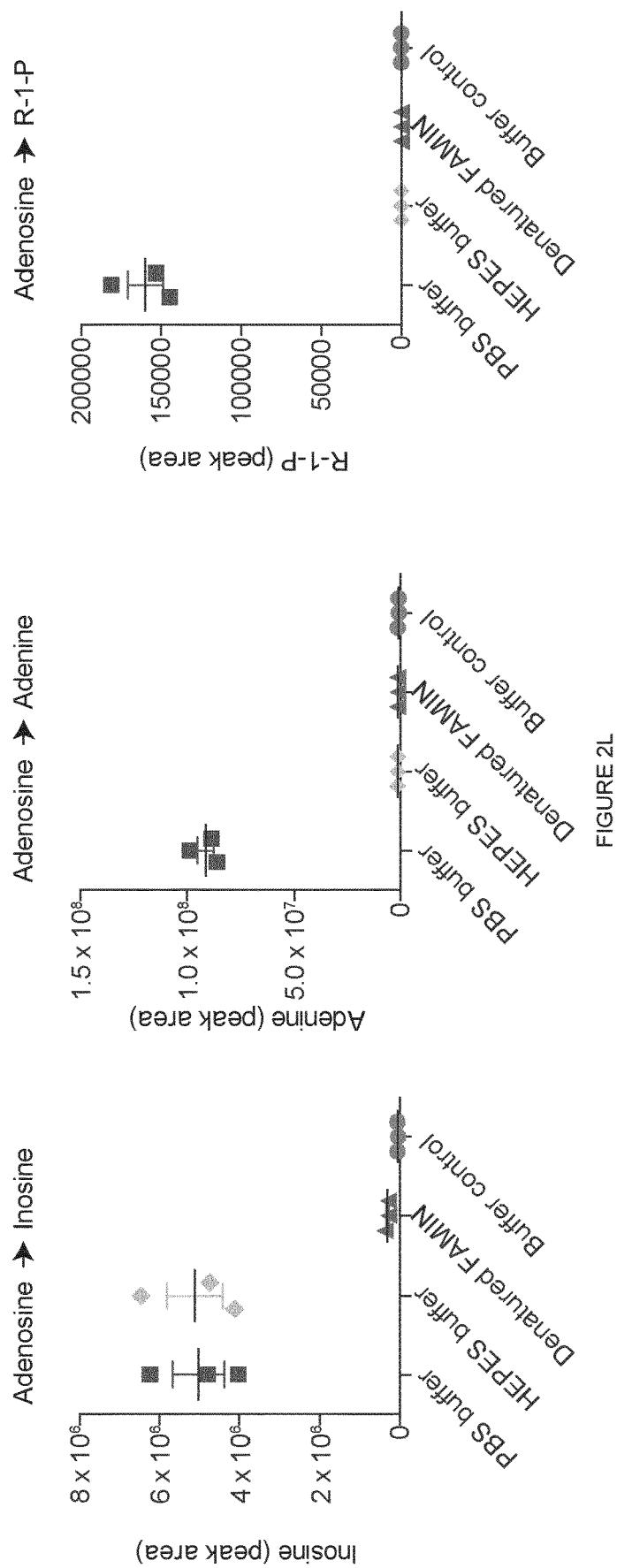
FIG. 2L shows adenine, inosine and ribose-1-phosphate levels following incubation of 10 µg recombinant FAMIN or appropriate controls, including heat-denatured recombinant FAMIN, with 10 µM adenosine for 1 h in 100 µl PBS or HEPES buffer (n=3, mean±S.E.M.).
Figure 2M:
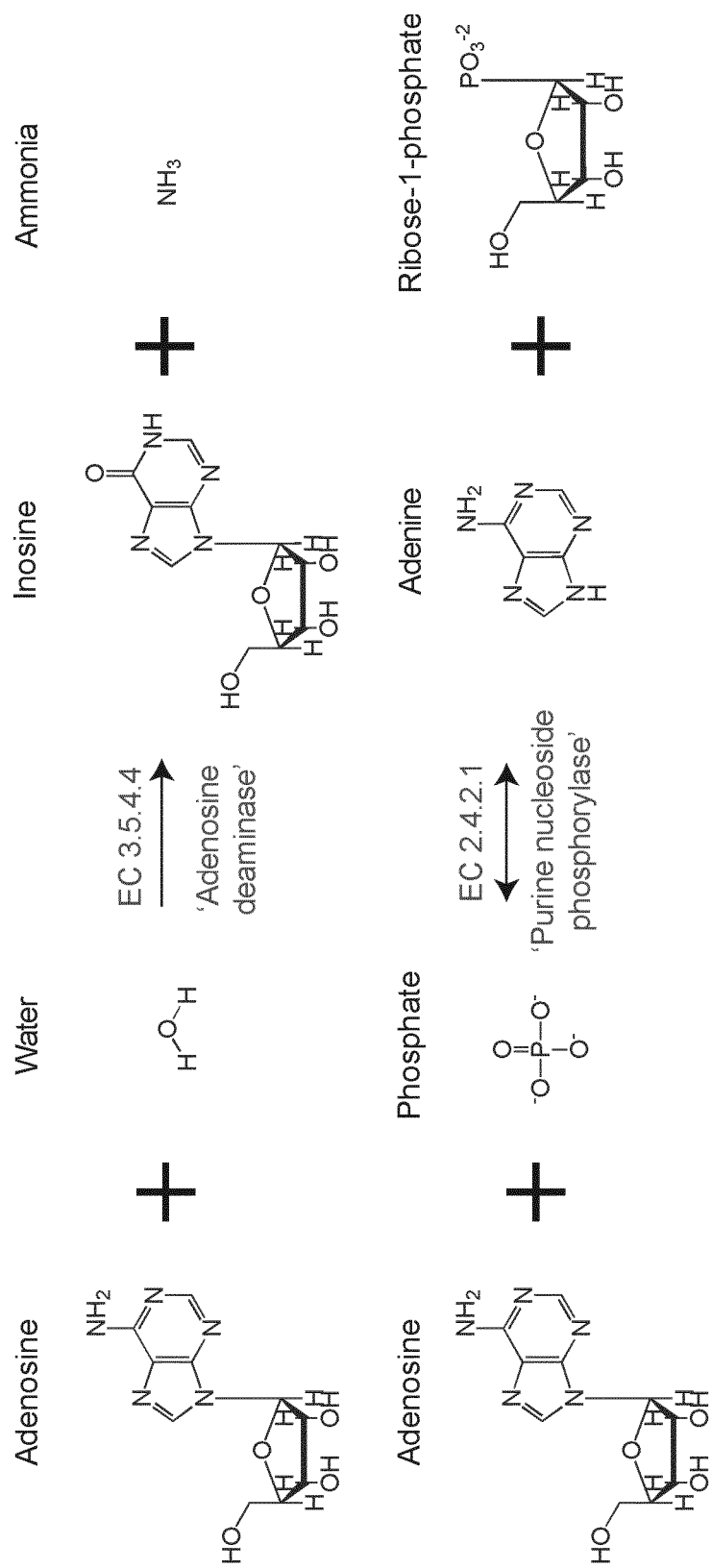
FIG. 2M shows FAMIN catalysed enzymatic reactions.

To unambiguously validate results from the library screen, we examined enzyme activity in a fully reductionist system using pure substrate, assayed with recombinant FAMIN in PBS at pH 7.4 and 37° C. FAMIN consumed adenosine and generated inosine, hypoxanthine and ribose-1-phosphate, confirmed by authentic standards (FIG. 2A, B, C, D, E, F). No spontaneous degradation of adenosine or formation of products in the absence of FAMIN or adenosine was observed (FIG. 2A, B), nor did equimolar amounts of an unrelated enzyme, cholesterol oxidase, generate inosine, hypoxanthine or ribose-1-phosphate (FIG. 2G). Since our orthogonal LC methods (HILIC and C18-PFP) did not resolve adenosine and adenine well, and adenosine undergoes source fragmentation to adenine, we included further chromatography methods to faithfully separate these two metabolites. This demonstrated that FAMIN also converted adenosine to adenine (FIG. 2H). Quantification indicated that ~85% of consumed adenosine was converted by FAMIN to adenine and ~15% to inosine (FIG. 2I). FAMIN-catalysed activities were further confirmed by tracing $[^{15}N_5^{13}C_{10}]$ adenosine-derived stable isotopes into reaction products (FIG. 2J). Incubating recombinant FAMIN with adenine and ribose-1-phosphate yielded adenosine, demonstrating the reaction can also operate in reverse, thereby also corroborating the identities of the products of the enzymatic forward reaction (FIG. 2K). FAMIN did not produce any other detectable products from adenosine, and heat-denaturing rendered the protein completely inactive (FIG. 2L). Consistent with FAMIN using inorganic orthophosphate ($P_i$) present in PBS to generate ribose-1-phosphate, the enzymatic reaction progressed only to inosine without producing adenine or ribose-1-phosphate when performed in HEPES buffer instead of PBS (FIG. 2L). We concluded that FAMIN exhibited two distinct enzymatic activities as adenosine deaminase (EC 3.5.4.4) and purine nucleoside phosphorylase (EC 2.4.2.1), and that reactions can proceed independently from each other (FIG. 2M).

Figure 2N:
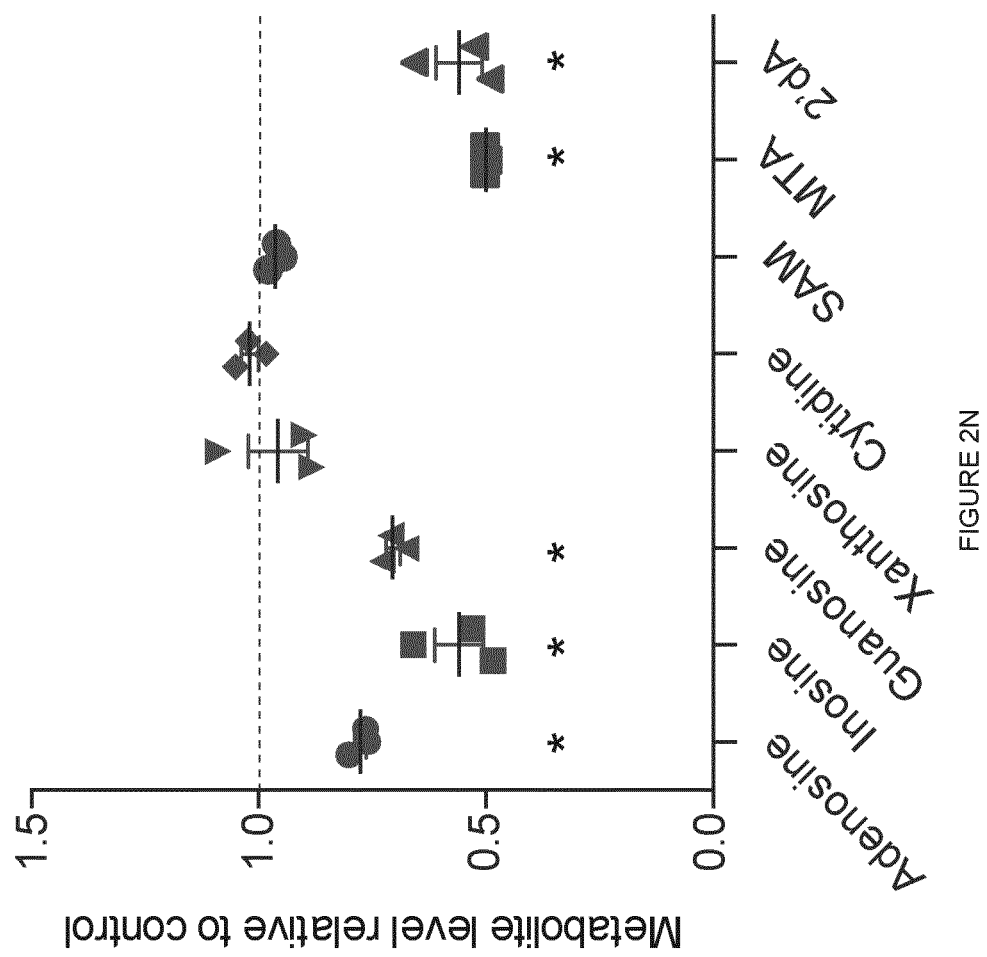
FIG. 2N shows specificity of FAMIN activity towards purine and pyrimidine nucleosides, measured as substrate (each added at 100 µM) consumption following incubation with 10 µg recombinant FAMIN or protein control in 100 µl PBS for 1 h at 37° C. (SAM; S-adenosylmethionine; MTA, S-methyl-5'-thioadenosine; 2'-dA, 2'-deoxyadenosine; n=3, mean±S.E.M.).
Figure 2O:
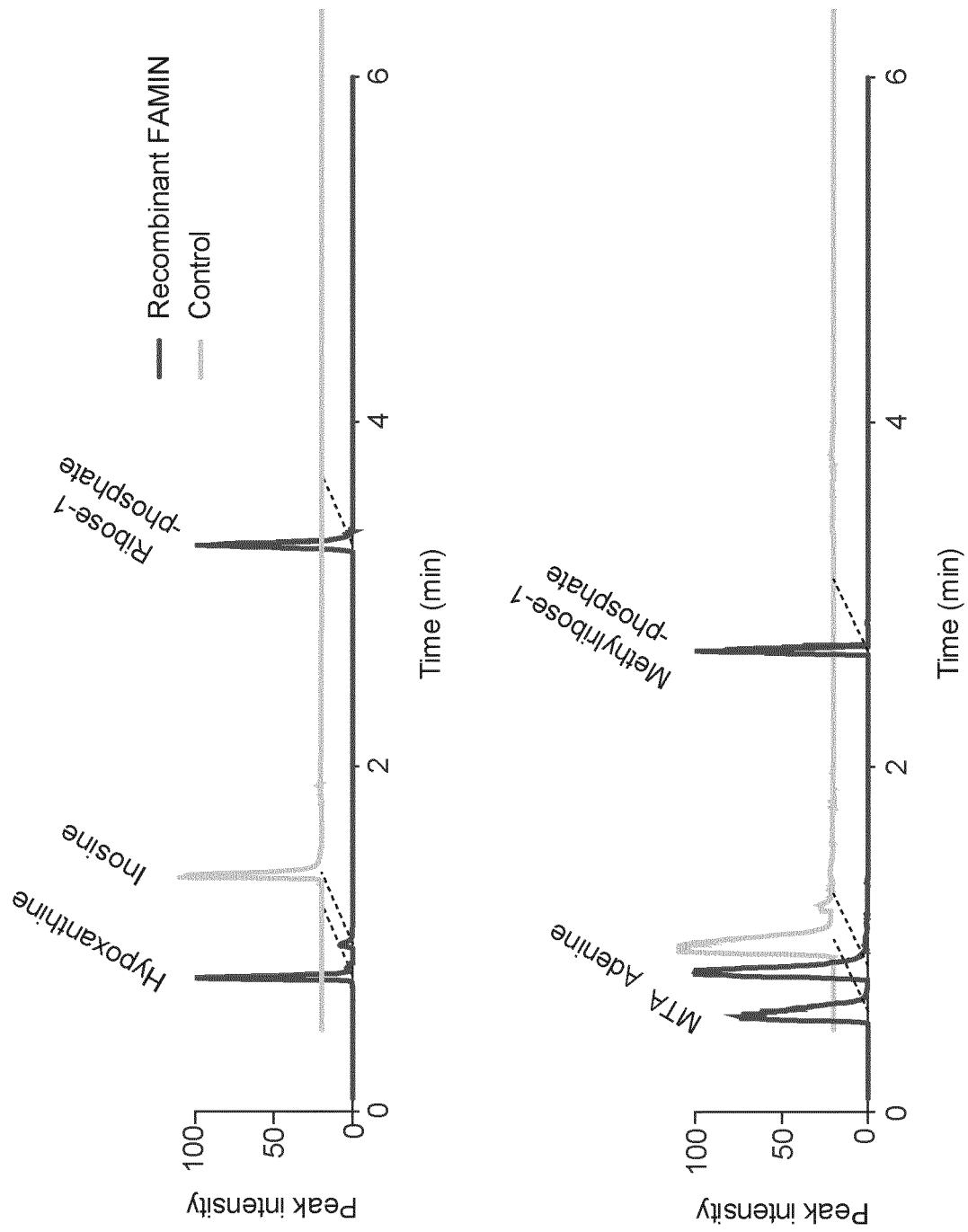
FIG. 2O shows representative extracted chromatograms for inosine, hypoxanthine and ribose-1- phosphate (upper chromatogram); and MTA, adenine and methylthioribose-1-phosphate (lower chromatogram) for reactions in FIG. 2N.
Figure 2R:
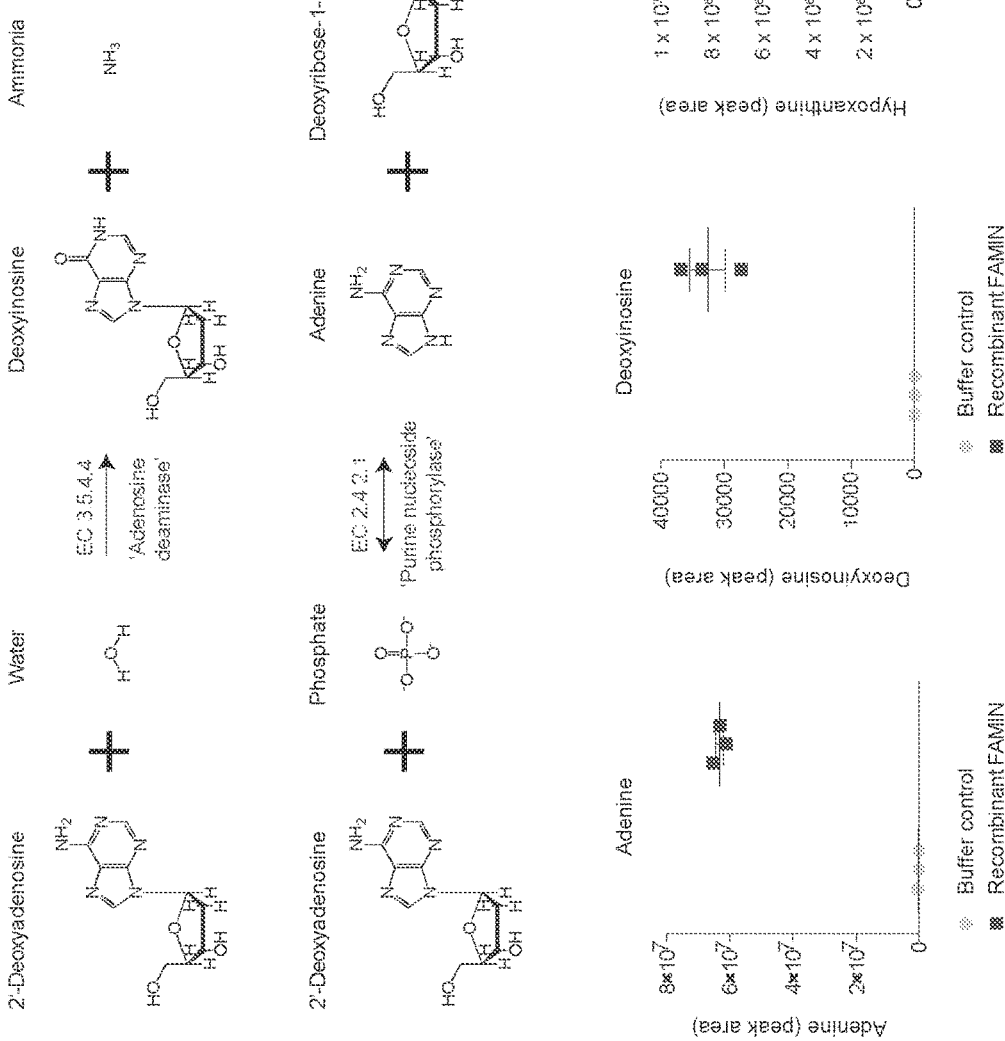
FIG. 2R shows on the upper panel FAMIN catalysed enzymatic reaction. On the lower panels adenine, 2'-deoxyinosine, hypoxanthine and deoxyribose-1-phosphate levels following incubation of 10 μg recombinant FAMIN or buffer control with 10 μM 2'deoxyadenosine for 1 h in 100 μl PBS (n=3 each, mean±S.E.M.).
Figure 2S:
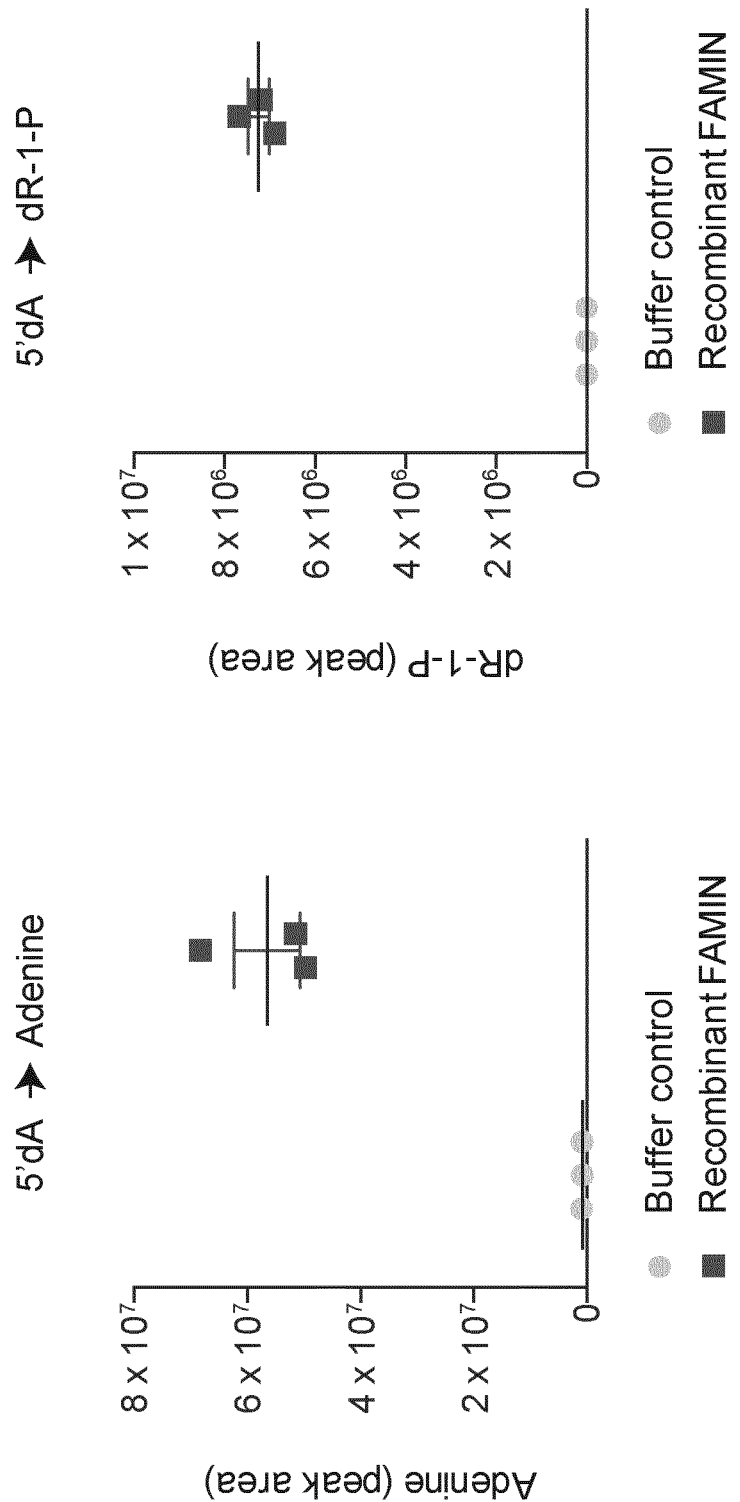
FIG. 2S shows adenine and deoxyribose-1-phosphate levels following incubation of 10 μg recombinant FAMIN or buffer control with 10 μM 5'deoxyadenosine (5'dA) for 1 h in 100 μl PBS (n=3 each, mean±S.E.M.).
Figure 2T:
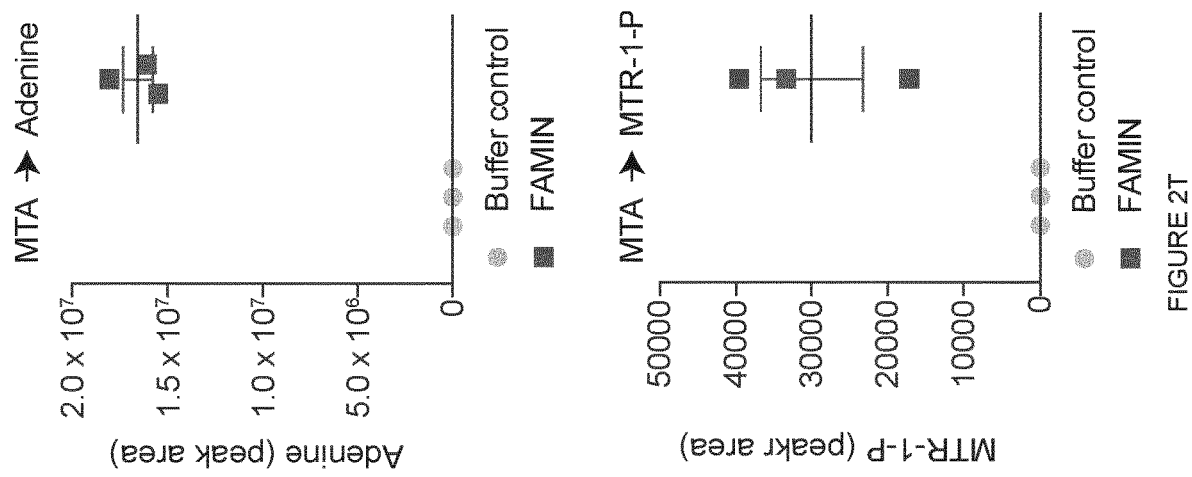
FIG. 2T shows adenine and methylthioribose-1-phosphate levels upon incubation of 100 μM MTA in PBS with recombinant FAMIN or buffer control for 1 h (n=3, mean±S.E.M.).
Figure 2V:
FIG. 2V shows further FAMIN catalysed enzymatic reaction. All metabolite level data in this figure measured as area under the chromatographic peak, normalised for total ion content. *P<0.05 (unpaired, two-tailed Student's t-test).

We next investigated FAMIN's activity spectrum with pure purine substrates. FAMIN metabolised pure inosine and guanosine, also identified in the library screen, into ribose-1-phosphate and their respective nucleobases, hypoxanthine and guanine (FIG. 2N, 2O, 2P, 2Q), consistent with purine nucleoside phosphorylase activity. No activity towards the pyrimidine cytidine was detected (FIG. 2N). FAMIN also metabolised 2'-deoxy-adenosine, producing adenine, 2'-deoxy-inosine, hypoxanthine, and 2'-deoxy-ribose-1-phosphate (FIG. 2N, 2R). 5'-deoxy-adenosine, a by-product of radical S-adenosylmethionine (SAM) enzymes (7), was also a substrate of FAMIN (FIG. 2S). FAMIN further metabolised S-methyl-5'-thioadenosine (MTA), though not SAM (FIG. 2N). MTA was not converted into S-methyl-5'-thioinosine and hypoxanthine as would be predicted from sequential adenosine deaminase and purine nucleoside phosphorylase activity, but into adenine and S-methyl-5'-thioribose-1-phosphate (FIG. 2O, 2T). Revisiting data from the library screen, we indeed observed a 50% reduction of MTA compared to baseline when 100 μg FAMIN was present in the 100 μl reaction volume (FIG. 2U). Hence this added a third activity of FAMIN as a S-methyl-5'-thioadenosine phosphorylase, EC 2.4.2.28 (FIG. 2V).

Figure 3A:
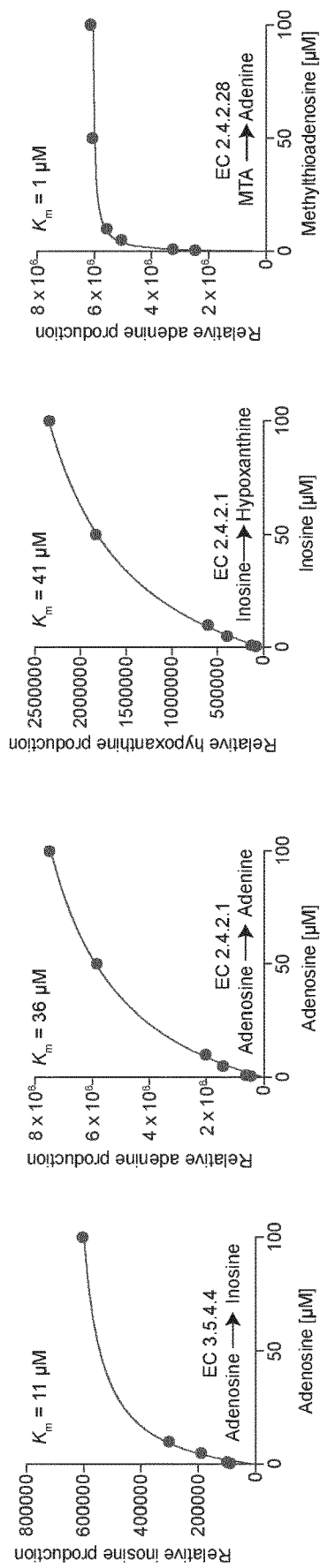
FIG. 3A shows Michaelis-Menten enzyme kinetics for FAMIN-dependent activities using a range of 500 nM to 100 μM adenosine, inosine and MTA as substrate. Activity measured as inosine, hypoxanthine and adenine production following incubation with protein for 1 h at 37° C. at pH 7.4.
Figure 3B:
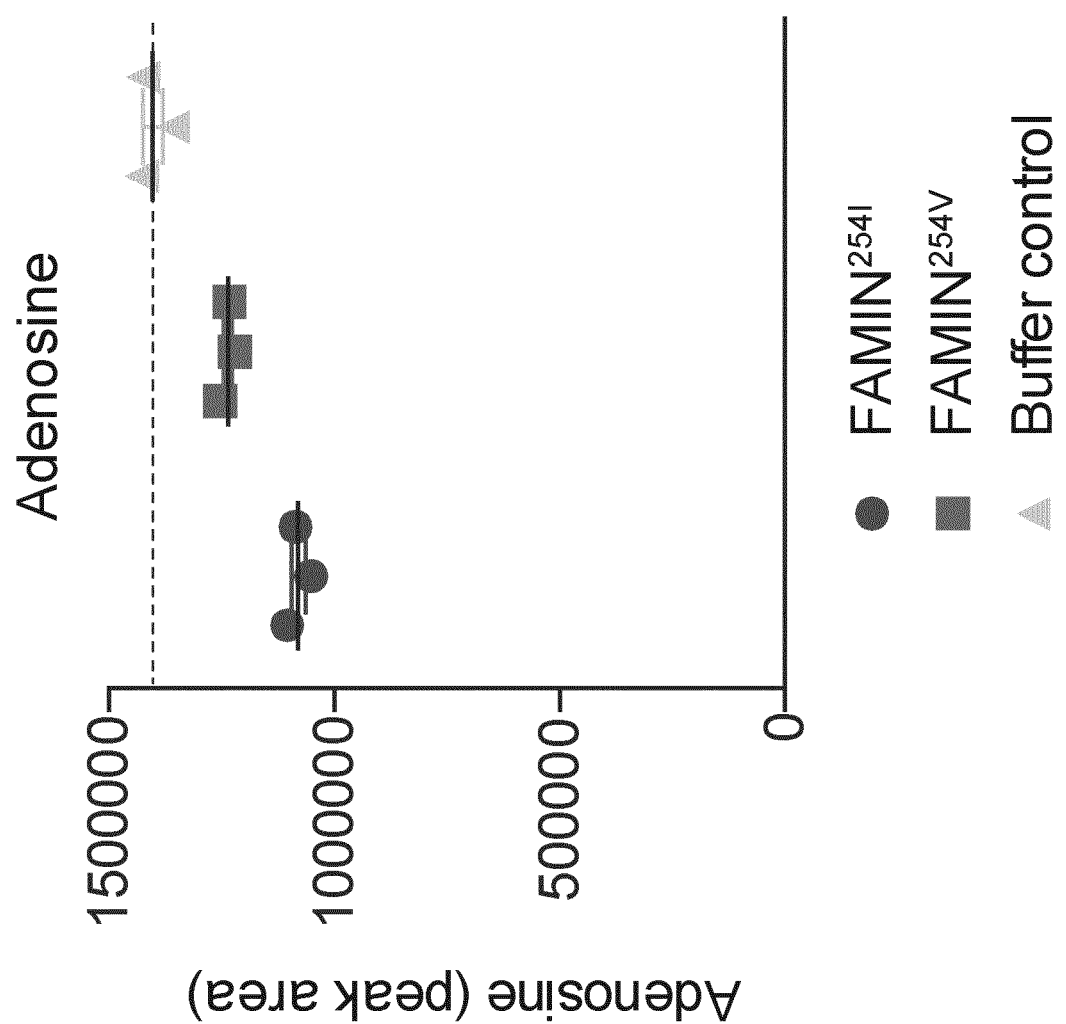
FIG. 3B shows consumption of adenosine and FIG. 3C production of adenine, inosine and ribose-1-phosphate following incubation of 10 μg recombinant FAMIN$^{254I}$, FAMIN$^{254V}$ or buffer control with 10 μM adenosine for 1 h in 100 μl PBS.
Figure 3C:
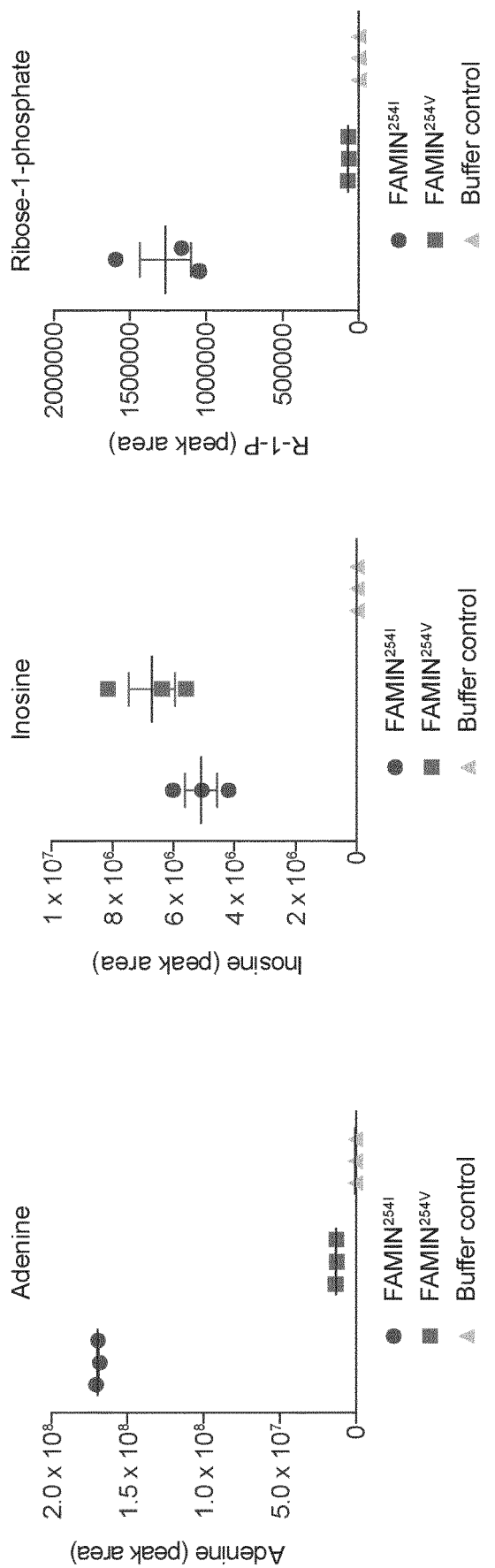
FIG. 3 shows the enzyme characteristics of the two FAMIN variants (FAMIN$^{254I}$ and FAMIN$^{254V}$) that are common in humans.
FIG. 3D shows hypoxanthine levels following incubation of 10 μg recombinant FAMIN$^{254I}$ or FAMIN$^{254V}$ with 10 μM adenosine for 1 h in 100 μl phosphate buffered saline (PBS), (n=3 each, mean±S.E.M.).
FIG. 3E shows fractional conversion of adenosine into adenine versus inosine versus hypoxanthine following incubation of 10 μM adenosine with 10 μg recombinant FAMIN$^{254I}$ or FAMIN$^{254V}$ for 1 h in 100 μl PBS.
FIG. 3F shows adenosine levels following incubation of 10 μg FAMIN$^{254I}$, FAMIN$^{254V}$ or control with 50 μM adenine and 50 μM ribose-1-phosphate for 1 h in 100 μl PBS.
FIG. 3G shows EC 2.4.2.1 (purine nucleoside phosphorylase) and EC 2.4.2.28 (MTA phosphorylase) activities of FAMIN$^{254I}$ and FAMIN$^{254V}$ as measured by hypoxanthine and adenine following incubation of recombinant protein with 10 inosine and methylthioadenosine (MTA), respectively, in PBS (n=3, mean±S.E.M.).
FIG. 3H shows inosine monophosphate (IMP), hypoxanthine and guanine levels in HEK293T cells 24 hours after transient transfection with FAMIN$^{254I}$, FAMIN$^{254V}$, FAMIN$^{284R}$ plasmids or empty vector (n=3, mean±S.E.M.).
FIG. 3I shows adenosine, inosine and guanosine levels in HEK293T cells 24 hours after transient transfection with FAMIN$^{254I}$, FAMIN$^{254V}$, FAMIN$^{284R}$ plasmids or empty vector (n=3, mean±S.E.M.).
FIG. 3J shows IMP levels in control and FAMIN silenced HepG2 cells 24 h after transfection (n=3, mean±S.E.M.).
FIG. 3K shows inosine and hypoxanthine levels in control and FAMIN silenced HepG2 cells 48 h after transfection (n=6, mean±S.E.M.). *P<0.05, P<0.01 and *P<0.001 (unpaired, two-tailed Student's t-test).
FIG. 3L shows guanosine and S-methyl-5'-thioadenosine levels in control and FAMIN silenced HepG2 cells 48 h after transfection (n=6, mean±S.E.M.). ***P<0.001 (unpaired, two-tailed Student's t-test).
Figure 3D:
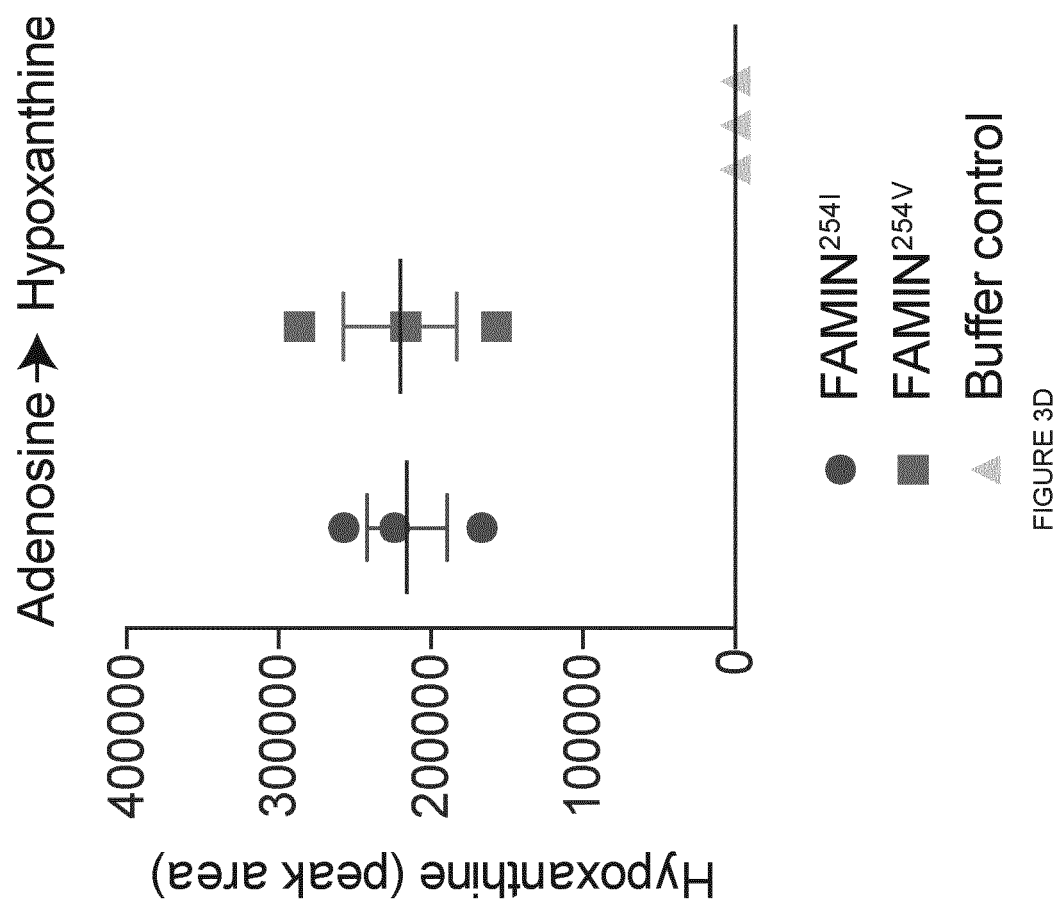
Figure 3E:
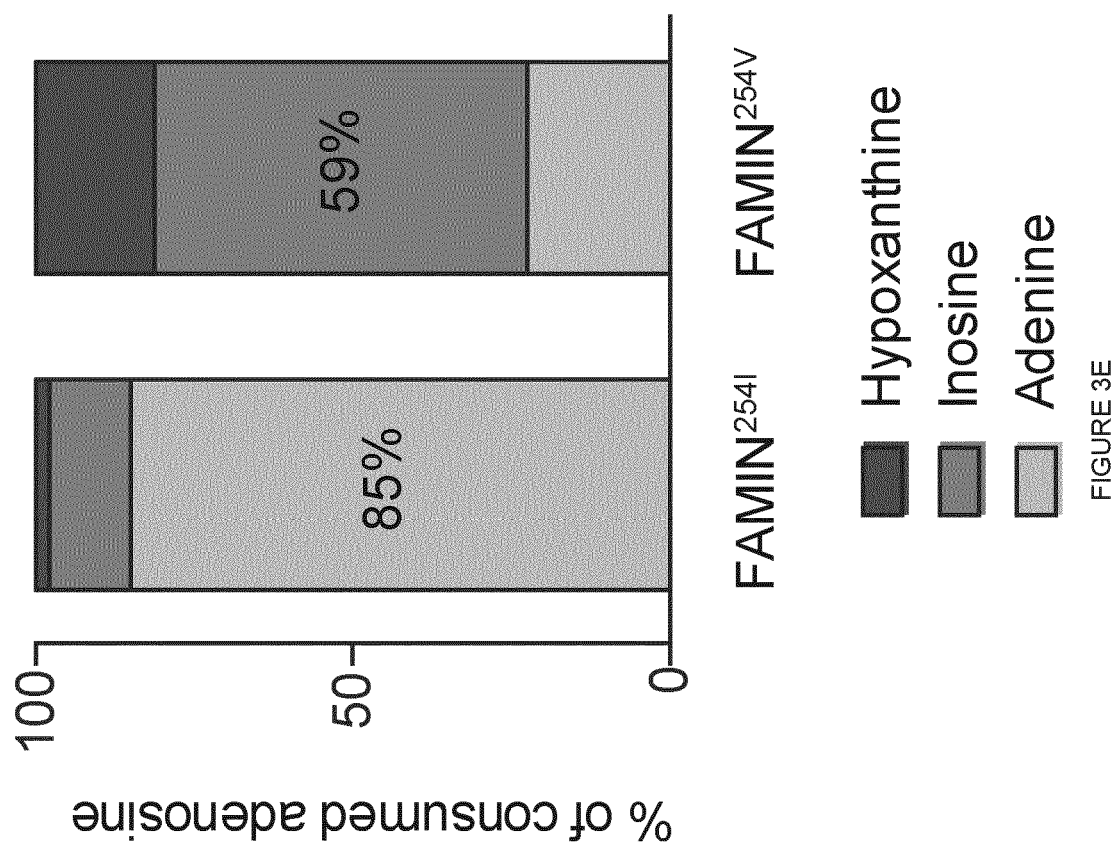
Figure 3F:
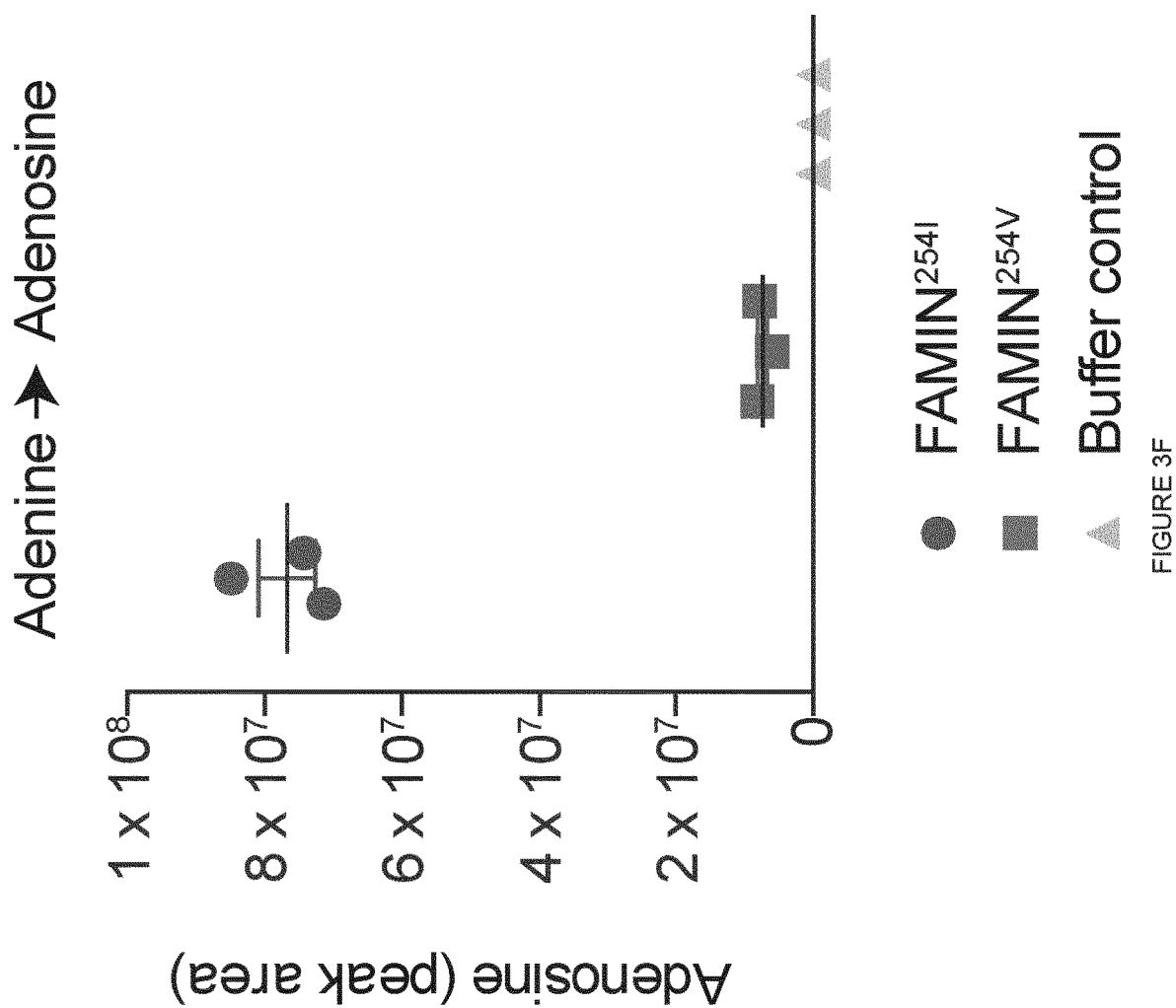
Figure 3G:
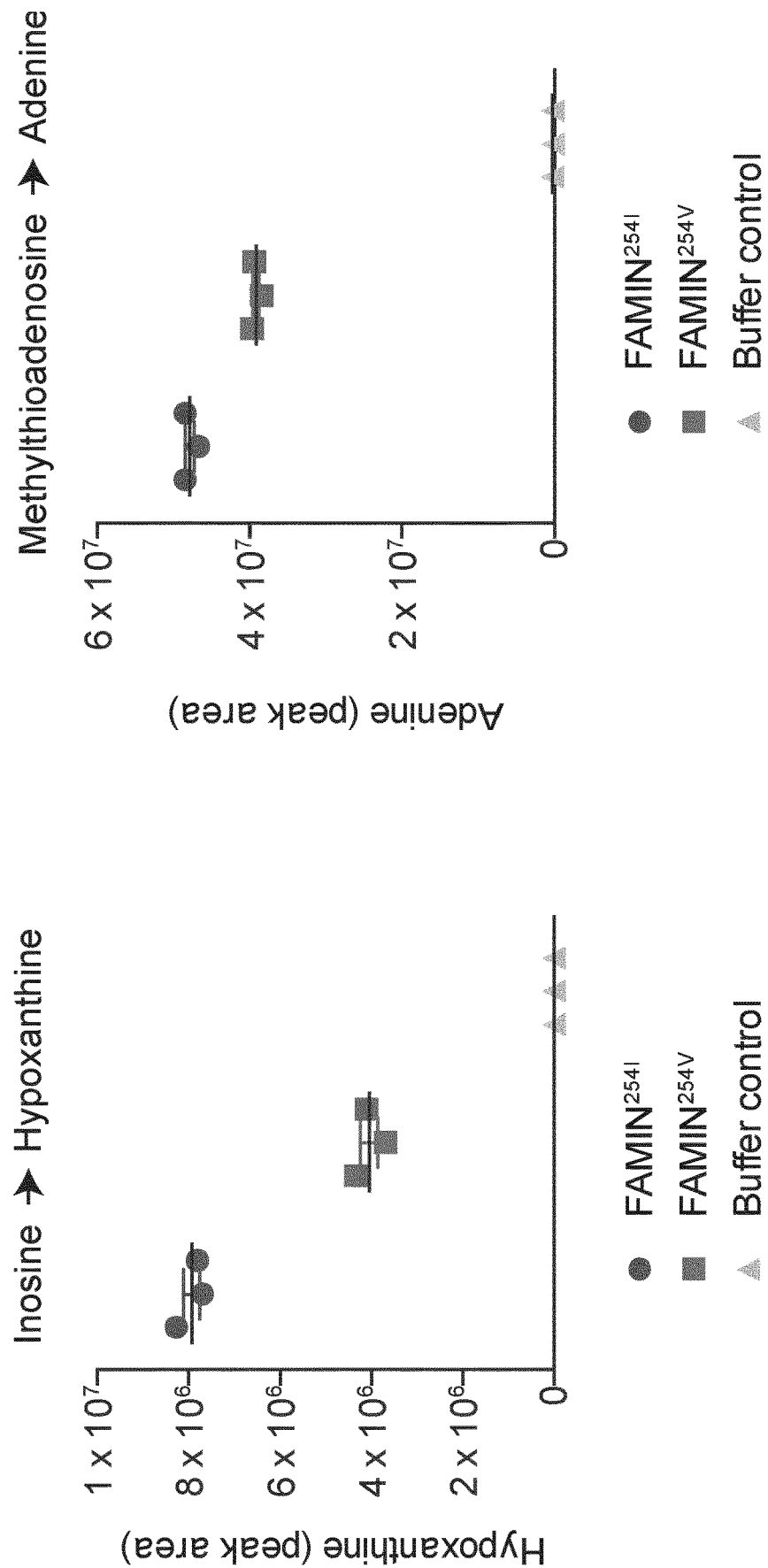

The apparent adenosine $K_m$ for FAMIN's deaminase activity was 11 μM, whereas its phosphorylase activities demonstrated $K_m$ values for adenosine, inosine, and MTA of 36 μM, 41 μM, and 1 μM, respectively (FIG. 3A). We next addressed how the I254V substitution, associated with risk for CD and leprosy, affected FAMIN activity. We compared recombinant $FAMIN^{254I}$ and the 'risk-variant' $FAMIN^{254V}$ for their adenosine metabolising activity. Compared with $FAMIN^{254I}$, adenosine consumption was approximately halved with $FAMIN^{254V}$ (FIG. 3B). Conversion to adenine was 10-fold lower with $FAMIN^{254V}$ compared to $FAMIN^{254I}$ (FIG. 3C). In contrast, the production of inosine and hypoxanthine by $FAMIN^{254V}$ was slightly higher and similar, respectively, compared to $FAMIN^{254I}$ (FIG. 3C, 3D). Ribose-1-phosphate generation was ~10-fold reduced with $FAMIN^{254V}$ compared to $FAMIN^{254I}$ (FIG. 3C), hence corresponding to the reduction in conversion to adenine. Thus, $FAMIN^{254V}$ markedly differed from $FAMIN^{254I}$ in how it metabolised adenosine, with only ~20% rather than 85% of consumed adenosine converted to adenine, instead diverting it to inosine and thence hypoxanthine (FIG. 3E). Consistent with the forward reaction, $FAMIN^{254V}$ generated 10-fold less adenosine from adenine and ribose-1-phosphate compared with $FAMIN^{254I}$ (FIG. 3F). $FAMIN^{254V}$ also demonstrated reduced phosphorylase activities towards inosine and MTA, since generation of hypoxanthine from inosine was ~50% lower, and adenine from MTA ~25% less compared to $FAMIN^{254I}$ (FIG. 3G). In summary, amongst FAMIN's enzymatic functions, its adenosine phosphorylase activity was the most attenuated in the $FAMIN^{254V}$ variant, whereas the adenosine deaminase activity appeared intact.

Figure 3H:
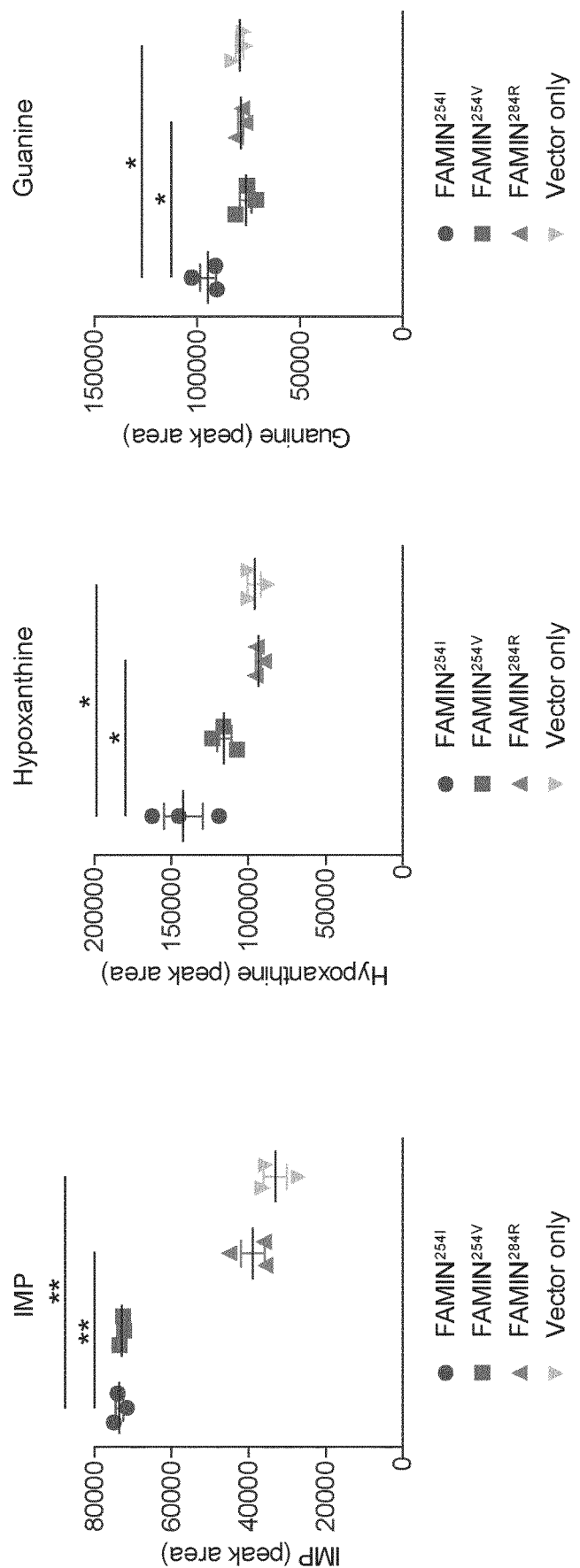
Figure 3I:
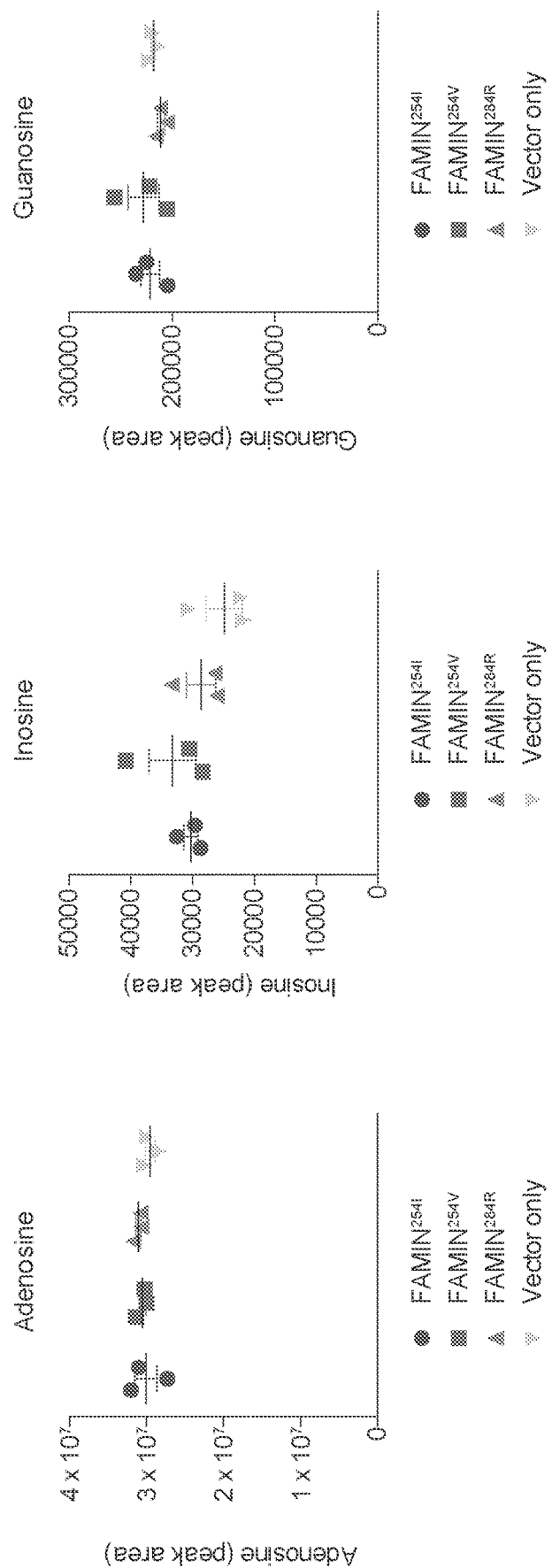
Figure 3J:
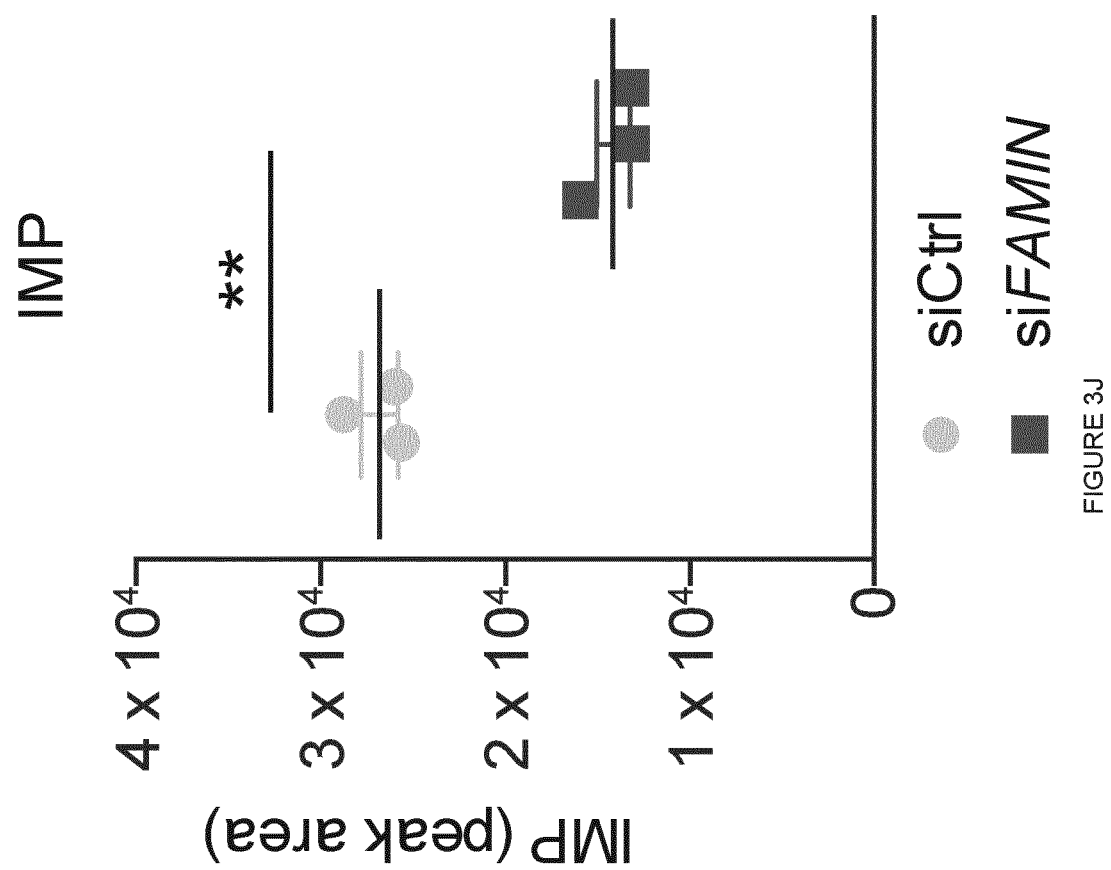
Figure 3K:
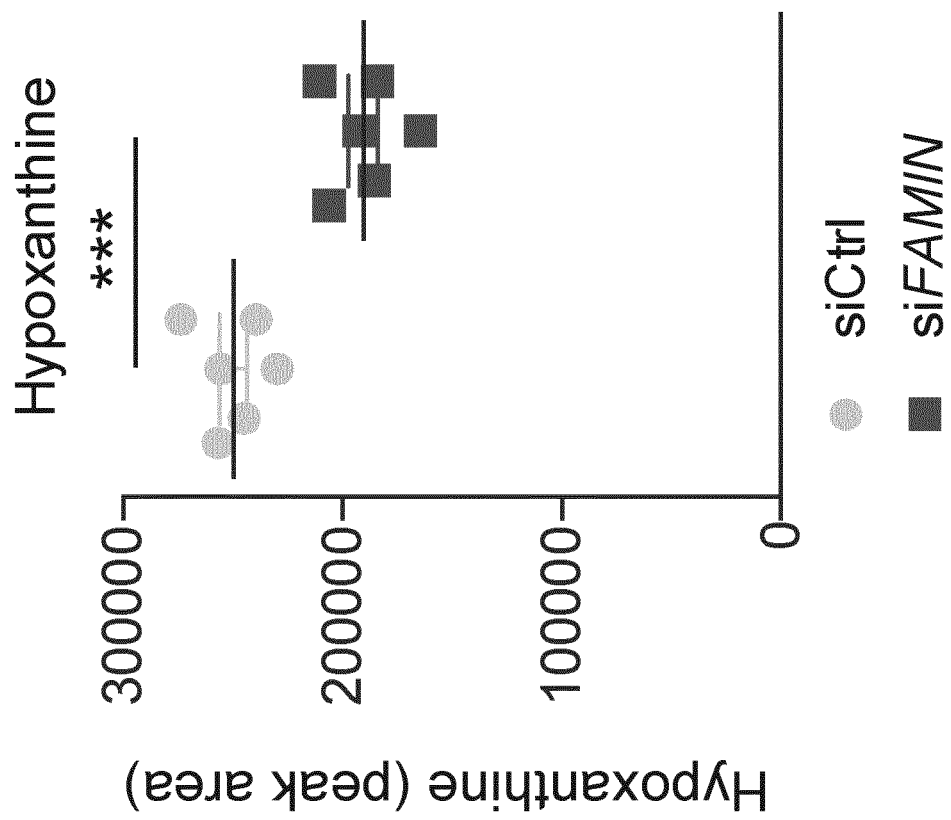
Figure 3K:
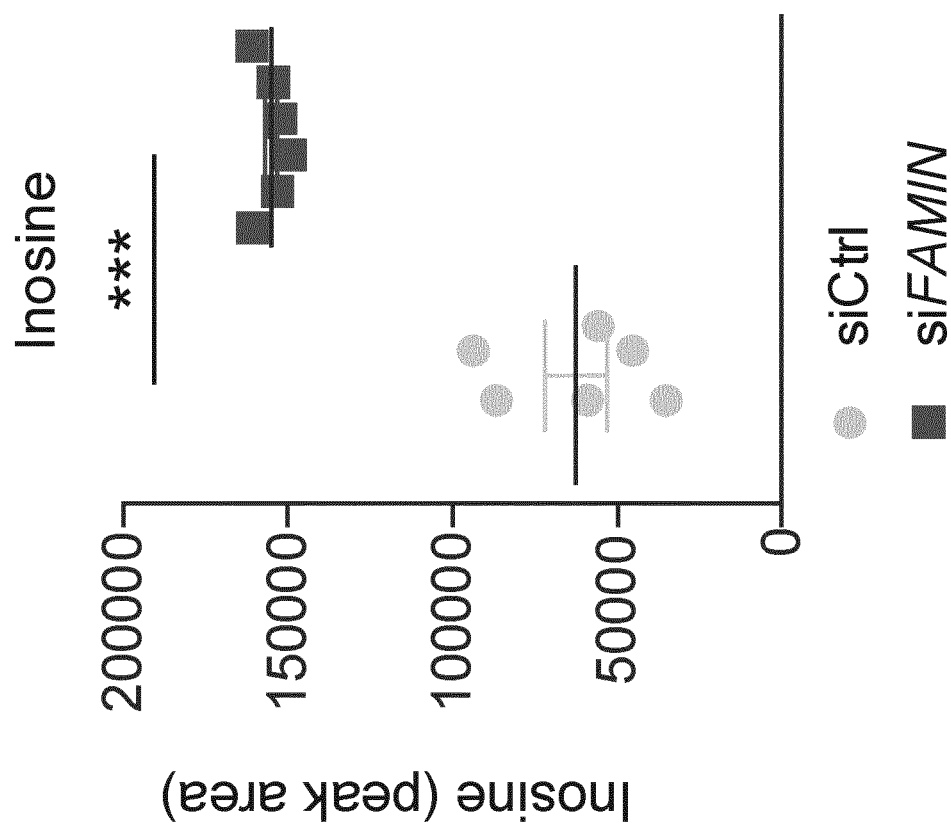
Figure 3L:
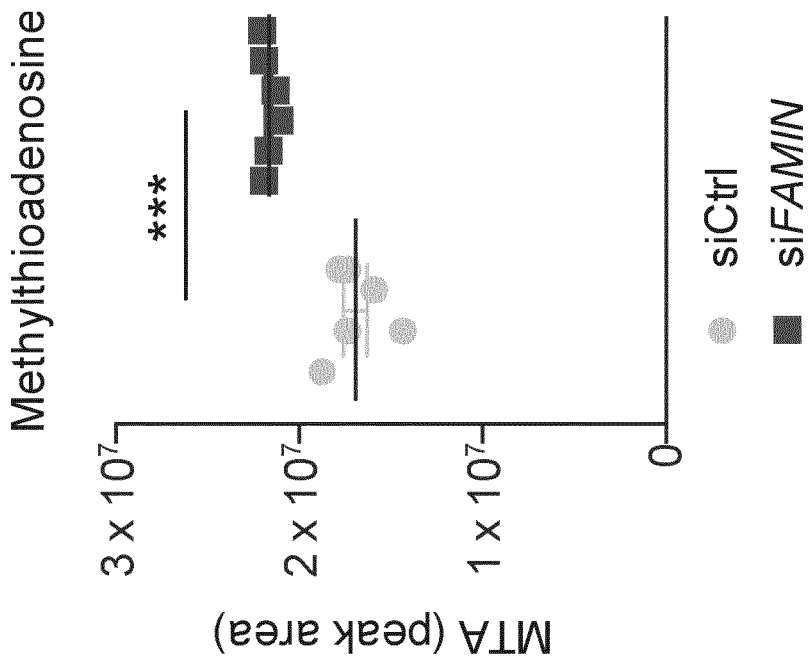
Figure 3L:
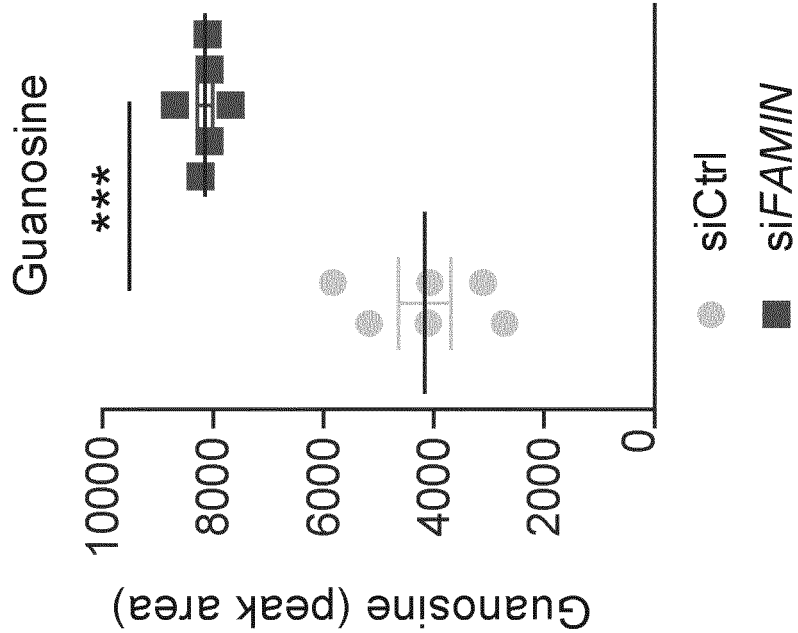

We next explored whether FAMIN affects cellular levels of purine metabolites. Transient transfection of FAMIN cDNA in HEK293T cells results in equally high protein expression of $FAMIN^{254I}$ and $FAMIN^{254V}$ and only low expression of $FAMIN^{284R}$ (1). 24 h after transfection with $FAMIN^{254I}$ plasmid, cellular hypoxanthine levels increased by 50% (FIG. 3H). Hypoxanthine modestly increased with $FAMIN^{254V}$, and remained unaltered in $FAMIN^{284R}$ compared to control transfectants (FIG. 3H). Cellular guanine levels were elevated in FAMIN$^{254I}$ transfected HEK293T cells (FIG. 3H), while total purine nucleoside levels were unaffected by expressing any of the FAMIN plasmids (FIG. 3I). Moreover, transfection with either FAMIN$^{254I}$ or FAMIN$^{254V}$ doubled the cellular levels of inosine monophosphate (IMP) (FIG. 3H). IMP is at the juncture of purine salvage and de novo synthesis and the obligatory intermediate of both (8). Conversely to the increase upon overexpression, cellular IMP levels were halved in HepG2 cells 24 h after transfection with FAMIN siRNA (FIG. 3J), which was amongst very few changes in metabolite levels observed that early. Acute silencing of FAMIN in HepG2 cells also reduced hypoxanthine levels, while it increased levels of inosine, guanosine and MTA (FIG. 3K, 3L). This demonstrated that FAMIN bolsters the generation of nucleobases for purine nucleotide salvage, and confirmed the activities established with pure recombinant protein as physiologically relevant.

Figure 4A:
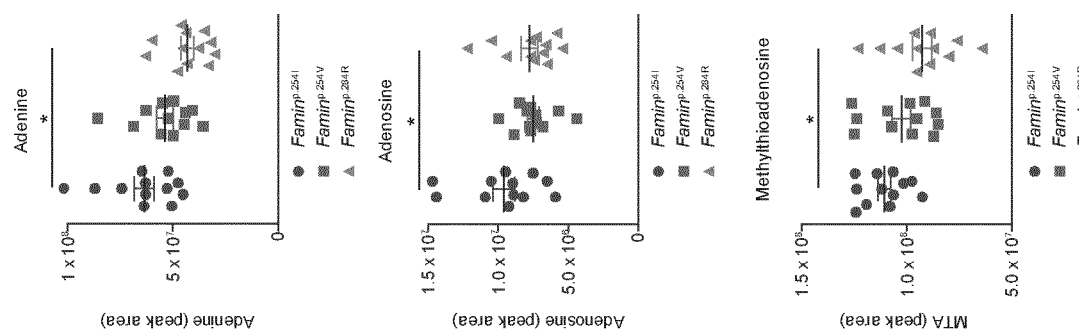
FIG. 4A shows adenine, adenosine and MTA levels in Famin$^{p.254I}$, Famin$^{p.254V}$, Famin$^{p.284R}$ M1 macrophages (n=12, mean±S.E.M.).
Figure 4B:
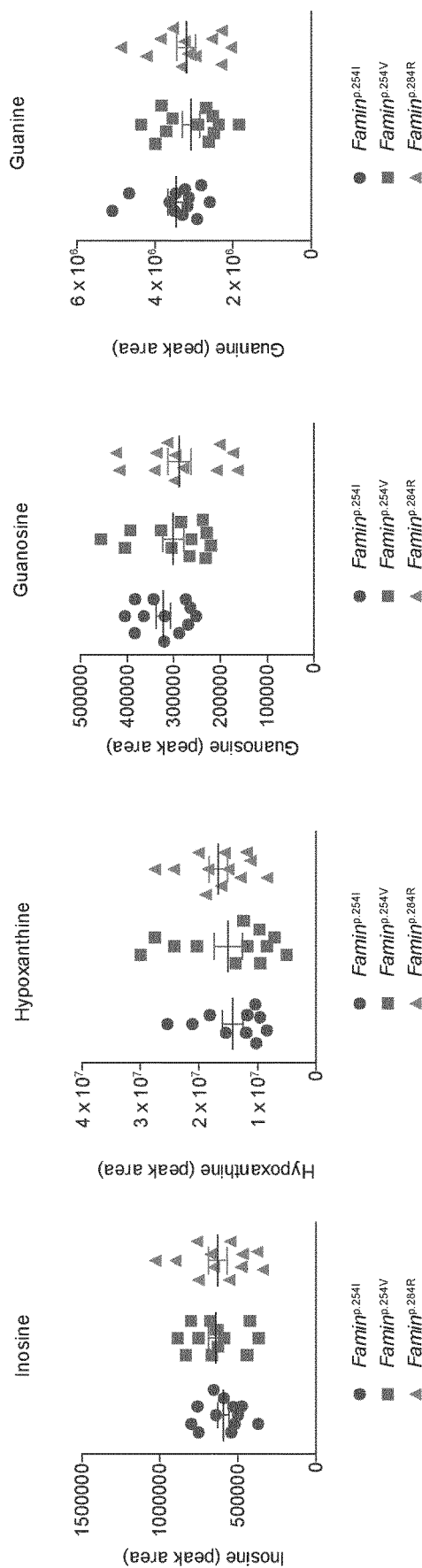
FIG. 4B shows inosine, hypoxanthine, guanosine and guanine levels in Famin$^{p.254I}$, Famin$^{p.254V}$, Famin$^{p.284R}$ M1 macrophages (n=12, mean±S.E.M.).
Figure 4C:
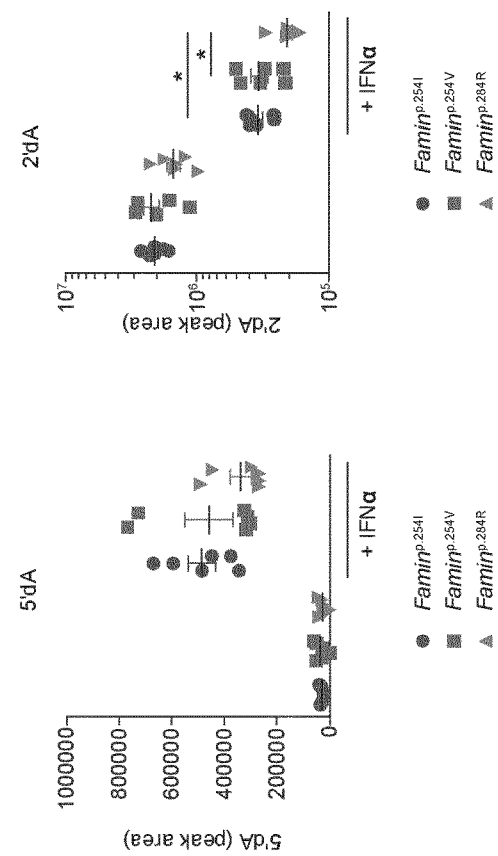
FIG. 4C shows 2' and 5'deoxyadenosine levels in Famin$^{p.254I}$, Famin$^{p.254V}$, Famin$^{p.284R}$ macrophages with or without treatment with interferon-α, (n=6, mean±S.E.M.). *P<0.05 (ANOVA; post-hoc Tukey's multiple comparisons test).

We next turned to terminally differentiated murine bone marrow (BM)-derived macrophages, which in contrast to proliferating HepG2 cells only employ purine nucleotide salvage, with hardly any de novo synthesis. Gene-editing human polymorphic FAMIN variants into the murine genome had established that compared to FAMIN$^{254I}$ (Famin$^{p.254I}$), reduced (Famin$^{p.254V}$) or absent (Famin$^{p.284R}$ or Famin$^{-/-}$) FAMIN activity in macrophages causes a progressive impairment in reactive oxygen species (ROS) production, bactericidal activity, inflammasome activation and cytokine secretion. This was linked to diminished de novo lipogenesis, oxidative phosphorylation, aerobic glycolysis and levels of adenosine triphosphate (ATP) (1). It was therefore interesting to observe that cellular levels of adenosine, adenine, and MTA were lowest in Famin$^{p.284R}$, intermediate in Famin$^{p.254V}$, and highest in Famin$^{p.254I}$ classically-activated bone marrow-derived macrophages (FIG. 4A). In contrast, cellular levels of inosine, hypoxanthine, guanosine and guanine were comparable across genotypes (FIG. 4B). Levels of 5'-deoxyadenosine, induced by interferon-α (9), were not significantly different between Famin genotypes, while 2'-deoxyadenosine levels were higher in Famin$^{p.254I}$ and Famin$^{p.254V}$ compared to Famin$^{p.284R}$ cells (FIG. 4C). Although total cellular metabolite levels may underestimate highly compartmentalised processes, such as with FAMIN that localises to the cytoplasmic surface of peroxisomes (1, 10), these data demonstrated that FAMIN promoted adenyl metabolism in macrophages.

Figure 4D:
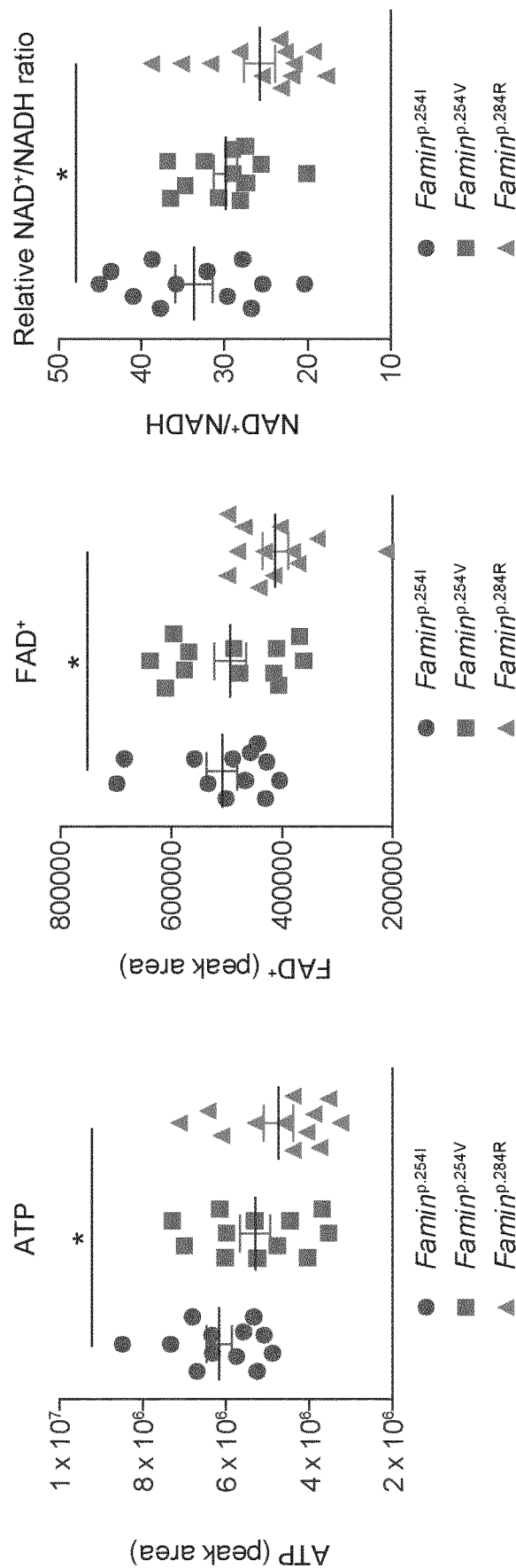
FIG. 4D shows ATP, FAD levels and NAD+/NADH ratio in Famin$^{p.254I}$, Famin$^{p.254V}$, Famin$^{p.284B}$ M1 macrophages (n=12, mean±S.E.M.). NAD+ and NADH each quantified as relative level, hence relative ratio.

Eukaryotic cells have been considered devoid of an activity that phosphorolytically converts adenosine or 2'-deoxyadenosine to adenine and ribose-phosphate (11-13). FAMIN adds such activity and furthermore combines in one single enzyme activities that are essential and non-redundant for purine nucleotide salvage. These had been thought to be encoded by single genes that are ubiquitously expressed: adenosine deaminase (ADA; secreted ADA2 is expressed from a separate gene), purine nucleoside phosphorylase (PNP) and S-methyl-5'-thioadenosine phosphorylase (MTAP) (14, 15). The reported apparent $K_m$ of these enzymes for their primary substrates is within the same range as FAMIN, indeed those of FAMIN appear slightly lower (16-18). The principal purine nucleosides, adenosine, inosine and guanosine, and their nucleobases, adenine, hypoxanthine and guanine, are neither precursors nor intermediates of de novo purine synthesis, but are generated by the reactions that supply purine nucleotide salvage (8). Purine nucleotide salvage proceeds from nucleobases via hypoxanthine guanine phosphoribosyl transferase (HPRT) and adenine phosphoribosyl transferase (APRT), and adenosine is the only nucleoside that can additionally be directly salvaged via adenosine kinase (ADK) (8). We show that FAMIN's trifunctionality expands core purine metabolism and adds an entirely novel layer of interconnectivity. This is associated with a gradual increase in total cellular ATP, FAD, and relative NAD/NADH ratio from loss-of-function Famin$^{p.284R}$ via hypomorphic Famin$^{p.254V}$ to Famin$^{p.254I}$ genotypes (FIG. 4D).

Figure 4E:
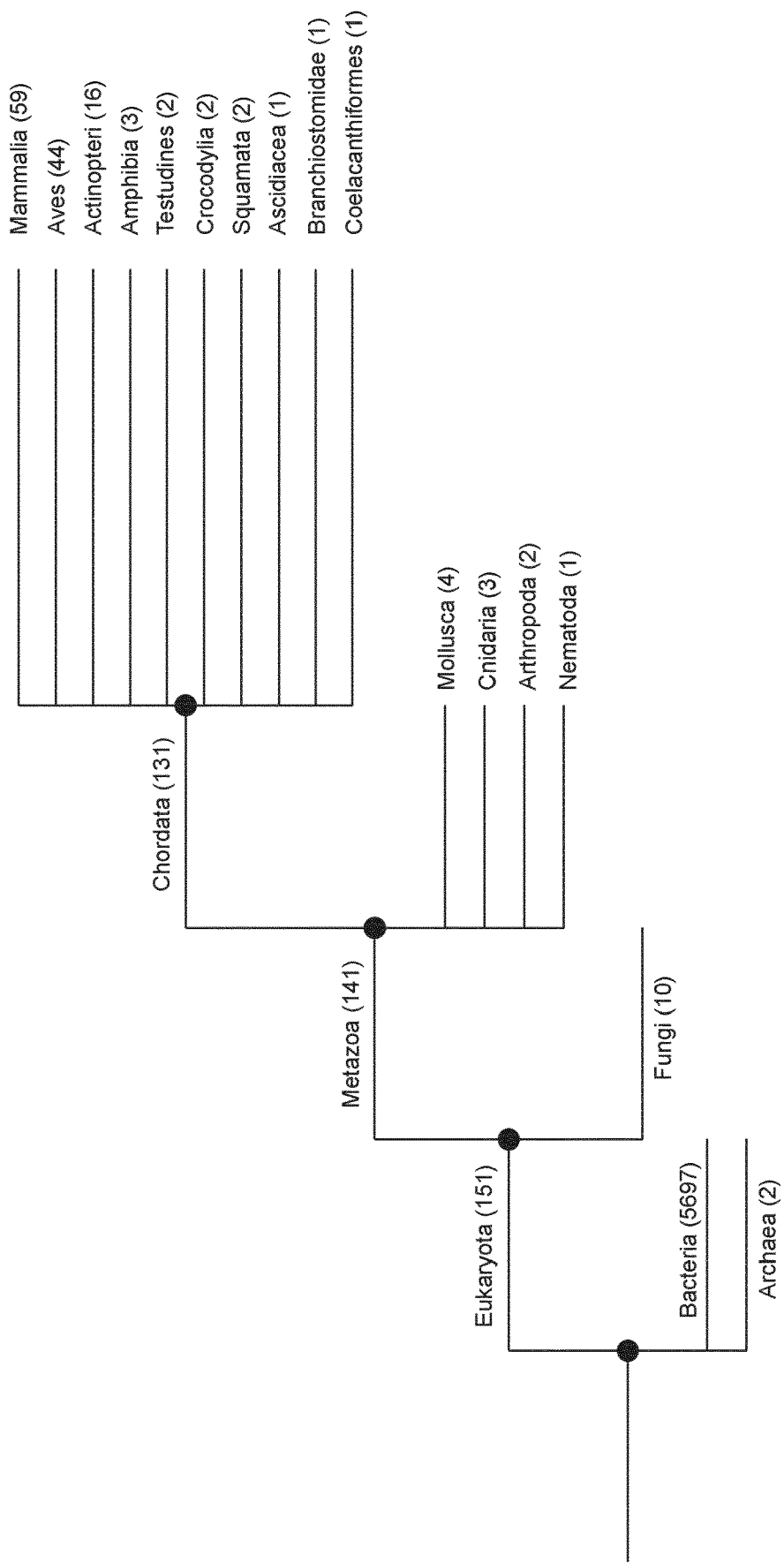
FIG. 4E shows the phylogenetic tree of FAMIN paralogues as generated using the HMMER database using human FAMIN protein sequence as the search input.
Figure 4F:
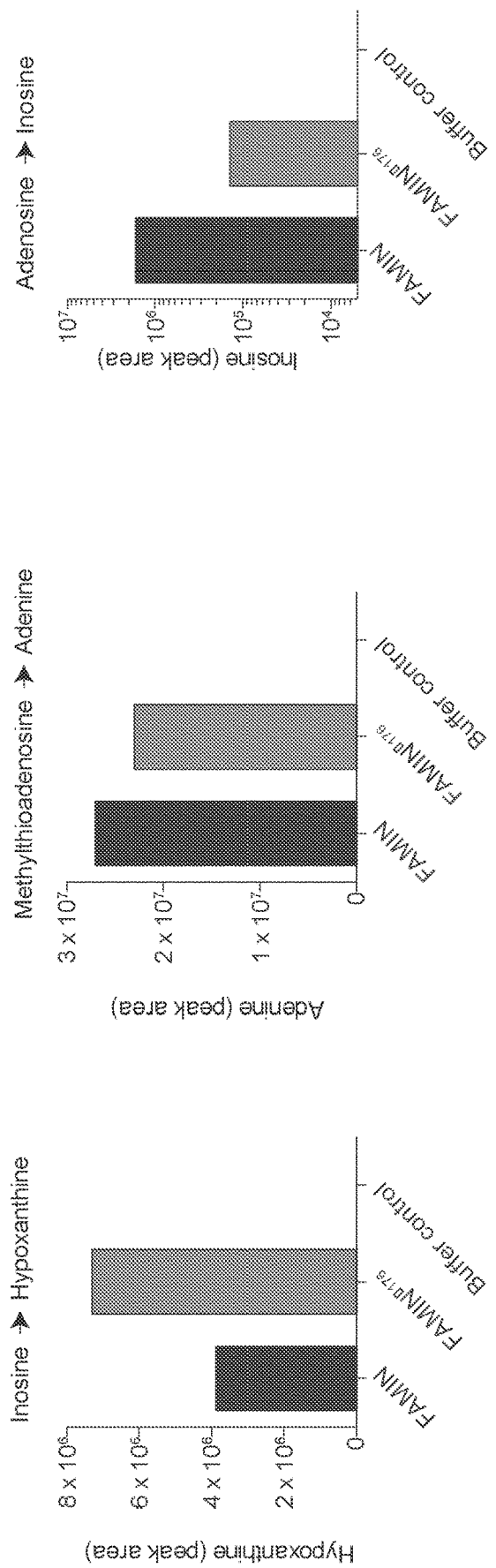
FIG. 4F shows EC 3.5.4.4 (adenosine deaminase), EC 2.4.2.1 (purine nucleoside phosphorylase) and EC 2.4.2.28 (MTA phosphorylase) activities of E. coli expressed recombinant full-length FAMIN and FAMIN$^{Δ176}$ as measured by inosine, hypoxanthine and adenine production following incubation of protein with 10 μM adenosine, inosine and MTA, respectively, in PBS.
Figure 4G:
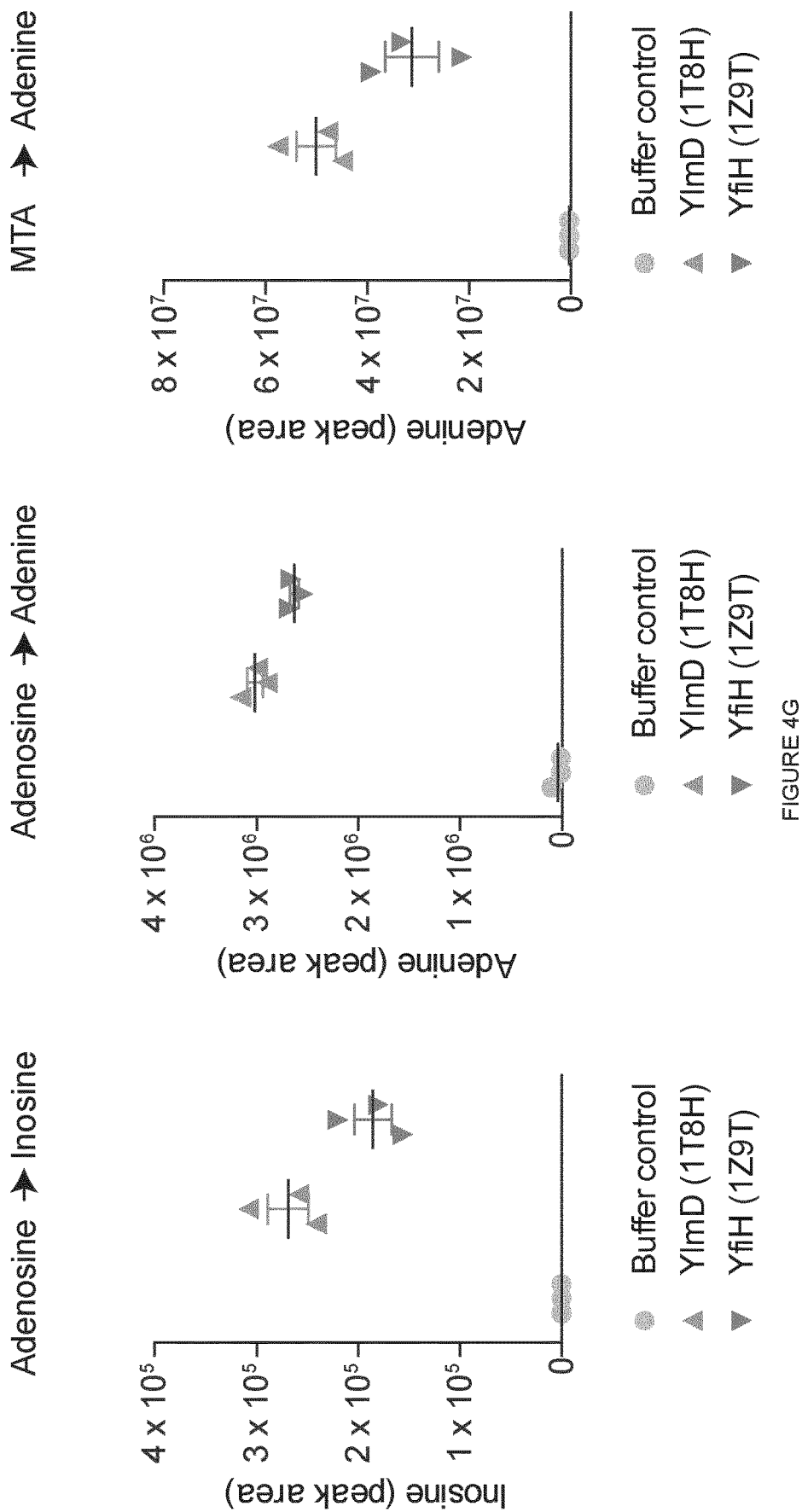
FIG. 4G shows EC 3.5.4.4 (Adenosine deaminase) and EC 2.4.2.28 (MTA phosphorylase) activities of E. coli expressed YlmD (1T8H), YfiH (1Z9T) as measured by inosine, and adenine and hypoxanthine production, respectively, following incubation of 10 μM adenosine or MTA in with 10 μg of recombinant proteins as indicated in PBS at 37° C. for 1 h (n=3, mean±S.E.M.).

Finally, we investigated whether FAMIN's trifunctionality in purine metabolism is evolutionarily conserved. The C terminal portion of FAMIN exhibits structural homology to Cluster of Orthologous Group (COG) 1496 proteins that contain the Pfam motif Domain of Unknown Function (DUF) 152, with paralogues widely distributed across species (FIG. 4E). An E. coli expressed maltose binding protein (MBP) fusion protein of truncated FAMIN, which contains the DUF152 homology domain only (FAMIN$^{\Delta 176}$, amino acids 176-430), exhibited all three enzymatic activities, similar to MBP-tagged full-length FAMIN (FIG. 4F). This demonstrated that the DUF152 homology region contains all enzymatic activity. Consistent with this, recombinantly expressed Strep-tagged COG1496 bacterial proteins YlmD (Uniprot P84138; from Geobacillus stearothermophilus) and YfiH (Uniprot P33644; from Escherichia coli strain K12), metabolise adenosine to both inosine and adenine, MTA to adenine, and inosine to hypoxanthine (FIG. 4G). Structures of YlmD (Protein Data Bank [PDB] accession code 1T8H) and YfiH (PDB 1Z9T), and other bacterial COG1496 proteins contain at least one $Zn^{2+}$ ion coordination, as do cytosine and cytidine deaminases (24). FAMIN, YlmD and YfiH contain a conserved cysteine-histidine-histidine triad, which in the structure of YfiH coordinates a zinc ion. Notably, the active sites of purine and pyrimidine amidohydrolases, including cytosine deaminase, ADA, and urease contain a zinc ion (25-27), which is often coordinated by a combination of histidine and cysteine side chains. However, the overall folds of these enzymes are different from YlmD and YfiH. Regarding genome context, yfiH is flanked in E. coli and S. flexneri by clpB and riuD, which encode an adenosine triphosphatase subunit of a chaperone and a ribosomal pseudouridine synthase, respectively (24). We conclude that FAMIN is indeed a prototype of a new class of trifunctional 'all-in-one' purine nucleoside metabolising enzymes that is conserved from bacteria to man.

Previously, MTAP had been thought to be the sole route of adenine generation and MTA metabolism (8, 28), and ADA and ADK the only routes of adenosine conversion (8, 19). Associated with peroxisomes, FAMIN may act on a pool of purine nucleosides which is partially or completely distinct from those ADA, PNP and MTAP act upon. Mutations in ADA and PNP cause severe combined immunodeficiency (SCID) (29-31). MTAP is frequently deleted in cancers, accounting for their altered methionine metabolism (32-35). Decreased or complete loss of FAMIN function, in contrast, presents with auto-inflammatory diseases. While expression of FAMIN is highest in macrophages, it is present in several other cell types, but not in T and B lymphocytes that are affected in SCID. FAMIN may hence re-shape concepts of organismal purine metabolism in addition to those on immune function.

In summary, FAMIN adds a surprising new layer to central adenyl metabolism, a highly interconnected and exquisitely tuned ancient metabolic circuitry that has adenosine and adenine at its centre and supplies adenyl groups for cofactors that are critically involved throughout metabolic processes.

Figure 5A:
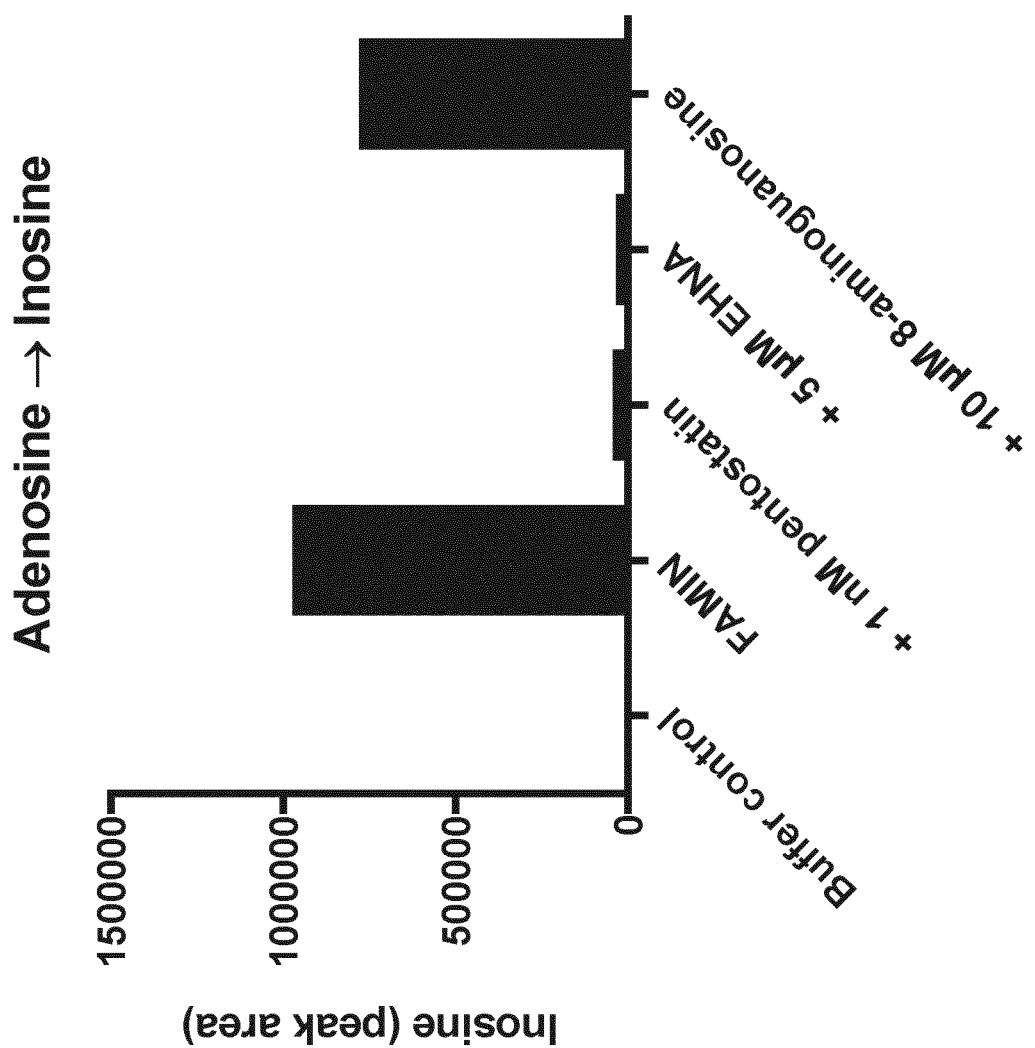
FIG. 5A shows levels of inosine after incubating 10 μg recombinant FAMIN or buffer control with 10 μM adenosine in PBS for 1 h at 37° C. in the presence or absence of pentostatin, erythro-9-(2-hydroxy-3-nonyl)adenine (EHNA), and 8-aminoguanosine at the indicated concentrations.
Figure 5B:
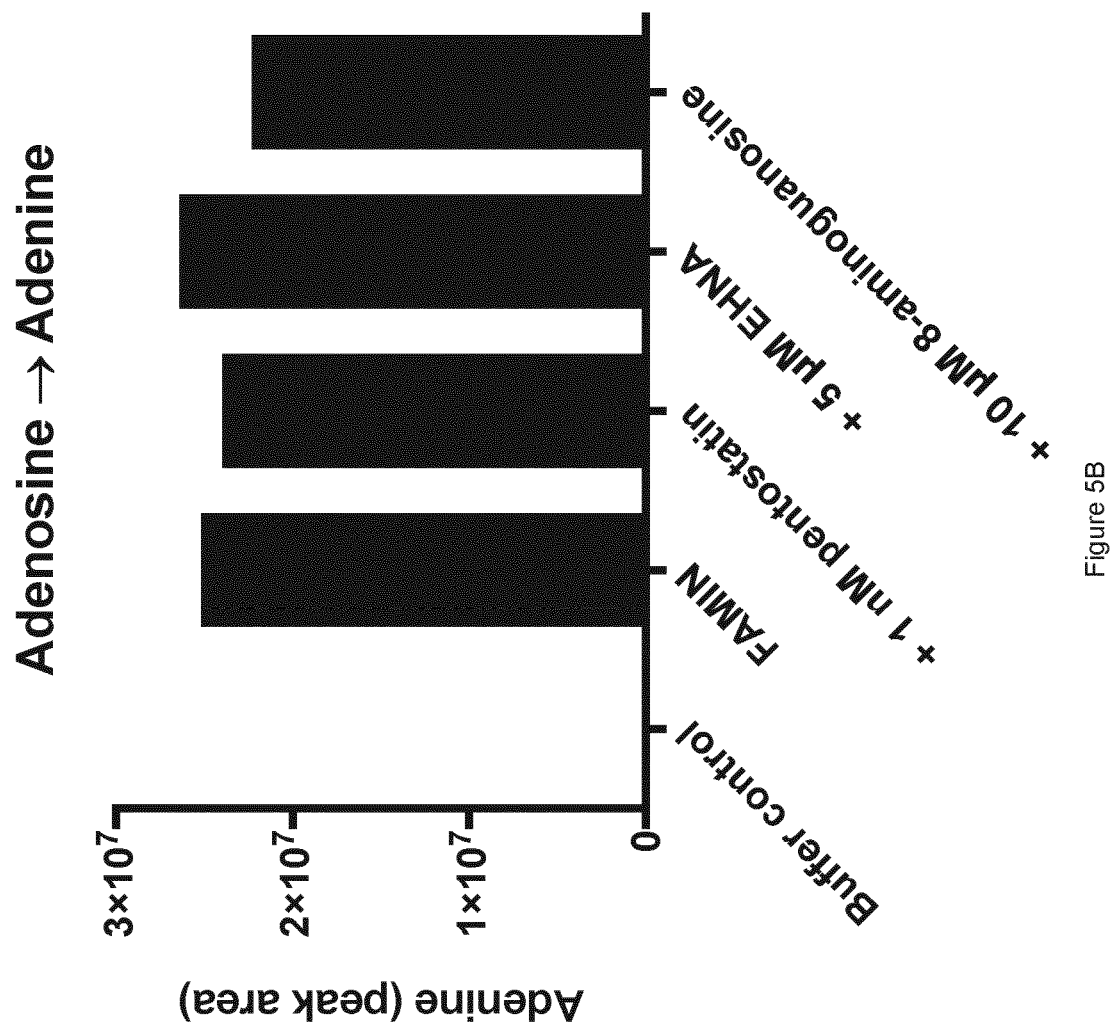
FIGS. 5B and 5C show levels of adenine and ribose-1-phosphate (R-1-P) in the reaction described in FIG. 5A.
Figure 5C:
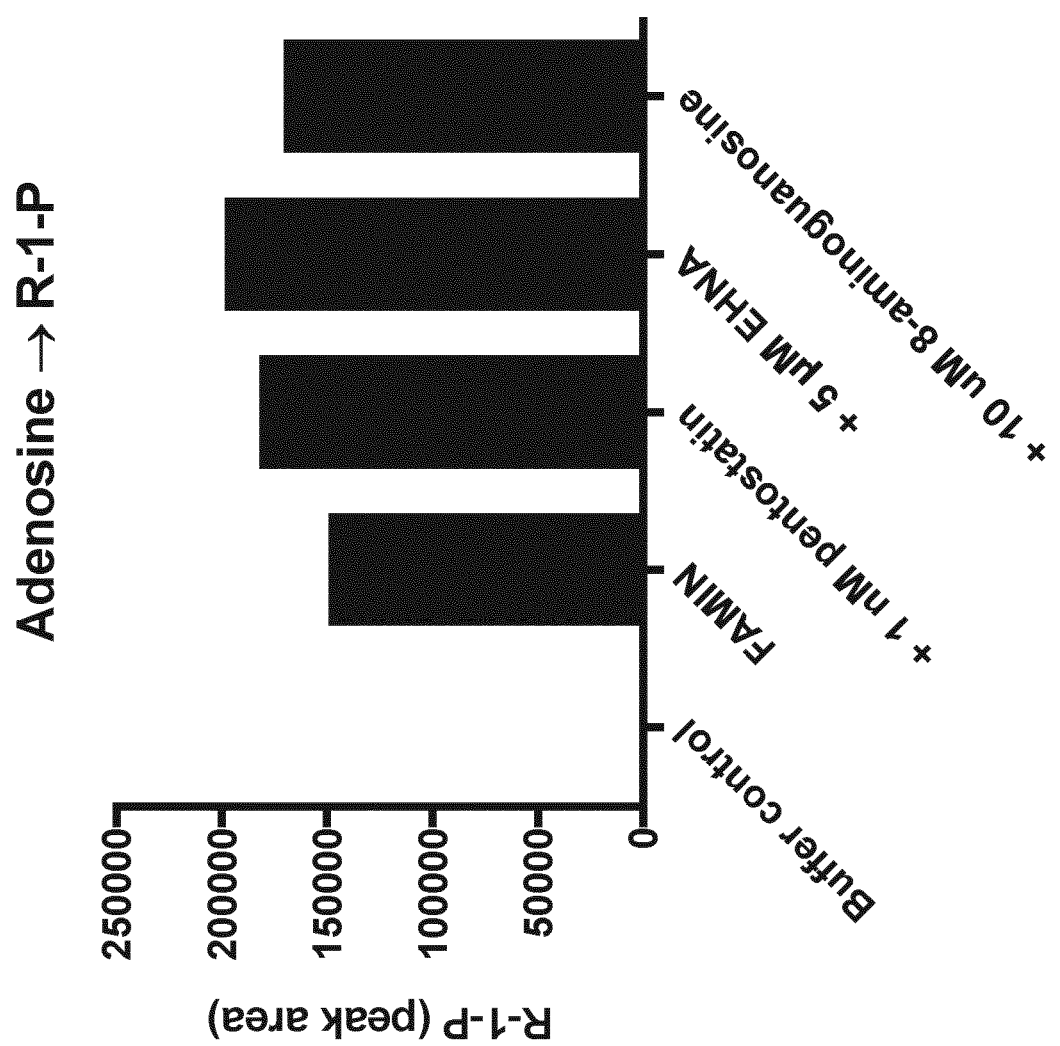
Figure 5D:
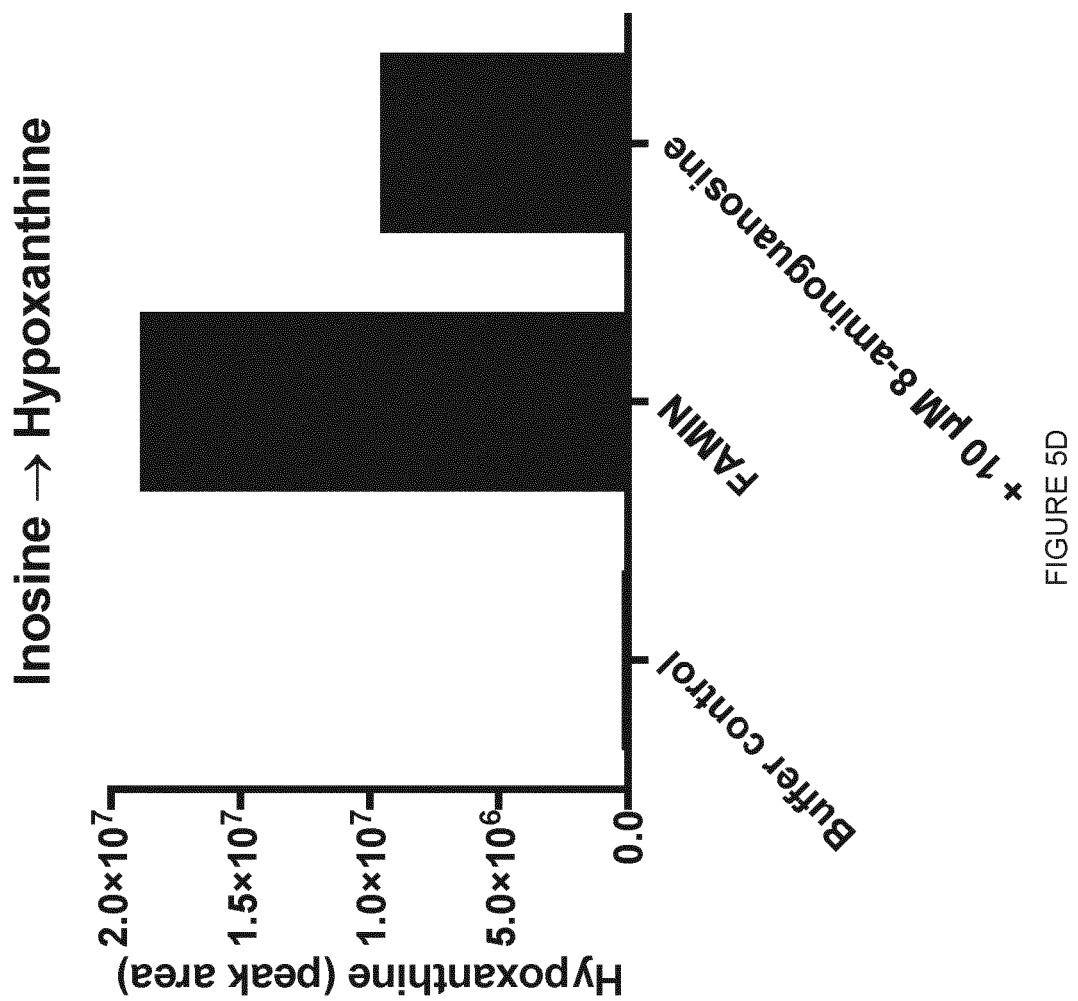
FIG. 5D shows levels of hypoxanthine after incubating 10 μg recombinant FAMIN or buffer control with 10 μM inosine in PBS for 1 h at 37° C. in the presence or absence of 8-aminoguanosine.
Figure 5E:
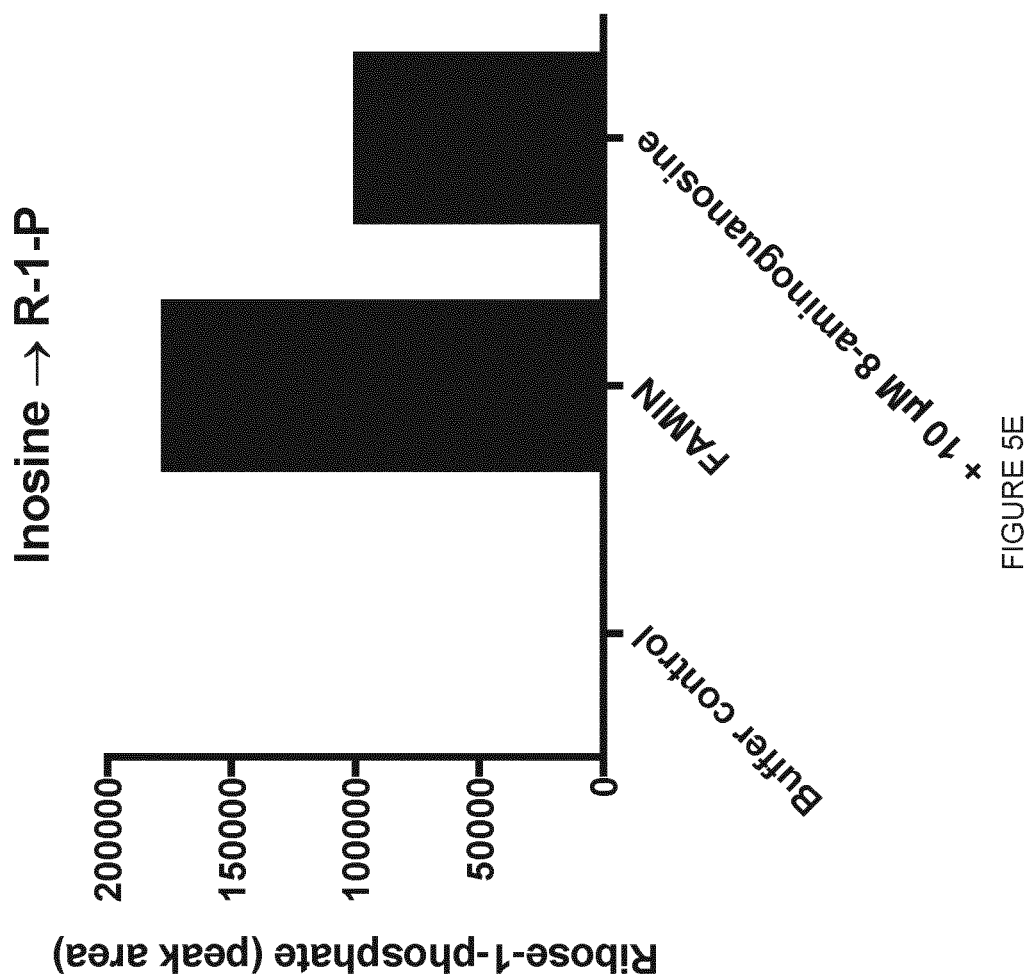
FIG. 5E shows R-1-P levels in the reaction described in FIG. 5D.

Applying methods disclosed herein, we identified pentostatin (PubchemID 439693, CAS ID 53910-25-1) and erythro-9-(2-hydroxy-3-nonyl)adenine (EHNA; PubchemID 3206, CAS ID 59262-86-1) as FAMIN inhibitors (FIG. 5A). Specifically, pentostatin and EHNA inhibited the adenosine deaminase activity of FAMIN (FIG. 5A), while leaving FAMIN's adenosine phosphorylase activity intact (FIG. 5B, C). 8-aminoguanosine (PubchemID 96849, CAS ID 3868-32-4) inhibited FAMIN's purine nucleoside phosphorylase activity as demonstrated by reduced generation of hypoxanthine and ribose-1-phosphate (R-1-P) from inosine (FIG. 5D, E). Importantly, 8-aminoguanosine did not affect FAMIN's adenosine phosphorylase activity as demonstrated by unimpaired generation of adenine and R-1-P from adenosine (FIG. 5C, D). This demonstrates that individual activities of FAMIN can be selectively targeted with small molecule modulators.

REFERENCES

1. M. Z. Cader et al., *Nat. Immunol.* 17, 1046 (2016).
2. L. A. O'Neill, E. J. Pearce, *J. Exp. Med.* 213, 15 (2016).
3. G. A. Prosser, G. Larrouy-Maumus, L. P. de Carvalho, *EMBO reports* 15, 657 (2014).
4. S. Zhao et al., *Nature* 502, 698 (2013).
5. J. Folch, M. Lees, G. H. Sloane Stanley, *J. Biol. Chem.* 226, 497 (1957).
6. V. Gorshkov et al., *J. Basic Microbiol.* 57, 998 (2017).
7. B. J. Landgraf, E. L. McCarthy, S. J. Booker, *Annu. Rev. Biochem.* 85, 485 (2016).
8. M. Camici, S. Allegrini, M. G. Tozzi, *FEBS J.*, (2018).
9. A. S. Gizzi et aL, *Nature* 558, 610 (2018).
10. G. Assadi et al., *PloS one* 11, e0168276 (2016).
11. M. Friedkin, H. M. Kalckar, in *The Enzymes*, P. D. Boyer, H. Lardy, K. Myrback, Eds. (Academic Press, New York, 1961), vol. 5, pp. 245.
12. T. P. Zimmerman, N. B. Gersten, A. F. Ross, R. P. Miech, *Can. J. Biochem.* 49, 1050 (1971).
13. J. T. Maynes et al., *Biochem. J.* 344 Pt 2, 585 (1999).
14. A. W. Murray, *Annu. Rev. Biochem.* 40, 811 (1971).
15. H. Ashihara, C. Stasolla, T. Fujimura, A. Crozier, *Phytochemistry* 147, 89 (2018).
16. E. R. Lindley, R. L. Pisoni, *Biochem. J.* 290 (Pt 2), 457 (1993).
17. A. Bzowska, E. Kulikowska, D. Shugar, *Pharmacol. Ther.* 88, 349 (2000).
18. F. Della Ragione et al., *Biochem. Biophys. Res. Commun.* 223, 514 (1996).
19. D. Boison, *Pharmacol. Rev.* 65, 906 (2013).
20. M. Camici, M. Garcia-Gil, M. G. Tozzi, *International journal of molecular sciences* 19, (2018).
21. A. Beloqui et al., *J. Biol. Chem.* 281, 22933 (2006).
22. A. I. Canas, S. Camarero, *Biotechnol. Adv.* 28, 694 (2010).
23. V. Perna, J. W. Agger, J. Holck, A. S. Meyer, *Scientific reports* 8, 8114 (2018).
24. Y. Kim et al., *Proteins* 63, 1097 (2006).
25. L. Holm, C. Sander, *Proteins* 28, 72 (1997).
26. D. K. Wilson, F. B. Rudolph, F. A. Quiocho, *Science* 252, 1278 (1991).
27. E. Jabri, M. B. Carr, R. P. Hausinger, P. A. Karplus, *Science* 268, 998 (1995).
28. E. Albers, *IUBMB life* 61, 1132 (2009).
29. K. L. Bradford, F. A. Moretti, D. A. Carbonaro-Sarracino, H. B. Gaspar, D. B. Kohn, *J. Clin. Immunol.* 37, 626 (2017).
30. E. R. Giblett, A. J. Ammann, D. W. Wara, R. Sandman, L. K. Diamond, *Lancet* 1, 1010 (1975).
31. E. R. Giblett, J. E. Anderson, F. Cohen, B. Pollara, H. J. Meuwissen, *Lancet* 2, 1067 (1972).
32. G. V. Kryukov et al., *Science* 351, 1214 (2016).
33. K. J. Mavrakis et al., *Science* 351, 1208 (2016).
34. T. Nobori et al., *Proc. Natl. Acad. Sci. U.S.A* 93, 6203 (1996).
35. Z. H. Chen, H. Zhang, T. M. Savarese, *Cancer Res.* 56, 1083 (1996).

| | Sequences | | | | | |
|---|---|---|---|---|---|---|
| 1 | maeavlidlf | glklnsqknc | hqtllktlna | vqyhhaakak | flcimccsni | syerdgeqdn |
| 61 | ceietsngls | alleefeivs | cpsmaatlyt | ikqkideknl | ssikvivprh | rktlmkafid |
| 121 | qlftdvynfe | fedlqvtfrg | glfkqsiein | vitaqelrgi | qneietflrs | lpalrgklti |
| 181 | itsslipdif | ihgfttrtgg | isyiptlssf | nlfssskrrd | pkvvvgenlr | rlanaagfnv |
| 241 | ekfyrikthh | sndiwimgrk | epdsydgitt | nqrgvtiaal | gadcipivfa | dpvkkacgva |
| 301 | hagwkgtllg | vamatvnami | aeygcsledi | vvvlgpsvgp | ccftlpresa | eafhnlhpac |
| 361 | vqlfdspnpc | idirkatril | leqggilpqn | iqdqnqdlnl | ctschpdkff | shvrdglnfg |
| 421 | tqigfisike | | | | | |

SEQ ID NO: 1 Homo sapiens FAMIN amino acid sequence (NP_001121775.1)

| 1 | agacctgcag | ctcctgccgc | cctgcgcccg | ctcccagggc | ccgtcgttcc | gccgccctat |
|---|---|---|---|---|---|---|
| 61 | ccctcctcaa | ggggcccta | gctgcctcct | cgcgaccctt | tccggactcg | gcctgcccac |
| 121 | tcctgcccgc | taacccgcct | ggctcccggg | cgagagccct | cgcgcggctc | tggttcctgt |
| 181 | tcctctaacg | ccgccggggc | tgcgggatgc | cgactccgcg | gaccgcccag | acccggaact |
| 241 | gctgaggcag | cagcgggctc | gcggcgcttg | gctcatcccg | ggattcccca | gctctcgcgc |
| 301 | tgggcccgcc | gcgttcgcac | caagcacgcc | aggcggccct | ggcctacctc | cctcccgcct |
| 361 | cccggcagct | ggcacgaggg | aacctggccg | tcaggtttcc | cctgggatcc | tgggacggta |

| | Sequences |
|---|---|
| 421 | tcaggcgggg aatctgtgcg gccgcggcga ggtgatttat ttggcataaa agtattcttt |
| 481 | caaggatggc agaagctgtt ttgattgatc tttttggttt gaaattgaac tctcaaaaaa |
| 541 | actgccatca gacattactg aagactttga atgctgtcca ataccaccat gctgccaagg |
| 601 | ccaagtttct ctgtataatg tgttgcagta acatcagcta tgaaagggat ggagaacaag |
| 661 | ataattgtga aatagaaaca agcaatggat tatcagctct cttggaagaa tttgagattg |
| 721 | ttagctgtcc cagcatggct gccactttgt ataccattaa acagaaaatt gatgaaaaaa |
| 781 | atctgagcag cattaaggta attgtaccca ggcacaggaa gacattaatg aaagctttta |
| 841 | ttgatcaact cttcactgat gtttacaatt ttgaatttga agatttgcaa gtgactttta |
| 901 | ggggagggct ttttaaacag tccattgaaa taaacgtaat cacagctcaa gaactaagag |
| 961 | gaattcagaa tgaaatagaa acattttga gaagtctgcc agcactgaga ggaaaattaa |
| 1021 | ctattatcac ttcttctttg atcccagata ttttcataca tggatttact acaagaacag |
| 1081 | gtgggatatc ttatatacca actcttagct cattcaatct cttcagtagt tccaaacgga |
| 1141 | gagatcccaa ggtagtggtt caagaaaatc tgcgtaggtt ggcgaatgct gcaggattta |
| 1201 | atgtggagaa attttaccga ataaagactc atcattccaa tgacatctgg attatgggaa |
| 1261 | gaaaggagcc tgactcttat gatggaataa ccacaaatca gagaggagtc acaatagcag |
| 1321 | ctcttggtgc agactgtata ccgatagttt ttgcagatcc agtcaaaaaa gcatgtgggg |
| 1381 | ttgctcacgc tggttggaaa ggtactttgt tgggtgttgc tatggctaca gtgaatgcta |
| 1441 | tgatagcaga atatggctgc agtttggaag acattgttgt tgtacttgga ccttcagtag |
| 1501 | gaccttgctg tttactctt ccaagggaat cagcagaggc atttcataat cttcatcctg |
| 1561 | catgtgtaca actatttgat tcaccaaatc cctgtatcga catccgtaaa gccacaagga |
| 1621 | ttcttctaga acagggagga attcttccac agaatattca ggaccagaac caagatctca |
| 1681 | acctctgtac atcttgccat cctgacaagt ttttctccca tgtccgagat ggccttaatt |
| 1741 | ttggtacaca gattggcttc atatcaatta agaatgaga tacttgactg gattttttgta |
| 1801 | taactgcttc ctgcctcctt ccaaactgac tgcaagagag aaatttagct gtttgattta |
| 1861 | cttaaaacca aatggattac aatggataat tcatcttttg ggtatatttt tactattatt |
| 1921 | caaagccaaa tgattttcat ttaattgtaa taataactga caaaaatcag tatgttgtag |
| 1981 | ctaatatgtt ttatgcatga gaattattct taaagtttgt tctccctgtt tattacacag |
| 2041 | atcaggaata gatttgttca gttcagtatt tattggatac cctctattgg tcaggcattg |
| 2101 | tgttaagcat atgtgaatca aaatgaacac aacttttttcc tttgagtctg atacagtgaa |
| 2161 | ggagataaac acttctacaa cttaaattta attttaatag cagtagaaga gaacataagg |
| 2221 | aatagaggtt aattttaccc agaagcagga tagagaaaat attacagaga aaatcacata |
| 2281 | tcacatgggc tcgaaagatg tagaggtttt tgacaaatga agaacaacca taacaggtag |
| 2341 | agggaacacc atgaaccagg gcatgaaact gaaagtgcat aacatattct agagagagaa |
| 2401 | gggtgtgggc atgagttagg gctggaaaaa caggttggaa acagataagt aagggtctca |
| 2461 | aatgcaatgt caaagagctt gcagtttatt ttccaggcaa tgagtaggca gccaaaaaaa |
| 2521 | aaaaagtaag gatgtttttt ttttttttcc catggcatca tatttaagag gatggattta |
| 2581 | aattgtgtga gaccaaagca tagagactag ataagaggcg atcaaaatat ttcaaaaaga |
| 2641 | aataatgaag atccaatgaa ggaagtggaa attaaaatag ggaagagagt agatggatta |

| Sequences | | | | | |
|---|---|---|---|---|---|
| 2701 | gagagacatt | taagagatgg | aatcaataga | tcctgttact | agataatgga agtaagaggt |
| 2761 | gaggaagagt | ggaaaagtca | ttaatgactc | taagatttct | gcttggctgc ttaccaagat |
| 2821 | tggcaacaaa | gggagggaga | aggtttggaa | aaagagagaa | ggataatgag tttgacttta |
| 2881 | catagaatga | agggcatcca | gatagaaatc | tttggttaat | aattagaaat atagacctag |
| 2941 | aaattaggag | gaaacctgag | acagagacaa | atatttcaaa | gcttacaata cagagatgat |
| 3001 | acctgattct | attggagcag | gtttgatcat | ctaggcagaa | attaggatga gaaaaagga |
| 3061 | gatccaataa | tacaacctta | tagtcacaga | agtaagaaaa | aaagggtagt tgttttgaag |
| 3121 | aagccaggat | aggtgtggaa | agtactcaaa | agaaatctt | cagggataaa ataaagtgat |
| 3181 | aatttaaaag | aaatcaatgg | attaaacata | ttgaaactgt | tctataggca gtggtcattg |
| 3241 | agtcagcttt | cagtgcatta | ggaagaagat | gcataggtgt | caactctttt ctgacagcat |
| 3301 | ttactagaga | agagaaaaag | ctggggacta | catcttcaag | gaagggactt tttttggatg |
| 3361 | agcagttttg | agtgtgtttg | tcagttaaag | agaggaatta | ggttagtttt catttgggaa |
| 3421 | aaattgtata | tatatttaat | gtaagttatc | acattgcatc | ttaaaaatat tcttatttaa |
| 3481 | tacatatatt | tcctacatgt | atatgtggta | gcatgatagc | aaataacatt tgtttggtat |
| 3541 | ttccaaagga | ctttcatgta | cattgcctca | ttttacctt | acagctactc tgaaatacac |
| 3601 | aggcattatc | ccttttattc | agctgagaaa | actgagcttc | attgaggtgg aggtcaaaaa |
| 3661 | tcacaaaatt | tgtgatgaat | taagattga | acatatgttt | tgtgactcca gttttccttt |
| 3721 | cagattttaa | aattaattaa | agggatcttc | attatacttt | tattgttaac tttttgttaa |
| 3781 | cataatttat | tcatacattc | agtgaaaatt | ttgttgaggt | actgggacag gttaaaaat |
| 3841 | acagttgtag | ccctcaggat | attttaatatc | cagtgaaaag | tgacagtcag taaaccaaca |
| 3901 | atctcaatac | tttgatatat | gttgtgaggt | tgtgataacc | gattcttgtt tagtttaatt |
| 3961 | ctatatctcc | cttagaccag | tgttaaattt | aaataaaaca | cctcattttt tccaattcag |
| 4021 | ggaaggcact | aaacataaag | cataggatag | aaatgttgaa | ctcatccaaa atattatttt |
| 4081 | gtttaatgaa | aatgatgaag | attaaggaat | acttccatgt | attgagtaag gttgataatt |
| 4141 | ttctaattct | tcactgtgca | ttattttgtt | tgaagttggt | aaatttggag tatcctgcag |
| 4201 | acacattttg | ctttatgtac | tacaacattc | tacaaccaaa | taaaaattat tttgattatc |
| 4261 | tgaaaaaaaa | aaaaaaaaaa | aaaaaaaa | | |

SEQ ID NO: 2 Homo sapiens FAMIN coding sequence (NM_001128303.1)

The invention claimed is:

1. A method of measuring the activity of a FAMIN protein comprising;
   providing an isolated FAMIN protein; and
   determining the adenosine deaminase activity, purine nucleoside phosphorylase activity and/or methylthioadenosine phosphorylase activity of the FAMIN protein.

2. A method according to claim 1 wherein the purine nucleoside phosphorylase activity is an adenosine phosphorylase activity.

3. A method according to claim 1 wherein the adenosine deaminase activity of the FAMIN protein is determined by measuring the conversion of an adenosine molecule into an inosine molecule in the presence of the FAMIN protein.

4. A method according to claim 3 wherein the method comprises contacting the isolated FAMIN protein with adenosine nucleoside in a reaction solution; and determining the amount of adenosine nucleoside or inosine nucleoside in the reaction solution following said contacting.

5. A method according to claim 3 wherein a decrease in the concentration of adenosine nucleoside or an increase in the concentration of inosine nucleoside in the reaction solution is indicative of adenosine deaminase activity.

6. A method according to claim 3 wherein; (i) the adenosine molecule is adenosine and the inosine molecule is inosine; (ii) the adenosine molecule is deoxyadenosine and the inosine molecule is deoxyinosine (iii) the adenosine molecule is 2'-deoxyadenosine and the inosine molecule is 2'deoxyinosine; or (iv) the adenosine molecule is 5'-deoxyadenosine and the inosine molecule is 5'deoxyinosine.

7. A method according to claim 1 wherein the purine nucleoside phosphorylase activity of the FAMIN protein is determined by measuring the conversion of a purine nucleoside into a nucleobase and a ribose-1-phosphate molecule in the presence of the FAMIN protein.

8. A method according to claim 7 wherein the method comprises contacting the isolated FAMIN protein with a purine nucleoside in a reaction solution; and determining the amount of purine nucleoside; or purine nucleobase and/or ribose-1-phosphate molecule in the reaction solution following said contacting.

9. A method according to claim 8 wherein the reaction solution comprises inorganic phosphate.

10. A method according to claim 7 wherein a decrease in the concentration of purine nucleoside or an increase in the concentration of purine nucleobase and/or ribose-1-phosphate molecule in the reaction solution is indicative of purine nucleoside phosphorylase activity.

11. A method according to claim 7 wherein
   (i) the purine nucleoside is guanosine, the purine nucleobase is guanine and the ribose-1-phosphate molecule is α-D-ribose-1-phosphate;
   (ii) the purine nucleoside is adenosine, the purine nucleobase is adenine and the ribose-1-phosphate molecule is α-D-ribose-1-phosphate;
   (iii) the purine nucleoside is 2'-deoxyadenosine, the purine nucleobase is adenine and the ribose-1-phosphate molecule is 2' deoxy α-D-ribose-1-phosphate; or
   (iv) the purine nucleoside is 5'-deoxyadenosine, the purine nucleobase is adenine and the ribose-1-phosphate molecule is 5' deoxy α-D-ribose-1-phosphate.

12. A method according to claim 7 wherein the purine nucleoside is an inosine molecule.

13. A method according to claim 12 wherein;
   (i) the inosine molecule is inosine, the purine nucleobase is hypoxanthine and the ribose-1-phosphate molecule is α-D-ribose-1-phosphate; or
   (ii) the inosine molecule is deoxyinosine; the purine nucleobase is hypoxanthine and the ribose-1-phosphate molecule is 2'deoxy-α-D-ribose-1-phosphate.

14. A method according to claim 1 wherein the purine nucleoside phosphorylase activity of the FAMIN protein is determined by measuring the conversion of a nucleobase and a ribose-1-phosphate molecule into a purine nucleoside in the presence of the FAMIN protein.

15. A method according to claim 14 wherein the method comprises contacting the isolated FAMIN protein with a nucleobase and a ribose-1-phosphate molecule in a reaction solution; and determining the amount of purine nucleoside; or purine nucleobase and/or ribose-1-phosphate molecule in the reaction solution following said contacting.

16. A method according to claim 14 wherein a decrease in the concentration of nucleobase and a ribose-1-phosphate molecule or an increase in the concentration of purine nucleoside in the reaction solution is indicative of purine nucleoside phosphorylase activity.

17. A method according to claim 1 wherein the methylthioadenosine phosphorylase activity of the FAMIN protein is determined by measuring the conversion of methylthioadenosine into adenine and a methylthioribose-1-phosphate molecule in the presence of the FAMIN protein.

18. A method according to claim 17 wherein the method comprises contacting the isolated FAMIN protein with a methylthioadenosine nucleoside in a reaction solution; and determining the amount of methylthioadenosine nucleoside, adenine nucleobase and/or methylthioribose-1-phosphate molecule in the reaction solution following said contacting.

19. A method according to claim 18 wherein the reaction solution comprises inorganic phosphate.

20. A method according to claim 18 wherein a decrease in the concentration of methylthioadenosine nucleoside or an increase in the concentration of adenine nucleobase and/or methylthioribose-1-phosphate molecule in the reaction solution is indicative of methylthioadenosine phosphorylase activity.

21. A method according to claim 17 wherein the methylthioadenosine nucleoside is 5-methylthioadenosine and the methylthioribose-1-phosphate molecule is S-methyl-5-thio-α-D-ribose-1-phosphate.

22. A method according to claim 1 wherein the methylthioadenosine phosphorylase activity of the FAMIN protein is determined by measuring the conversion of adenine nucleobase and a methylthioribose-1-phosphate molecule into methylthioadenosine nucleoside in the presence of the FAMIN protein.

23. A method according to claim 22 wherein the method comprises contacting the isolated FAMIN protein with adenine nucleobase and a methylthioribose-1-phosphate molecule in a reaction solution; and determining the amount of methylthioadenosine nucleoside, adenine nucleobase and/or methylthioribose-1-phosphate molecule in the reaction solution following said contacting.

24. A method according to claim 22 wherein a decrease in the concentration of adenine nucleobase and/or methylthioribose-1-phosphate molecule or an increase in the concentration of methylthioadenosine nucleoside in the reaction solution is indicative of methylthioadenosine phosphorylase activity.

25. A method according to claim 1 comprising determining the adenosine deaminase activity and purine nucleoside phosphorylase activity of the FAMIN molecule.

26. A method according to claim 25 wherein the method comprising contacting the FAMIN protein with adenosine nucleoside in a reaction solution; and determining the amount of adenosine nucleoside, hypoxanthine, and/or ribose-1-phosphate molecule in the reaction solution following said contacting.

27. A method according to claim 26 wherein the reaction solution comprises inorganic phosphate.

28. A method according to claim 26 wherein a decrease in the concentration of adenosine nucleoside or an increase in the concentration of hypoxanthine and/or ribose-1-phosphate molecule in the reaction solution is indicative of adenosine deaminase and purine nucleoside phosphorylase activity.

29. A method according to claim 26 wherein
(i) the adenosine nucleoside is adenosine and the ribose-1-phosphate molecule is α-D-ribose-1-phosphate;
(ii) the adenosine nucleoside is 2'-deoxyadenosine and the ribose-1-phosphate is 2'deoxy-α-D-ribose-1-phosphate; or
(iii) the adenosine nucleoside is 5'-deoxyadenosine and the ribose-1-phosphate is 5' deoxy-α-D-ribose-1-phosphate.

30. A method according to claim 1 comprising determining the adenosine deaminase activity, purine nucleoside phosphorylase activity and methylthioadenosine phosphorylase activity of the FAMIN protein.

31. A method according to claim 1 comprising determining the adenosine deaminase activity and the methylthioadenosine phosphorylase activity of the FAMIN protein.

32. A method according to claim 1 comprising determining the purine nucleoside phosphorylase activity and the methylthioadenosine phosphorylase activity of the FAMIN protein.

33. A method according to claim 1 wherein the FAMIN protein is human FAMIN.

34. A method according to claim 33 wherein the FAMIN protein comprises an amino acid sequence having at least 80% identity to the sequence of amino acids 176-430 of SEQ ID NO: 1.

35. A method according to claim 33 wherein the FAMIN protein comprises an Ile residue or a Val residue at a position corresponding to position 254 of the amino acid sequence of SEQ ID NO: 1.

36. A method according to claim 1 comprising identifying a test compound that inhibits FAMIN activity and optionally isolating and/or purifying the identified test compound.

37. A method of screening for a compound that modulates the activity of a FAMIN protein comprising;
determining the adenosine deaminase activity, purine nucleoside phosphorylase activity and/or methylthioadenosine phosphorylase activity of an isolated FAMIN protein in the presence and absence of a test compound, wherein a difference in the adenosine deaminase activity, purine nucleoside phosphorylase activity and/or methylthioadenosine phosphorylase activity of the FAMIN protein in the presence relative to the absence of test compound is indicative that the test compound modulates the activity of the FAMIN protein.

38. A method according to claim 37 wherein a decrease in the adenosine deaminase activity, purine nucleoside phosphorylase activity and/or methylthioadenosine phosphorylase activity of the FAMIN protein in the presence relative to the absence of test compound is indicative that the test compound is a FAMIN inhibitor.

39. A method according to claim 37 wherein an increase in the adenosine deaminase activity, purine nucleoside phosphorylase activity and/or methylthioadenosine phosphorylase activity of the FAMIN protein in the presence relative to the absence of test compound is indicative that the test compound is a FAMIN potentiator.

* * * * *